US007771730B2

(12) United States Patent
Nguyen et al.

(10) Patent No.: US 7,771,730 B2
(45) Date of Patent: Aug. 10, 2010

(54) METHODS AND REAGENTS FOR DIAGNOSING HANTAVIRUS INFECTION

(75) Inventors: Steve H. Nguyen, O

OTHER PUBLICATIONS

Lee, Ho Wang, et al., "Laboratory-Acquired Infections with Hantaan Virus . . . " J. of Infectious Diseases, vol. 146, No. 5, Nov. 1982, 645-651.

Lee, Ho Wang, et al., "Isolation of the Etiologic Agent of Korean Hemorrhagic Fever", J. of Infectious Diseases, vol. 137, No. 3, Mar. 1978, p. 298-308.

Lundkvist, et al., "Mapping of B-Cell Determinants in the Nucleocapsid Protein of Puumala Virus . . . " Clinical and Diagnostic Laboratory Immunology, Jan. 1995, p. 82-86.

Vallari, et al. "Serological Markers of Posttransfusion Hepatitis C Viral Infection" J. of Clinical Microbiology, Mar. 1992 p. 552-556.

Yee, et al., "Rapid and Simple Method for Screening Wild Rodents for Antibodies to Sin Nombre Hantqavirus", J. of Wildlife Diseases, 39(2), 2003, p. 271-277.

Elgh, et al., "Serological Diagnosis Of Hantovirus Infections By an Enzyme-Linked Immunosorbent Assay Based On Detection of Immunoglobulin G and M Responses To Recombinant Nucleocapsid Proteins Of Five Viral Serotypes," *J Clin Microbiol* 35(5):1122-1130 (1997).

Hjelle, et al., "A Novel Hantovirus Associated With An Outbreak Of Fatal Respitory Disease In The Southwestern United States: Evolutionary Relationships To Known Hantoviruses," *J Virol* 68(2):592-596 (1994).

Yamada, et al., "Antobody Responses To Four Corners Hantavirus Infections In The Deer Mouse (*Peromyscus maniculatus*): Identification Of An Immunodominant Region Of The Viral Nucleocapsid Protein," *J Virol* 69(3):1939-1943 (1995).

* cited by examiner

HTNV M Segment

```
   1 tagtagtaga caccgcaaaa gaaagcagtc aatcagcaac atggggatat ggaagtggct
  61 agtgatggcc agtttagtat ggcctgtttt gacactgaga aatgtctatg acatgaaaat
 121 tgagtgcccc catacagtaa gttttgggga aaacagtgtg ataggttatg tagaattacc
 181 ccccgtgcca ttggccgaca cagcacagat ggtgcctgag agttcttgta acatggataa
 241 tcaccaatcg ttgaatacaa taacaaaata tacccaagta agttggagag gaaaggctga
 301 tcagtcacag tctagtcaaa attcatttga gacagtgtcc actgaagttg acttgaaagg
 361 aacatgtgtt ctaaaacaca aaatggtgga agaatcatac cgtagtagga aatcagtaac
 421 ctgttacgac ctgtcttgca atagcactta ctgcaagcca acactataca tgattgtacc
 481 aattcatgca tgcaatatga tgaaagctg tttgattgca ttgggaccat acagagtaca
 541 ggtggtttat gagagaagtt actgtatgac aggagtcctg attaaggga aatgctttgt
 601 cccagatcaa agtgtggtca gtattatcaa gcatgggatc tttgatattg caagtgttca
 661 tattgtatgt ttctttgttg cagttaaagg gaatacttat aaaattttg aacaggttaa
 721 gaaatccttt gaatcaacat gcaatgatac agagaataaa gtgcaaggat attatatttg
 781 tattgtaggg ggaaactctg caccaatata tgttccaaca cttgatgatt tcagatccat
 841 ggaagcattt acaggaatct tcagatcacc acatgggaa gatcatgatc tggctggaga
 901 agaaattgca tcttattcta tagtcggacc tgccaatgca aagttcctc atagtgctag
 961 ctcagataca ttgagcttga ttgcctattc aggtatacca tcttattctt cccttagcat
1021 cctaacaagt tcaacagaag ctaagcatgt attcagccct gggttgttcc caaaacttaa
1081 tcacacaaat tgtgataaaa gtgccatacc actcatatgg actgggatga ttgatttacc
1141 tggatactac gaagctgtcc accttgtac agttttttgc gtattatcag gtcctgggc
1201 atcatgtgaa gcctttctg aaggcgggat tttcaacata acctctccca tgtgcttagt
1261 gtcaaaacaa aatcgattcc ggttaacaga acagcaagtg aattttgtgt gtcagcgagt
1321 ggacatggac attgttgtgt actgcaacgg gcagaggaaa gtaatattaa caaaaactct
1381 agttattgga cagtgtatat atactataac aagcttattc tcattactac ctggagtagc
1441 acattctatt gctgttgaat tgtgtgtacc tgggttccat ggttgggcca cagctgctct
1501 gcttgttaca ttctgtttcg gatgggttct tataccagca attacattta tcatactaac
1561 agtcctaaag ttcattgcta atatttttca cacaagtaat caagagaata ggctaaaatc
1621 agtacttaga aagataaagg aagagtttga aaaaacaaaa ggctcaatgg tatgtgatgt
1681 ctgcaagtat gagtgtgaaa cctataaaga attaaggca cacggggtat catgccccca
1741 atctcaatgt ccttactgtt ttactcattg tgaacccaca gaagcagcat tccaagctca
1801 ttacaaggta tgccaagtta ctcacagatt cagggatgat ctaaagaaaa ctgttactcc
1861 tcaaaatttt acaccaggat gttaccggac actaaattta tttagataca aaagcaggtg
1921 ctacatcttt acaatgtgga tatttcttct tgtcttagaa tccatactgt gggctgcaag
1981 tgcatcagag acaccattaa ctcctgtctg gaatgacaat gcccatgggg taggttctgt
2041 tcctatgcat acagattag agcttgattt ctctttaaca tccagttcca agtatacata
2101 ccgtaggaag ttaacaaacc cacttgagga agcacaatcc attgacctac atattgaaat
2161 agaagaacag acaattggtg ttgatgtgca tgctctagga cactggtttg atggtcgtct
2221 taaccttaaa acatccttc actgttatgg tgcttgtaca agtatgaat acccttggca
2281 tactgcaaag tgccattatg aaagagatta ccaatatgag acgagctggg gttgtaatcc
2341 atcagattgt cctggggtgg gcacaggctg tacagcatgt ggtttatacc tagatcaact
2401 gaaaccagtt ggtagtgctt ataaaattat cacaataagg tacagcagga gagtctgtgt
2461 tcagtttggg gaggaaaacc tttgtaagat aatagacatg aatgattgtt ttgtatctag
2521 gcatgttaag gtctgcataa ttggtacagt atctaaattc tctcagggtg ataccttatt
2581 gttttttgga ccgcttgaag gtggtgtct aatatttaaa cactggtgta catccacatg
2641 tcaatttggt gacccaggag atatcatgag tccaagagac aaaggttttt tatgccctga
2701 gtttccaggt agtttcagga agaaatgcaa ctttgctact accccatttt gtgagtatga
2761 tggaaatatg gtctcaggtt acaagaaagt gatggcgaca attgattcct tccaatcttt
2821 taatacaagc actatgcact tcactgatga aaggatagag tggaaagacc ctgatggaat
2881 gctaagggac catataaaca ttttagtaac gaaggacatt gactttgata accttggtga
2941 aaatccttgc aaaattggcc tacaaacatc ttctattgag ggggctggg gttctggtgt
3001 ggggttcaca ttaacatgtc tggtatcact aacagaatgt cctaccttt tgacctcaat
3061 aaaggcttgt gataaggcta tctgttatgg tgcagagagt gtaacattga aagaggaca
3121 aaatacagtc aaggtatcag ggaaggtgg ccatagtggt tcaacattta ggtgttgcca
3181 tggggaggac tgttcacaaa ttggactcca tgctgctgca cctcaccttg acaaggtaaa
3241 tgggatttct gagatagaaa atagtaaagt atatgatgat ggggcaccgc aatgtgggat
3301 aaaatgttgg tttgttaaat cagggaatg gatttcaggg atattcagtg taattggat
3361 tgtactcatt gtcctctgtg tatttctatt gttctccttg gttttactaa gcattctctg
3421 tccccgtaagg aagcataaaa aatcatagct aaattctgtg actatcctgt tcttatgtat
3481 agctttaaca tatatactaa tttttatatt ccagtatact ctatctaaca cactaaaaaa
3541 aatagtagct ttctaaccac aaaacttaga ttcttcttct gtatgatgtc ttaacatctt
3601 gcggtgtcta ctacta
```

FIGURE 1A (SEQ ID NO:1)

```
   1 MGIWKWLVMA SLVWPVLTLR NVYDMKIECP HTVSFGENSV IGYVELPPVP LADTAQMVPE
  61 SSCNMDNHQS LNTITKYTQV SWRGKADQSQ SSQNSFETVS TEVDLKGTCV LKHKMVEESY
 121 RSRKSVTCYD LSCNSTYCKP TLYMIVPIHA CNMMKSCLIA LGPYRVQVVY ERSYCMTGVL
 181 IEGKCFVPDQ SVVSIIKHGI FDIASVHIVC FFVAVKGNTY KIFEQVKKSF ESTCNDTENK
 241 VQGYYICIVG GNSAPIYVPT LDDFRSMEAF TGIFRSPHGE DHDLAGEEIA SYSIVGPANA
 301 KVPHSASSDT LSLIAYSGIP SYSSLSILTS STEAKHVFSP GLFPKLNHTN CDKSAIPLIW
 361 TGMIDLPGYY EAVHPCTVFC VLSGPGASCE AFSEGGIFNI TSPMCLVSKQ NRFRLTEQQV
 421 NFVCQRVDMD IVVYCNGQRK VILTKTLVIG QCIYTITSLF SLLPGVAHSI AVELCVPGFH
 481 GWATAALLVT FCFGWVLIPA ITFIILTVLK FIANIFHTSN QENRLKSVLR KIKEEFEKTK
 541 GSMVCDVCKY ECETYKELKA HGVSCPQSQC PYCFTHCEPT EAAFQAHYKV CQVTHRFRDD
 601 LKKTVTPQNF TPGCYRTLNL FRYKSRCYIF TMWIFLLVLE SILWAASASE TPLTPVWNDN
 661 AHGVGSVPMH TDLELDFSLT SSSKYTYRRK LTNPLEEAQS IDLHIEIEEQ TIGVDVHALG
 721 HWFDGRLNLK TSFHCYGACT KYEYPWHTAK CHYERDYQYE TSWGCNPSDC PGVGTGCTAC
 781 GLYLDQLKPV GSAYKIITIR YSRRVCVQFG EENLCKIIDM NDCFVSRHVK VCIIGTVSKF
 841 SQGDTLLFFG PLEGGGLIFK HWCTSTCQFG DPGDIMSPRD KGFLCPEFPG SFRKKCNFAT
 901 TPICEYDGNM VSGYKKVMAT IDSFQSFNTS TMHFTDERIE WKDPDGMLRD HINILVTKDI
 961 DFDNLGENPC KIGLQTSSIE GAWGSGVGFT LTCLVSLTEC PTFLTSIKAC DKAICYGAES
1021 VTLTRGQNTV KVSGKGGHSG STFRCCHGED CSQIGLHAAA PHLDKVNGIS EIENSKVYDD
1081 GAPQCGIKCW FVKSGEWISG IFSGNWIVLI VLCVFLLFSL VLLSILCPVR KHKKS
```

FIGURE 1B (SEQ ID NO:2)

PUUV M SEGMENT

```
   1 tagtagtaga ctccgcaaga agaagcaaac acagatcaat atgggagaac ttagtccagt
  61 ttgtctgtat ctgcttctcc agggtctatt actatgtaat acaggggctg ccagaaacct
 121 taatgagctt aaaatggaat gtccacatac tattagatta gggcagggtc ttgttgtggg
 181 ttcagtagaa ttgccatctc ttccaataca gcaggtcgag acactaaagc tggagagttc
 241 ttgtaatttt gatctacata ccagtacagc aggacaacaa tcattcacaa aatggacatg
 301 ggaaattaaa ggtgatcttg cagagaacac acaggcatca tcaacaagtt ttcaaacaaa
 361 aagcagtgaa gtgaatttga gaggattatg tttgatccct actttagtgg ttgaaacagc
 421 agcaagaatg cgaaaaacaa tagcatgtta tgacctgtca tgcaatcaaa cagtgtgtca
 481 gcctactgtc tatttaatgg gacctatcca gacttgtata caactaaaa gttgtctctt
 541 gagtttaggt gatcaaagga ttcaagtaaa ttatgaaaaa acatactgtg tttctgggga
 601 ccttgttgaa ggtatctgtt ttaatccaat acatacaatg gcactctctc aacctagtca
 661 tacatatgat ataatgacca tgatggttcg ctgtttcttg gtaataaaga aagtgacttc
 721 tggtgacagt atgaagattg aaaagaactt tgagactctt gttcaaaaaa atggctgcac
 781 agctaataac ttccaagggt attatatctg tcttataggg agtagttcag agcccttata
 841 tgttccagca ttagatgatt atcgttcagc tgaagttctt tcaaggatgg catttgcacc
 901 acatggtgaa gatcatgata ttgagaaaaa tgcagtgagt gcaatgcgta ttgctggaaa
 961 ggtgacagga aaggtgccat caacagaatc atcagataca gtacagggga ttgcattttc
1021 aggtagtcct ctttatacat ctactggtgt cttgacatca aaagatgatc ctgtctacat
1081 ttgggctcct ggaatcataa tggaaggaaa ccattctatt tgtgaaaaga agaccttacc
1141 ccttacatgg actggtttta tttcattgcc tggagagatt gaaaaaacaa cacaatgtac
1201 agtatttgt acattggctg gaccaggtgc agattgtgaa gcttactctg aaacaggcat
1261 cttcaacata agttcaccta cttgcttaat aaatcgtgtc cagagattcc gtggttcaga
1321 acagcaaata aagtttgtgt gccagagagt ggacatggat atcactgttt actgtaatgg
1381 gatgaagaaa gtcattctca ccaagaccct agttattgga caatgcattt atacttttac
1441 tagtattttc tctctaatcc ctggtgttgc acattccctt gctgttgaat tatgtgtacc
1501 tggtcttcat ggttgggcaa ctatgctatt attactaaca ttttgttttg gctgggtctt
1561 aataccaact ataacaatga tcctgctaaa gatattgatt gcattcgcat acttatgttc
1621 taaatataac acagattcga aattcaggat cttgattgag aaagtgaaaa gagagtacca
1681 gaaaacaatg ggttcaatgg tttgtgaagt gtgtcagtat gaatgtgaga ctgcaaaaga
1741 actggagtca catagaaaga gttgttccat tggttcatgc cctattgtc tcaatccatc
1801 tgaggcaaca acatctgccc ttcaggctca ttttaaagtg tgtaagctca gatcacgtt
1861 tcaggagaat ttaagaaagt cattaacggt atatgagcct atgcaagggt gctaccggac
1921 tttatccctc tttagatata ggagtcggtt ctttgtgggt ctagtctggt gcgtgttatt
1981 ggttcatcac ttaattgtat gggctgccag tgctgaaaca caaaatttaa atgcaggttg
2041 gacagacaca gcacatggat ctagaattat acctatgaaa actgatctgg aattagactt
2101 ctctcttcag tcatcagcaa gctatacata taggagacag ctacaaaacc cagcaaacga
2161 acaagagaaa atcccatttc atctgcagtt aagcaaacaa gtgattcatg cagagatcca
2221 gcatttaggt cattggatgg atgctacatt taatcttaaa actgcatttc actgctatgg
2281 ctcatgtgag aagtatgctt atccttggca gacagcaggt tgtttcatag aaaaagatta
2341 tgaatatgag actggttggg gttgtaatcc acctgattgc ccaggggtag ggacaggctg
2401 tactgcttgt ggggtatacc ttgataaatt aaaatcagtt ggaaaggttt tcaaaattgt
2461 gtccttaaga tacacaagga agtatgcat tcagttgggc acagaacaaa catgtaagac
2521 tgttgatagt aatgactgtc tcattaccac ttcagttaaa gtgtgcttga tagggaccat
2581 atcaaaattc caaccatctg acactttgct atttctaggt ccactacagc agggtggtct
2641 gatatttaaa caatggtgca ctacaacatg ccagtttggc gatcccgggg acataatgag
2701 cacacctaca ggcatgaagt gcccagaatt aaatggttct tttagaaaga aatgtgcatt
2761 tgcaacaac ccagtttgcc agtttgatgg aaataacaatt tcaggctata agaggatgat
2821 tgccacaaag gattcatttc aatctttcaa tgtgacagaa ccccatattt ctacaagtgc
2881 acttgaatgg attgatcctg acagctcact tagggaccat attaatgtaa ttgtgagtcg
2941 tgatctatcc ttccaagacc taagtgaaac accatgtcaa attgatttag caacagcctc
3001 tatagatgga gcatggggtt caggagttgg ttttaatctg gtttgtactg ttagtttaac
3061 agaatgttct gcatttctga catcaatcaa ggcctgtgat gctgcaatgt gttatgggtc
3121 caccacagcc aatctagttc gagggcaaaa taccattcat atcgtcggta agggtgggca
3181 ttctggttca aaatttatgt gttgtcatga cacaaaaatgt tctagcaccg gtctagttgc
3241 agctgcacca cacttagatc gtgtgacacc atacaatcag gctgatagtg acaaaatctt
3301 tgatgatggg gcaccagaat gatggtggtt atgttggttt aaaaaatcag tgaatgatgg
3361 tcttggggtt ttgaacggga attgatggt tgttgctgta ctggtagtat tactgatctt
3421 gtccatactc ttattcacat tatgttgtcc tcgtagacct agttacagga agaacataa
3481 gccctaagtt ttgcttacta acataattat tgtattctgt ttattgacac aattaccata
3541 tgattaactg tattccccca tcttatatct tatataatat tcttttattta atcactatat
3601 agaaaaaaaa ctagcacttt actaattaaa ttaccccata ccgattatgc ctggactttt
3661 gttcttgcgg agtctactac ta
```

FIGURE 2A (SEQ ID NO:3)

```
   1 MGELSPVCLY LLLQGLLLCN TGAARNLNEL KMECPHTIRL GQGLVVGSVE LPSLPIQQVE
  61 TLKLESSCNF DLHTSTAGQQ SFTKWTWEIK GDLAENTQAS STSFQTKSSE VNLRGLCLIP
 121 TLVVETAARM RKTIACYDLS CNQTVCQPTV YLMGPIQTCI TTKSCLLSLG DQRIQVNYEK
 181 TYCVSGDLVE GICFNPIHTM ALSQPSHTYD IMTMMVRCFL VIKKVTSGDS MKIEKNFETL
 241 VQKNGCTANN FQGYYICLIG SSSEPLYVPA LDDYRSAEVL SRMAFAPHGE DHDIEKNAVS
 301 AMRIAGKVTG KVPSTESSDT VQGIAFSGSP LYTSTGVLTS KDDPVYIWAP GIIMEGNHSI
 361 CEKKTLPLTW TGFISLPGEI EKTTQCTVFC TLAGPGADCE AYSETGIFNI SSPTCLINRV
 421 QRFRGSEQQI KFVCQRVDMD ITVYCNGMKK VILTKTLVIG QCIYTFTSIF SLIPGVAHSL
 481 AVELCVPGLH GWATMLLLLT FCFGWVLIPT ITMILLKILI AFAYLCSKYN TDSKFRILIE
 541 KVKREYQKTM GSMVCEVCQY ECETAKELES HRKSCSIGSC PYCLNPSEAT TSALQAHFKV
 601 CKLRSRFQEN LRKSLTVYEP MQGCYRTLSL FRYRSRFFVG LVWCVLLVHH LIVWAASAET
 661 QNLNAGWTDT AHGSRIIPMK TDLELDFSLQ SSASYTYRRQ LQNPANEQEK IPFHLQLSKQ
 721 VIHAEIQHLG HWMDATFNLK TAFHCYGSCE KYAYPWQTAG CFIEKDYEYE TGWGCNPPDC
 781 PGVGTGCTAC GVYLDKLKSV GKVFKIVSLR YTRKVCIQLG TEQTCKTVDS NDCLITTSVK
 841 VCLIGTISKF QPSDTLLFLG PLQQGGLIFK QWCTTTCQFG DPGDIMSTPT GMKCPELNGS
 901 FRKKCAFATT PVCQFDGNTI SGYKRMIATK DSFQSFNVTE PHISTSALEW IDPDSSLRDH
 961 INVIVSRDLS FQDLSETPCQ IDLATASIDG AWGSGVGFNL VCTVSLTECS AFLTSIKACD
1021 AAMCYGSTTA NLVRGQNTIH IVGKGGHSGS KFMCCHDTKC SSTGLVAAAP HLDRVTPYNQ
1081 ADSDKIFDDG APECGMSCWF KKSGEWILGV LNGNWMVVAV LVVLLILSIL LFTLCCPRRP
1141 SYRKEHKP
```

FIGURE 2B (SEQ ID NO:4)

SEOV M SEGMENT

```
   1 tagtagtaga ctccgcaaga aacagcagtt aaataacagc aggatcatgt ggagtttgct
  61 attactggcc gctttagttg gccaaggctt tgcattaaaa aatgtgtttg acatgagaat
 121 tcagtgcccc cactcagtca aatttgggga aacaagtgtg tcaggctaca cagaactgcc
 181 cccactctca ttacaggagg cagaacagct ggtgccagag agctcatgca acatggacaa
 241 ccaccaatca ctctcaacaa taaataaatt aaccaaggtc atatggcgga aaaaggcaaa
 301 tcaggaatca gcaaaccaga attcatttga acttatggag agtgaagtca gctttaaagg
 361 gttgtgtatg ttaaagcata gaatggttga agaatcctac agaaatagga gatcagtaat
 421 ctgttatgat ctagcctgta atagtacatt ctgtaagcca actgtctaca tgattgttcc
 481 tatacatgca tgcaacatga tgaaagctg tttgattggt cttggtcctt acagagtcca
 541 ggtcgtttat gaaaggacat actgcactac gggtatattg acagaaggaa aatgctttgt
 601 tcctgacaag gctgtcgtca gtgcattgaa gagaggcatg tacgccatag caagcataga
 661 gacaatctgc ttttttattc atcagaaagg gaatacatat aagatagtga ctgccatcac
 721 atcggcaatg ggctccaaat gtaataatac agatactaaa gttcaagggt attatatctg
 781 tattattggt gggaactctg cccccgtata tgcccctgct ggtgaagact ttagggcaat
 841 ggaggttttt tccgggatta ttacatcacc gcatggagaa gaccatgatc tccctggcga
 901 agaaattgca acataccaga tttcagggca gatagaggca aaaatccctc atacagtgag
 961 ctccaagaac ttaaaattga ctgcttttgc aggtattcca tcatactcat caaccagtat
1021 attgactgct tcagaagatg gtcgtttcat atttagtcct ggtctatttc ctaaacctaaa
1081 tcagtcagtc tgtgacaaca atgcactccc tttaatctgg aggggcctaa ttgatttaac
1141 aggatactat gaggcagtcc acccttgcaa tgtattctgt gtcttatcag gaccaggtgc
1201 ttcatgtgaa gccttttcag aaggaggtat tttcaatatt acttccccaa tgtgtcttgt
1261 gtccaagcaa aataggttta gagcagctga gcagcagatc agctttgttt gccaaagggt
1321 tgatatggat attatagtgt actgtaatgg tcagaaaaag acaatcctaa caaaaacatt
1381 agttataggc caatgcattt atactattac aagtctcttt tcactgttac caggggttgc
1441 ccattctatt gctattgagt tgtgtgttcc aggatttcat ggctgggcca cagctgcact
1501 tttgatcaca ttctgctttg gctgggtatt gattcctgca tgtacattag ctattctttt
1561 agttcttaag ttttttgcaa atatcctcca cacaagcaat caagagaacc gattcaaagc
1621 cattctacgg aaaataaagg aggagtttga aaaacaaag ggttccatgg tttgtgagat
1681 ctgtaagtac gagtgtgaaa cattaaagga attgaaggca cataatctat catgtgttca
1741 aggggaatgc ccatattgct ttacccactg tgaaccgaca gaaactgcaa ttcaggcaca
1801 ttacaaagtt tgtcaagcca cccaccgatt cagagaagat ttaaaaaaga ctgtgactcc
1861 tcaaaatatt gggcctggtt gttaccgaac attaaatctt tttaggtata aaagtaggtg
1921 ttatattctg acaatgtgga ctcttcttct cattattgaa tccattctct gggcagcaag
1981 tgcagcagaa atcccccttg tccctctctg gacagataat gctcatggtg ttgggagtgt
2041 tcctatgcat acagaccttg aattagactt ttctttgcca tctagttcta ggtacacata
2101 taaaagacat ctcacaaacc cagttaatga ccaacagagt gtctcattgc acatagaaat
2161 tgaaagtcaa ggcattggtg ctgatgtcca tcatcttgga cattggtatg atgcaagatt
2221 gaatttaaaa acctcatttc attgttatgg tgcctgcaca aaatatcaat atccatggca
2281 cactgcaaaa tgccatttg agaaagatta tgagtataga aatagctggg catgcaaccc
2341 cccagattgc ccaggggttg gtacaggttg tactgcttgt ggttatatc tcgatcaatt
2401 gaagccggta ggaacagcct ttaaaattat aagtgtaaga tacagtagaa aagtgtgcgt
2461 gcagtttggt gaagagtacc tttgtaaaac aattgtatg aacgattgct ttgtgactag
2521 gcatgccaaa atatgtataa ttgggactgt atctaagttt tctcaaggtc acactctact
2581 atttctgggg cccatggaag gaggtggtat aatctttaaa cactggtgca cgtctacctg
2641 tcactttgga gaccctggtg atgtcatggg tccaaaggat aaaccattta tttgccctga
2701 attcccaggg caattcagga aaaatgtaa ctttgccaca actccagttt gtgaatatga
2761 tgggaatatt atctcaggct ataagaaagt tcttgcaaca attgtcttct tccaatcatt
2821 taacacaagc aatatacact tcactgatga gagaattgaa tggagagacc ctgatggtat
2881 gcttcgggat catattaata tcgttatttc taaagatatt gattttgaaa atttggctga
2941 gaatccttgt aaagtagggc tccaggcagc aaacatagaa ggtgcctggg gttcaggtgt
3001 cgggtttaca ctcacatgcc aggtgtctct cacagaatgc ccaacatttc tcacgtcaat
3061 aagggcctgt gacatggcaa tttgttatgg tgcagaaagt gtgacactct cacgaggaca
3121 aaatactgtc aaaattaccg ggaaggtgg ccatagtggt tcctcattta agtgctgtca
3181 tgggaaagaa tgttcattaa ctggcctcca agccagtgca ccacatttag ataaggtaaa
3241 tggaatctct gagttagaaa atgagaaagt ttatgatgat ggtgcacctg aatgtggcat
3301 tacttgttgg tttaaaaat caggtgaatg ggtttatggt ataatcaatg gaactgggt
3361 tgtcctaatt gtcttgtgtg tcctgctgct cttttctctt atcctgttga gcatcctgtg
3421 tcctgttaga aagcataaaa aatcataaat cctgcttatt aatcttcata gcatgtatcg
3481 agttttaaac actttaccat taaaaactta acctggctct aatatctgat aactaacttt
3541 catttttatt tttatatgga ttaattacta aaaaaaatac tctcttctat ctcccaatct
3601 tttattgatt caccggggtg ttgtcttgac atcttgcgga gtctactact a
```

FIGURE 3A (SEQ ID NO:5)

```
   1 MWSLLLLAAL VGQGFALKNV FDMRIQCPHS VKFGETSVSG YTELPPLSLQ EAEQLVPESS
  61 CNMDNHQSLS TINKLTKVIW RKKANQESAN QNSFELMESE VSFKGLCMLK HRMVEESYRN
 121 RRSVICYDLA CNSTFCKPTV YMIVPIHACN MMKSCLIGLG PYRVQVVYER TYCTTGILTE
 181 GKCFVPDKAV VSALKRGMYA IASIETICFF IHQKGNTYKI VTAITSAMGS KCNNTDTKVQ
 241 GYYICIIGGN SAPVYAPAGE DFRAMEVFSG IITSPHGEDH DLPGEEIATY QISGQIEAKI
 301 PHTVSSKNLK LTAFAGIPSY SSTSILTASE DGRFIFSPGL FPNLNQSVCD NNALPLIWRG
 361 LIDLTGYYEA VHPCNVFCVL SGPGASCEAF SEGGIFNITS PMCLVSKQNR FRAAEQQISF
 421 VCQRVDMDII VYCNGQKKTI LTKTLVIGQC IYTITSLFSL LPGVAHSIAI ELCVPGFHGW
 481 ATAALLITFC FGWVLIPACT LAILLVLKFF ANILHTSNQE NRFKAILRKI KEEFEKTKGS
 541 MVCEICKYEC ETLKELKAHN LSCVQGECPY CFTHCEPTET AIQAHYKVCQ ATHRFREDLK
 601 KTVTPQNIGP GCYRTLNLFR YKSRCYILTM WTLLLIIESI LWAASAAEIP LVPLWTDNAH
 661 GVGSVPMHTD LELDFSLPSS SRYTYKRHLT NPVNDQQSVS LHIEIESQGI GADVHHLGHW
 721 YDARLNLKTS FHCYGACTKY QYPWHTAKCH FEKDYEYENS WACNPPDCPG VGTGCTACGL
 781 YLDQLKPVGT AFKIISVRYS RKVCVQFGEE YLCKTIDMND CFVTRHAKIC IIGTVSKFSQ
 841 GDTLLFLGPM EGGGIIFKHW CTSTCHFGDP GDVMGPKDKP FICPEFPGQF RKKCNFATTP
 901 VCEYDGNIIS GYKKVLATID SFQSFNTSNI HFTDERIEWR DPDGMLRDHI NIVISKDIDF
 961 ENLAENPCKV GLQAANIEGA WGSGVGFTLT CQVSLTECPT FLTSIRACDM AICYGAESVT
1021 LSRGQNTVKI TGKGGHSGSS FKCCHGKECS LTGLQASAPH LDKVNGISEL ENEKVYDDGA
1081 PECGITCWFK KSGEWVMGII NGNWVVLIVL CVLLLFSLIL LSILCPVRKH KKS
```

FIGURE 3B (SEQ ID NO:6)

DOBV M SEGMENT

```
   1 tagtagtaga ctccgcaaga aacagcagtt aaataacagc atgatcatgt ggggtctact
  61 attgacaatg attttgatcg attttggggc atccttaagg aatgtttatg acatgaagat
 121 agaatgccca cattcaatca actttgggga gagcagtgta acaggtaagg tggaattacc
 181 acccctttctg ctcacagatg cagaggcctt ggtcccggag agttcttgta acatggacaa
 241 ccatcagtct atgtcaatta tacaaaaagt gacaaaagtg agttggagaa aaaaggcaga
 301 caaagcccaa gctgccaagg actcatttga dacaacatca agcgaggtta atctgaaggg
 361 gacatgcaca ttgagtcata ggatggttga agaatcctac aggaataggga gatcagtgat
 421 atgctatgac ttgtcttgca attcaacaca ttgtaagcca acgatgcata tgattgtgcc
 481 tgtgcactca tgcaacatga tgaaaagctg tctggttggg cttgggcctt atcgaatcca
 541 agttgtctat gaaagaacct actgtacaac tggtatacta acagaaggga agtgttttgt
 601 gccagaccag agtattgtca gtgtcatcaa gaatggggtt tttgacattg caagtgtgag
 661 cattgtctgt tttttttatca gagttaaagg aactaactac aagataatgg cgagtattaa
 721 aacagcaact gcaaataact gtaatgacac tgacaataag gttcaaggat attacctttg
 781 tattgttggg ggaaattctt ctcctgtgta tgcaccttca accactgatt ttagatctat
 841 ggaagcactt gctagccttt taagagctcc tcatggtgag gaccatgatt tatctggaga
 901 agaggttgca acttattcaa ttgccgggca aattgaaggc aaaatcccac atactgcaaa
 961 tgcagcaaac atgctattta ctgcattctc aggaattcct agttactctt cattgagtgt
1021 ttttattgga agtcaagatg ggcctattat ttatagccca ggattgtttc ccaagttgaa
1081 ccaatcttca tgtgataagg tcgcactacc attgatatgg gaagggtaca tagatctacc
1141 tggctattat gaaacagttc accgtgtaa tgtcttttgt gtgctatctg gcccaggagc
1201 atcatgtgag gcattctcag aaggtggtat tttcaatatt catcccca catgccttgt
1261 gtcaaagcaa aatcggttca gggcagctga gcagcaagtc aatttcgtat gccagcgagt
1321 cgaccaagac attattatct actgtaatgg acaaaagaag acaattttga ccaagacatt
1381 agtgattggg cagtgtattt attcagtgac tagtttgttt tcaataatgc ctggggtagc
1441 acattcaatt gcaatcgaat tatgtgtacc agggtccat ggctgggcaa ctgctgctct
1501 tctcaccaca ttctgctttg gctggatact gatcccttcc atcacattgg ctgtattggt
1561 tgtcttaaag ttttttgcag caatcttaca taatagctct caagaaaacc gttttaaaat
1621 tatcctaagg aagattaaag aagaatttga aagactaag ggctcaatgg tttgtgaagt
1681 gtgcaagtat gagtgtgaaa cagggaagga gcttaaagcc cataatttgt cttgccctca
1741 gtcacagtgt ccttattgct ttacacattg tgagcctaca gaatctgcct tccaggcaca
1801 ttataaagtg tgccaggcaa cacacaggtt tagagatgat ttgaagaaaa caataacacc
1861 tcaatctaca agcccgggtt gttaccggac attaaatctc tttaggtata aaagtaggtg
1921 ttacattttt acagtgtggg tcaccctgct aatcattgaa tcaatcagtt gggcagctag
1981 cgcatcagaa aatgttttgg agccaagctg gaatgacaac gcacatggtg ttggtgttgt
2041 cccaatgcat actgatctgg aactagattt ttctcttccg tcaagttcta agtacacata
2101 taaagaaaaa ctgacaagtc cattaaatca agaacaatca gtagatcttc acatagagat
2161 agagagtcaa gggattctca caagtgttca tgcattaggt cattggtttg atgggagact
2221 taattaaaag acatctttcc attgttatgg tgcatgtact aagtatgaat atccttggca
2281 tacagcaaaa tgccactttg aaagggattt cgagtatgag aacagctggg gctgtaatcc
2341 tgctgattgc cctgggattg gtacggctg tactgcatgc ggactataca ttgaccaact
2401 taaacctgta ggcagtgcat acaagctaat cacagtccgt tacagccgta aagtatgtgt
2461 tcagtttggt gaagaaaacc tatgtaagac aattgacatg aatgattgct ttgttacaag
2521 acatgtcaaa gtatgcatta taggtacagt ttcaaagttc tcacaaggtg ataccctagt
2581 attcctgggc cctatggaag gtggggcctt aatatttaag gattggtgca ctagcacatg
2641 ccaatttggt gatcctgggg acattatgag tcctaaagac aaagggttta gctgccctga
2701 cttcacaggc cacttccgga aaaatgcaa ctttgcaaca cacctgtat gcgagtatga
2761 tggtaatatg gtctctaggt ataagaaagt aatggcaact attgattcct ttcagtcatt
2821 taacactagc tcaattcatt acacagatga aaggattgaa cggaaggacc ctgatgggat
2881 gcttaaggac catctcaata tacttgtcac aaaagacatt gactttgaaa accttgggga
2941 gaacccgtgc aaagtagggc ttcaaacatc atcaatagaa ggtgcatggg gctctgggt
3001 tggtttcacc cttacttgtc aaatctcact gacagaatgt tctcgctttc tgacatccat
3061 taaagcatgt gacatggcaa tctgttatgg tgcacaaagt gtcacactca ttagaggcca
3121 aaatacagtg aaggtttccg ggaagggtgg gcatagtggc tcttcattca agtgttgtca
3181 agggacagat tgctctcagc aggggctaca agcaagcgca ccacacctag acaaagtcaa
3241 tggaattgtt gaacaagata tgaaaaagt ctatgatgat ggtgcaccac aatgtggcat
3301 ttcatgctgg tttgttaagt ctggggagtg gataacagga atctttaatg gaactggat
3361 tgtcattgtt gtgcttgttt tcttcatact atcctaatc ttacttagtc ttttatgccc
3421 cattcgtaag cataagcgct cataagtaaa tactagagaa acctattagc atgtccctat
3481 atatagcctt taacaatgca attttatata tcagtttaaa cttctgtact tattaatttt
3541 ttacatttat taacctagtt atctaaaaaa aataactcct tcattactat aaatcttagt
3601 ccttagtatg tgggtatttc tatatcttgc ggagtctact acta
```

FIGURE 4A (SEQ ID NO:7)

```
   1  MIMWGLLLTM  ILIDFGASLR  NVYDMKIECP  HSINFGESSV  TGKVELPPLL  LTDAEALVPE
  61  SSCNMDNHQS  MSIIQKVTKV  SWRKKADKAQ  AAKDSFETTS  SEVNLKGTCT  LSHRMVEESY
 121  RNRRSVICYD  LSCNSTHCKP  TMHMIVPVHS  CNMMKSCLVG  LGPYRIQVVY  ERTYCTTGIL
 181  TEGKCFVPDQ  SIVSVIKNGV  FDIASVSIVC  FFIRVKGTNY  KIMASIKTAT  ANNCNDTDNK
 241  VQGYYLCIVG  GNSSPVYAPS  TTDFRSMEAL  ASLLRAPHGE  DHDLSGEEVA  TYSIAGQIEG
 301  KIPHTANAAN  MLFTAFSGIP  SYSSLSVFIG  SQDGPIIYSP  GLFPKLNQSS  CDKVALPLIW
 361  EGYIDLPGYY  ETVHPCNVFC  VLSGPGASCE  AFSEGGIFNI  TSPTCLVSKQ  NRFRAAEQQV
 421  NFVCQRVDQD  IIIYCNGQKK  TILTKTLVIG  QCIYSVTSLF  SIMPGVAHSI  AIELCVPGFH
 481  GWATAALLTT  FCFGWILIPS  ITLAVLVVLK  FFAAILHNSS  QENRFKIILR  KIKEEFEKTK
 541  GSMVCEVCKY  ECETGKELKA  HNLSCPQSQC  PYCFTHCEPT  ESAFQAHYKV  CQATHRFRDD
 601  LKKTITPQST  SPGCYRTLNL  FRYKSRCYIF  TVWVTLLIIE  SIMWAASASE  NVLEPSWNDN
 661  AHGVGVVPMH  TDLELDFSLP  SSSKYTYKRK  LTSPLNQEQS  VDLHIEIESQ  GISTSVHALG
 721  HWFDGRLNLK  TSFHCYGACT  KYEYPWHTAK  CHFERDFEYE  NSWGCNPADC  PGIGTGCTAC
 781  GLYIDQLKPV  GSAYKLITVR  YSRKVCVQFG  EENLCKTIDM  NDCFVTRHVK  VCIIGTVSKF
 841  SQGDTLVFLG  PMEGGGLIFK  DWCTSTCQFG  DPGDIMSPKD  KGFSCPDFTG  HFRKKCNFAT
 901  TPVCEYDGNM  VSRYKKVMAT  IDSFQSFNTS  SIHYTDERIE  RKDPDGMLKD  HLNILVTKDI
 961  DFENLGENPC  KVGLQTSSIE  GAWGSGVGFT  LTCQISLTEC  SRFLTSIKAC  DMAICYGAQS
1021  VTLIRGQNTV  KVSGKGGHSG  SSFKCCQGTD  CSQQGLQASA  PHLDKVNGIV  EQDSEKVYDD
1081  GAPQCGISCW  FVKSGEWITG  IFNGNWIVIV  VLVFFILSLI  LLSLLCPIRK  HKRS
```

FIGURE 4B (SEQ ID NO:8)

SNV M SEGMENT

```
   1 tagtagtaga ctccgcacga agaagcaaac actgaataaa ggagatacag aatggtaggg
  61 tgggtttgca tcttcctcgt ggtccttact actgcaactg ctgggctaac acggaatctt
 121 tatgagttga agatagaatg tccacatact gtgggtttag gtcagggtta cgtgacaggt
 181 tcagtggaaa ttacacctat tctcttaacg caggtagctg atctgaagat tgagagttct
 241 tgtaatttcg atttgcatgt cccggctacc actacccaaa aatacaatca ggttgactgg
 301 accaaaaaaa gttcaactac agaaagcaca aatgcaggtg caactacatt tgaggctaaa
 361 acaaaagaga taaatttgaa aggcacatgt aatattcctc caactacatt tgaagctgca
 421 tataaatcaa ggaagacagt aatttgttat gatttagcct gtaatcaaac acattgtctt
 481 cctacggtcc atttgattgc tcctgttcaa acgtgcatgt ctgtgcgagg ctgtatgata
 541 ggtttgctgt caagcaggat tcaagtgata tatgagaaga catactgcgt tacaggtcaa
 601 ttaatagagg ggctatgttt catcccaaca catacaattg cactcacaca acctggtcat
 661 acctatgata ctatgacatt gccagtgact tgttttttag tagctaaaaa gttgggaaca
 721 cagcttaagc tggctgttga gttagagaaa ctgattactg gtgtaagttg cacagaaaac
 781 agctttcaag gttactacat ctgttttatc gggaaacatt cagagcccctt atttgtgcca
 841 acaatggagg attataggtc agctgagtta tttacccgta tggttttaaa tccgagaggt
 901 gaagatcatg accctgatca aaatggacaa ggtttaatga gaatagctgg gcctgttaca
 961 gctaaggtgc catctacaga aacaactgaa acaatgcaag gaattgcatt tgctggagca
1021 ccaatgtata gctctttctc aaccctcgtg aggaaggctg atcctgagta tgtcttctca
1081 ccaggtataa ttgcagaatc aaatcatagt gtttgtgata aaaaaacagt accccttaca
1141 tggacagggt ttttggcagt ttctggagag atagagaaaa taacaggctg tacagtcttc
1201 tgtacattgg ctggacctgg tgctagttgt gaagcatact cagaaacagg aatctttaat
1261 ataagttctc ctacttgtct agtgaataaa gttcaaaaat tcagaggctc agaacagagg
1321 attaacttca tgtgccaaag agttgatcaa gatgtagttg tctattgtaa tggacaaaag
1381 aaagtcattc ttaccaaaac tctggtcata ggccaatgca tttatacatt cactagttta
1441 ttctcactaa tcccaggagt tgcccattct cttgctgtag agctatgtgt tccaggcctt
1501 catggctggg ctacaacggc attactgatt acttttttgct ttggctggct ccttataccg
1561 gcagtcacct taattatact gaagttgctg aagttgctca cttttctcatg ctcacattat
1621 tccacagaat caaaattcaa agttatctta gaaaggggtta aggttgaata tcagaaaaca
1681 atgggctcta tggtgtgtga tatttgccac cacgaatgcg aaacagcaaa agaacttgaa
1741 acacataaga aaagctgtcc agaaggtcaa tgcccgtatt gtatgacaat aactgaatcc
1801 actgagagtg ctctccaagc ccattttgca atctgtaagc taacaaacag gtttcaggaa
1861 aacttaaaaa agtcattgaa acgcccagaa gtacggaaag gttgttacag gacactggga
1921 gtttttagat acaagagcag atgttatgtt ggtttagtat ggggaattct tttaacaact
1981 gaactgatca tatgggcagc cagtgcagac acccctttaa tggagtctgg ttggtctgac
2041 acagcacatg gtgtgggcat aattcctaca tggagcttga ttttgcattg
2101 gcctcatcat cttcttacag ttataggcga aagcttgtta atcctgctaa tcaagaagaa
2161 acactccctt ttcatttcca gttagataaa caagtagtgc atgcagagat ccagaaccta
2221 ggacattgga tggatggcac attcaacata aaaactgctt tcactgtta tggggagtgt
2281 aaaaaatatg cctatccttg gcaaacagcc aagtgtttct ttgaaaagga ttatcaatat
2341 gaaacaagtt ggggctgtaa tccaccagac tgtccagggg taggtacagg ttgtacagct
2401 tgtggggtgt accttgataa gctccgttcg gttgggaaag cgtacaagat agtatcactc
2461 aaatatacac ggaaggtgtg tattcaatta gaaacttgtaa acatatagat
2521 gtaaatgatt gcctggttac cccttctgtc aaagtttgta tgattggtac tatatcaaag
2581 ctccagccag gtgatacctt gttgttctta ggtcctttag agcagggtgg gatcattctt
2641 aagcaatggt gtacaacatc atgtgtgttt ggagatcccg tgatatttat gtcaacaaca
2701 agtgggatgc ggtgcccaga acatactgga tcttttagaa agatctgtgg gttttgctacg
2761 acaccaacat gtgagtatca aggcaacaca gtgtctggat tccaacgcat gatggcaact
2821 cgagattctt tccagtcatt caatgtgaca gaaccacata tcactagcaa ccgacttgag
2881 tggattgatc cagatagcag tatcaaagat cacattaata tggttttaaa tcgagatgtt
2941 tcctttcagg atctaagtga taacccatgc aaggttgacc tgcatacaca atcaattgac
3001 ggggcctggg gttcaggagt aggttttacg ttggtatgta ctgtggggct tacagagtgt
3061 gcaaatttta aacttcaat taaagcatgt gattctgcca tgtgttatgg agccacagtg
3121 acaaatctgc ttagagggtc taacacagtt aaagttgttg gtaaaggtgg gcattctgga
3181 tctttgtttta aatgctgcca tgatactgac tgtaccgaag aagggttagc agcatctcca
3241 ccacatttag acaggggtac aggctataat caaatagatt ctgataaagt ttatgatgac
3301 ggtgcaccgc cctgtacaat caagtgctgg tccacaagt caggtgaatg gctgttggga
3361 atccttaatg gcaattgggt ggtagttgct gttctgattg taattttgat attatcgata
3421 ctccttttta gcttttttg tcctgtcaga agtgaaaga ataaagctaa ttagtgaata
3481 tatatgtgag caagagtatg acaacattat ttcattatat gtatgttctt atatcaataa
3541 catttgtata ttcccataac cgaaatattt atactaattt ttatttttat acaagtatta
3601 actaacccat taacagctaa aaaaaacaaa tccttaacac ctatataatc ccatttgctt
3661 attacgaggc ttttgttcct gcggagcata ctacta
```

FIGURE 5A (SEQ ID NO:9)

```
   1 MVGWVCIFLV VLTTATAGLT RNLYELKIEC PHTVGLGQGY VTGSVEITPI LLTQVADLKI
  61 ESSCNFDLHV PATTTQKYNQ VDWTKKSSTT ESTNAGATTF EAKTKEINLK GTCNIPPTTF
 121 EAAYKSRKTV ICYDLACNQT HCLPTVHLIA PVQTCMSVRS CMIGLLSSRI QVIYEKTYCV
 181 TGQLIEGLCF IPTHTIALTQ PGHTYDTMTL PVTCFLVAKK LGTQLKLAVE LEKLITGVSC
 241 TENSFQGYYI CFIGKHSEPL FVPTMEDYRS AELFTRMVLN PRGEDHDPDQ NGQGLMRIAG
 301 PVTAKVPSTE TTETMQGIAF AGAPMYSSFS TLVRKADPEY VFSPGIIAES NHSVCDKKTV
 361 PLTWTGFLAV SGEIEKITGC TVFCTLAGPG ASCEAYSETG IFNISSPTCL VNKVQKFRGS
 421 EQRINFMCQR VDQDVVVYCN GQKKVILTKT LVIGQCIYTF TSLFSLIPGV AHSLAVELCV
 481 PGLHGWATTA LLITFCFGWL LIPAVTLIIL KILRLLTFSC SHYSTESKFK VILERVKVEY
 541 QKTMGSMVCD ICHHECETAK ELETHKKSCP EGQCPYCMTI TESTESALQA HFAICKLTNR
 601 FQENLKKSLK RPEVRKGCYR TLGVFRYKSR CYVGLVWGIL LTTELIIWAA SADTPLMESG
 661 WSDTAHGVGI IPMKTDLELD FALASSSSYS YRRKLVNPAN QEETLPFHFQ LDKQVVHAEI
 721 QNLGHWMDGT FNIKTAFHCY GECKKYAYPW QTAKCFFEKD YQYETSWGCN PPDCPGVGTG
 781 CTACGVYLDK LRSVGKAYKI VSLKYTRKVC IQLGTEQTCK HIDVNDCLVT PSVKVCMIGT
 841 ISKLQPGDTL LFLGPLEQGG IILKQWCTTS CVFGDPGDIM STTSGMRCPE HTGSFRKICG
 901 FATTTPTCEYQ GNTVSGFQRM MATRDSFQSF NVTEPHITSN RLEWIDPDSS IKDHINMVLN
 961 RDVSFQDLSD NPCKVDLHTQ SIDGAWGSGV GFTLVCTVGL TECANFITSI KACDSAMCYG
1021 ATVTNLLRGS NTVKVVGKGG HSGSLFKCCH DTDCTEEGLA ASPPHLDRVT GYNQIDSDKV
1081 YDDGAPPCTI KCWFTKSGEW LLGILNGNWV VVAVLIVILI LSILLFSFFC PVRSRKNKAN
```

FIGURE 5B (SEQ ID NO:10)

ANDV M SEGMENT

```
   1 tagtagtaga ctccgcaaga agaagcaaaa aattaaagaa gtgagtttaa aatggaaggg
  61 tggtatctgg ttgttcttgg agtctgctat acgctgacac tggcaatgcc caagaccatt
 121 tatgagctta aaatggaatg cccgcacact gtgggtctcg gtcaaggtta catcattggc
 181 tcaacagaac taggtttgat ctcaattgag gctgcatctg atataaagct cgagagctct
 241 tgcaattttg atcttcatac aacatctatg gcccagaaga gtttcaccca agttgaatgg
 301 agaaagaaaa gtgacacaac tgataccaca aatgctgcgt ccactacctt tgaagcacaa
 361 actaaaactg ttaaccttag agggacttgt atactggcac ctgaactcta tgatacattg
 421 aagaaagtaa aaaagacagt cctgtgctat gatctaacat gtaatcaaac acattgtcag
 481 ccaactgtct atctgattgc acctgtattg acatgcatgt caataagaag ttgtatggct
 541 agtgtgttta caagcaggat tcaggtgatt tatgaaaaga cacattgtgt aacaggtcag
 601 ctgattgagg gtcagtgttt caacccagca cacacattga cattatctca gcctgctcac
 661 acttatgata ctgtcaccct tcctatctct tgttttttca caccaaagaa gtcggagcaa
 721 ctaaaagtta taaaaacatt tgaaggaatt ctgacgaaga caggttgcac ggagaatgca
 781 ttgcagggtt attatgtgtg ttttttaggg agtcattcag aaccttttaat tgttccgagt
 841 ttggaggaca tacggtctgc tgaagttgtt agtaggatgc ttgtacaccc tagggagaa
 901 gaccatgatg ccatacagaa ttcacaaagt cacttaagaa tagtgggacc tatcacagca
 961 aaagtgccat caactagttc cacagatacc ctaaagggga cagcctttgc aggcgtccca
1021 atgtatagct ctttatctac actagtcaga aatgcagacc cagaatttgt attttctcca
1081 ggtatagtac ctgaatctaa tcacagtaca tgtgataaga agacagtacc tatcacatgg
1141 acaggctacc taccaatatc aggtgagatg gaaaaagtga ctggatgtac agttttttgt
1201 acactagcag gacctggtgc tagttgtgag gcctattctg aaaatggtat atttaacatc
1261 agttctccaa catgtcttgt aaacaaagtc caagatttc gtggatctga acagaaaata
1321 aatttatct gtcagcgggt agatcaggat gttgttgtat actgcaatgg gcaaaagaaa
1381 gtcatattaa ccaaaacttt ggttattggg cagtgtattt atacattcac aagcctattt
1441 tcattgatgc ctgatgtagc ccactcattg gctgtagaat tatgtgtccc gggattacat
1501 ggatgggcca ctgtcatgct tctatcaaca ttctgctttg ggtgggtctt gattcctgcg
1561 gtcacattaa taatattaaa gtgtctaagg gttttgacgt tttcttgttc ccattacact
1621 aatgagtcaa aatttaaatt catcctgaaa aaagttaaaa ttgaatacca aaagactatg
1681 ggatcaatgg tgtgcgatgt atgtcatcat gagtgtgaaa cagcaaaaga acttgaatca
1741 catagacaga gttgtatcaa tggacaatgt ccttattgca tgacaataac tgaagcaact
1801 gaaagtgcct tgcaagccca ttattccatt tgtaaattga caggaagatt tcaggaggca
1861 ctgaaaaagt cacttaaaaa gccagaggta aaaaaaggtt gttacagaac actcggggta
1921 tttagatata aaagtagatg ttatgtgggt ttggtatggt gctattgtt gacatgtgaa
1981 attgttattg gggccgcaag tgcagagact ccactaatgg agtcaggctg tcagatacg
2041 gctcatggtg ttggtgagat tccaatgaag acagacctcg agctggactt tcactgcct
2101 tcttcatcct cttacagtta taggagaaag ctcacaaacc cagccaataa agaagagtct
2161 attcccttcc acttccagat ggaaaaacaa gtaattcatg ctgaaatcca acccctggt
2221 cattggatgg atgcgacatt taatattaag actgcatttc attgttatgg tgcatgccag
2281 aaatactctt atccatggca gacatctaag tgcttctttg aaaaggacta ccagtatgaa
2341 acaggctggg gctgtaatcc tggtgactgc ccagggggttg ggactggatg cactgcttgt
2401 ggtgtttatc tcgataaact aaaatctgtt gggaaggcct ataagataat ttctttaaaa
2461 tataccagaa aggtttgtat tcagttagga acagaacaaa cttgcaagca tattgatgca
2521 aatgattgtt tagtgacacc atctgtgaaa gtttgcatag tgggcacagt ttcaaaactt
2581 caaccatctg atactctttt gttcttaggt ccactagaac aagggggaat cattcttaag
2641 caatggtgca caacatcatg tgcatttggg gaccctggtg atatcatgtc cactcccagt
2701 ggtatgaggt gtccagagca cactggatca tttaggaaaa tttgcggttt tgctactaca
2761 ccagtttgtg aatatcaagg aaatatcaag tctggatata aaagaatgat ggcaacaaaa
2821 gattcattcc aatcatttaa cttcacatca caacaaacaa gcttgaatgg
2881 atcgacccag atgggaatac aagagaccac gtaaaccttg tcttaaatag agatgtctca
2941 tttcaggatt taagtgataa cccctgtaaa gtagacctac acacacaagc aatagaaggg
3001 gcatgggggtt ctggtgtagg gtttacactc acatgtactg tcggattaac agagtgccca
3061 agttttatga catcaattaa ggcatgtgac ctagctatgt gttatggatc aacagtaaca
3121 aaccttgcca ggggctctaa tacagtgaaa gtagttggta aggaggcca ttcagggtcc
3181 tcatttaaat gctgtcatga tacagattgc tcctctgaag gtttacttgc atcagcccct
3241 catcttgaga gggtaacagg attcaatcaa attgattcag ataaggttta tgatgatgt
3301 gcaccacctg gcacattcaa atgctggtc actaagtcag gtgagtggct tcttgggatc
3361 ttaaacggga attggattgt tgttgtagtg cttgttgtga tactcattct ctctatcata
3421 atgttcagtg ttttgtgtcc caggagaggg cacaagaaaa ctgtctaagc gttgacctca
3481 actcctacat tagatcatat acatttatgc acttcctcat atttagctgc actaagatat
3541 taataaactc tagttattga ctttataaga ttattatgga actaacctca cttaaaaaaa
3601 acaaatactt tactcatata taactccata ttctcttacc gaggcttttg ttcctgcgga
3661 gcatactact a
```

FIGURE 6A (SEQ ID NO:11)

```
   1 MEGWYLVVLG  VCYTLTLAMP  KTIYELKMEC  PHTVGLGQGY  IIGSTELGLI  SIEAASDIKL
  61 ESSCNFDLHT  TSMAQKSFTQ  VEWRKKSDTT  DTTNAASTTF  EAQTKTVNLR  GTCILAPELY
 121 DTLKKVKKTV  LCYDLTCNQT  HCQPTVYLIA  PVLTCMSIRS  CMASVFTSRI  QVIYEKTHCV
 181 TGQLIEGQCF  NPAHTLTLSQ  PAHTYDTVTL  PISCFFTPKK  SEQLKVIKTF  EGILTKTGCT
 241 ENALQGYYVC  FLGSHSEPLI  VPSLEDIRSA  EVVSRMLVHP  RGEDHDAIQN  SQSHLRIVGP
 301 ITAKVPSTSS  TDTLKGTAFA  GVPMYSSLST  LVRNADPEFV  FSPGIVPESN  HSTCDKKTVP
 361 ITWTGYLPIS  GEMEKVTGCT  VFCTLAGPGA  SCEAYSENGI  FNISSPTCLV  NKVQRFRGSE
 421 QKINFICQRV  DQDVVVYCNG  QKKVILTKTL  VIGQCIYTFT  SLFSLMPDVA  HSLAVELCVP
 481 GLHGWATVML  LSTFCFGWVL  IPAVTLIILK  CLRVLTFSCS  HYTNESKFKF  ILEKVKIEYQ
 541 KTMGSMVCDV  CHHECETAKE  LESHRQSCIN  GQCPYCMTIT  EATESALQAH  YSICKLTGRF
 601 QEALKKSLKK  PEVKKGCYRT  LGVFRYKSRC  YVGLVWCLLL  TCEIVIWAAS  AETPLMESGW
 661 SDTAHGVGEI  PMKTDLELDF  SLPSSSSYSY  RRKLTNPANK  EESIPFHFQM  EKQVIHAEIQ
 721 PLGHWMDATF  NIKTAFHCYG  ACQKYSYPWQ  TSKCFFEKDY  QYETGWGCNP  GDCPGVGTGC
 781 TACGVYLDKL  KSVGKAYKII  SLKYTRKVCI  QLGTEQTCKH  IDANDCLVTP  SVKVCIVGTV
 841 SKLQPSDTLL  FLGPLEQGGI  ILKQWCTTSC  AFGDPGDIMS  TPSGMRCPEH  TGSFRKICGF
 901 ATTPVCEYQG  NTISGYKRMM  ATKDSFQSFN  LTEPHITTNK  LEWIDPDGNT  RDHVNLVLNR
 961 DVSFQDLSDN  PCKVDLHTQA  IEGAWGSGVG  FTLTCTVGLT  ECPSFMTSIK  ACDLAMCYGS
1021 TVTNLARGSN  TVKVVGKGGH  SGSSFKCCHD  TDCSSEGLLA  SAPHLERVTG  FNQIDSDKVY
1081 DDGAPPCTFK  CWFTKSGEWL  LGILNGNWIV  VVVLVVILIL  SIIMFSVLCP  RRGHKKTV
```

FIGURE 6B (SEQ ID NO:12)

HTNV G1

```
  1 atgagttttg gggaaaacag tgtgataggt tatgtagaat taccccccgt gccattggcc
 61 gacacagcac agatggtgcc tgagagttct tgtaacatgg ataatcacca atcgttgaat
121 acaataacaa aatatacccca agtaagttgg agaggaaagg ctgatcagtc acagtctagt
181 caaaattcat ttgagacagt gtccactgaa gttgacttga aaggaacatg tgttctaaaa
241 cactaatag
```

A (SEQ ID NO:13)

```
  1 MSFGENSVIG YVELPPVPLA DTAQMVPESS CNMDNHQSLN TITKYTQVSW RGKADQSQSS
 61 QNSFETVSTE VDLKGTCVLK H
```

B (SEQ ID NO:14)

FIGURE 7

PUUV G1

```
  1 atgagattag ggcagggtct tgttgtgggt tcagtagaat tgccatctct tccaatacag
 61 caggtcgaga cactaaagct ggagagttct tgtaattttg atctacatac cagtacagca
121 ggacaacaat cattcacaaa atggacatgg gaaattaaag gtgatcttgc agagaacaca
181 caggcatcat caacaagttt tcaaacaaaa agcagtgaag tgaatttgag aggattatgt
241 ttgatcccta cttaatag
```

A (SEQ ID NO:15)

```
  1 MRLGQGLVVG SVELPSLPIQ QVETLKLESS CNFDLHTSTA GQQSFTKWTW EIKGDLAENT
 61 QASSTSFQTK SSEVNLRGLC LIPT
```

B (SEQ ID NO:16)

FIGURE 8

SEOV G1

```
  1 atgaaatttg gggaaacaag tgtgtcaggc tacacagaac tgcccccact ctcattacag
 61 gaggcagaac agctggtgcc agagagctca tgcaacatgg acaaccacca atcactctca
121 acaataaata aattaaccaa ggtcatatgg cggaaaaagg caaatcagga atcagcaaac
181 cagaattcat ttgaacttat ggagagtgaa gtcagcttta aagggttgtg tatgttaaag
241 cattaatag
```

A (SEQ ID NO:17)

```
  1 MKFGETSVSG YTELPPLSLQ EAEQLVPESS CNMDNHQSLS TINKLTKVIW RKKANQESAN
 61 QNSFELMESE VSFKGLCMLK H
```

B (SEQ ID NO:18)

FIGURE 9

DOBV G1

```
  1 atgaactttg gggagagcag tgtaacaggt aaggtggaat taccacccct tctgctcaca
 61 gatgcagagg ccttggtccc ggagagttct tgtaacatgg acaaccatca gtctatgtca
121 attatacaaa aagtgacaaa agtgagttgg agaaaaaagg cagacaaagc ccaagctgcc
181 aaggactcat ttgagacaac atcagcgag gttaatctga agggacatg cacattgagt
241 cattaatag
```

A (SEQ ID NO:19)

```
  1 MNFGESSVTG KVELPPLLLT DAEALVPESS CNMDNHQSMS IIQKVTKVSW RKKADKAQAA
 61 KDSFETTSSE VNLKGTCTLS H
```

B (SEQ ID NO:20)

FIGURE 10

SNV G1

```
  1 atgggtttag gtcagggtta cgtgacaggt tcagtggaaa ttacacctat tctcttaacg
 61 caggtagctg atctgaagat tgagagttct tgtaatttcg atttgcatgt cccggctacc
121 actacccaaa aatacaatca ggttgactgg accaaaaaaa gttcaactac agaaagcaca
181 aatgcaggtg caactacatt tgaggctaaa acaaaagaga taaatttgaa aggcacatgt
241 aatattcctc cataatag
```

A (SEQ ID NO:21)

```
  1 MGLGQGYVTG SVEITPILLT QVADLKIESS CNFDLHVPAT TTQKYNQVDW TKKSSTTEST
 61 NAGATTFEAK TKEINLKGTC NIPP
```

B (SEQ ID NO:22)

FIGURE 11

ANDV G1

```
  1 atgggtctcg gtcaaggtta catcattggc tcaacagaac taggtttgat ctcaattgag
 61 gctgcatctg atataaagct cgagagctct tgcaattttg atcttcatac aacatctatg
121 gcccagaaga gtttcaccca agttgaatgg agaaagaaaa gtgacacaac tgataccaca
181 aatgctgcgt ccactacctt tgaagcacaa actaaaactg ttaaccttag agggacttgt
241 atactggcac cttaatag
```

A (SEQ ID NO:23)

```
  1 MGLGQGYIIG STELGLISIE AASDIKLESS CNFDLHTTSM AQKSFTQVEW RKKSDTTDTT
 61 NAASTTFEAQ TKTVNLRGTC ILAP
```

B (SEQ ID NO:24)

FIGURE 12

HTNV N

```
   1 atggcaacta tggaggaatt acagagggaa atcaatgccc atgagggtca attagtgata
  61 gccaggcaga aggtgaggga tgcagaaaaa cagtatgaaa aggatccaga tgagttgaac
 121 aagagaacat taactgaccg agagggcgtt gcagtatcta tccaggcaaa aattgatgag
 181 ttaaaaaggc aactggcaga taggattgca actgggaaaa accttgggaa ggaacaagat
 241 ccaacagggg tggagcctgg agaccatctg aaagagaggt caatgctcag ttatggtaat
 301 gtgctggatt taaaccattt ggatattgat gaacctacag gacagacagc agactggctg
 361 agcatcatcg tctatcttac atcctttgtc gtcccgatac ttctgaaagc tctgtatatg
 421 ttgacaacaa gggggaggca aactaccaag gataataaag ggacccggat tcgatttaag
 481 gatgatagct cgttcgagga tgttaacggt atccggaaac caaaacatct ttacgtgtcc
 541 ttgccaaatg cacagtcaag catgaaggca gaagagatta cacctggtag atatagaaca
 601 gcagtctgtg ggctctaccc tgcacagatt aaggcacggc agatgatcag tccagttatg
 661 agtgtaattg gttttctagc attagcaaag gactggagtg atcgtatcga acaatggtta
 721 attgaacctt gcaagcttct tccagataca gcagcagtta gcctccttgg tggtcctgca
 781 acaaacaggg actacttacg gcagcggcaa gtggcattag caatatgga gacaaaggag
 841 tcaaaggcta tacgccagca tgcagaagca gctggctgta gcatgattga agatattgag
 901 tcaccatcat caatatgggt ttttgctgga gcaccagacc gttgtccacc aacatgtttg
 961 tttatagcag gtattgctga gcttggggca ttttttttcca tcctgcagga catgcgaaat
1021 acaatcatgg catctaagac agttggaaca tctgaggaga agctacggaa gaaatcatca
1081 ttttatcagt cctacctcag aaggacacaa tcaatgggga tacaactagg ccagagaatt
1141 attgtgctct tcatggttgc ctggggaaag gaggctgtgg acaacttcca cttagggat
1201 gatatggatc ctgagctaag gacactggca cagagcttga ttgatgtcaa agtgaaggaa
1261 atctccaacc aagagccttt gaaactctaa tag
```

A (SEQ ID NO:25)

```
  1 MATMEELQRE INAHEGQLVI ARQKVRDAEK QYEKDPDELN KRTLTDREGV AVSIQAKIDE
 61 LKRQLADRIA TGKNLGKEQD PTGVEPGDHL KERSMLSYGN VLDLNHLDID EPTGQTADWL
121 SIIVYLTSFV VPILLKALYM LTTRGRQTTK DNKGTRIRFK DDSSFEDVNG IRKPKHLYVS
181 LPNAQSSMKA EEITPGRYRT AVCGLYPAQI KARQMISPVM SVIGFLALAK DWSDRIEQWL
241 IEPCKLLPDT AAVSLLGGPA TNRDYLRQRQ VALGNMETKE SKAIRQHAEA AGCSMIEDIE
301 SPSSIWVFAG APDRCPPTCL FIAGIAELGA FFSILQDMRN TIMASKTVGT SEEKLRKKSS
361 FYQSYLRRTQ SMGIQLGQRI IVLFMVAWGK EAVDNFHLGD DMDPELRTLA QSLIDVKVKE
421 ISNQEPLKL
```

B (SEQ ID NO:26)

FIGURE 13

PUUV N

```
   1 atgagtgact tgacagacat ccaagaggag ataacccgcc atgagcaaca acttgttgtt
  61 gccagacaaa aactcaagga tgcagagaga gcagtggaag tgtacccgga tgacgttaac
 121 aagaacacat tacaagcaag acaacaaaca gtgtcagcac tggaggataa actcgcagac
 181 tacaagagaa gaatggcaga tgctgtgtcc cggaagaaaa tggatactaa acctactgac
 241 ccgactggga ttgaacctga tgatcatctc aaggagagat caagccttag atatggaaat
 301 gtccttgatg tgaatgctat tgacattgaa gaaccaagtg gccagacagc agattggtat
 361 actatcggag tctatgtaat agggttcaca attcctatca ttttgaaggc tctatatatg
 421 ttgtcaacac gtggaagaca gactgtaaag gaaaacaaag gaacacggat caggttcaag
 481 gatgacacat catttgagga tatcaatggc atcaggagac caaaacacct atatgtatcc
 541 atgcctactg cccagtccac catgaaagct gaagaactta cacctggacg gttccgtaca
 601 atagtatgtg gcttattccc tacacagata caagttcgta acatcatgag tccagtaatg
 661 ggagtgattg gttttctttt cttcgttaaa gactggccag aaaaaattag ggagtttatg
 721 gagaaagaat gcccctttcat aaagccagaa gttaaacctg ggacaccagc acaggaggta
 781 gaattttga aaagaaatag agtttatttc atgacccgcc aggatgttct tgacaaaaat
 841 catgtggctg acatcgataa gttgattgac tatgctgccg ctggtgaccc tacatcgcct
 901 gatgacatcg aatctcctaa tgcaccatgg gtatttgctt gtgcaccaga tcggtgcccc
 961 ccaacatgta tttatgttgc tgggatggct gaattaggtg cattctttc catcttacag
1021 gatatgagga acaccataat ggcatctaaa actgtgggca cagcagaaga gaaactgaaa
1081 aagaagtcct ccttctatca atcatatttg cgccgaacac aatcaatggg gattcaactt
1141 gatcagagga taatcctact gtacatgttg gaatggggaa aagaaatggt ggatcatttc
1201 catcttggtg atggcatgga tcctgagcta aggggccttg ctcagtcact catagaccag
1261 aaggtaaaag agatatcaaa ccaagaaccc ttaaagatat gatag
```

A (SEQ ID NO:27)

```
  1 MSDLTDIQEE ITRHEQQLVV ARQKLKDAER AVEVYPDDVN KNTLQARQQT VSALEDKLAD
 61 YKRRMADAVS RKKMDTKPTD PTGIEPDDHL KERSSLRYGN VLDVNAIDIE EPSGQTADWY
121 TIGVYVIGFT IPIILKALYM LSTRGRQTVK ENKGTRIRFK DDTSFEDING IRRPKHLYVS
181 MPTAQSTMKA EELTPGRFRT IVCGLFPTQI QVRNIMSPVM GVIGFSFFVK DWPEKIREFM
241 EKECPFIKPE VKPGTPAQEV EFLKRNRVYF MTRQDVLDKN HVADIDKLID YAAAGDPTSP
301 DDIESPNAPW VFACAPDRCP PTCIYVAGMA ELGAFFSILQ DMRNTIMASK TVGTAEEKLK
361 KKSSFYQSYL RRTQSMGIQL DQRIILLYML EWGKEMVDHF HLGDGMDPEL RGLAQSLIDQ
421 KVKEISNQEP LKI
```

B (SEQ ID NO:28)

FIGURE 14

SEOV N

```
   1 atggcaacta tggaggaaat ccagagagaa atcagtgctc acgaggggca gcttgtgata
  61 gcacgccaga aggtcaagga tgcagaaaag cagtatgaga aggatcctga tgacttaaac
 121 aagagggcac tgcatgatcg ggagagtgtc gcagcttcaa tacaatcaaa aattgatgaa
 181 ctgaagcgcc aacttgccga caggattgca gcagggaaga acatcgggca agaccgggat
 241 cctacagggg tagagccggg tgatcatctc aaggaaagat cagcactaag ctacgggaat
 301 acactggacc tgaatagtct tgacattgat gaacctacag gacaaacagc tgattggctg
 361 actataattg tctatctaac atcattcgtg gtcccgatca tcttgaaggc actgtacatg
 421 ttaacaacaa gaggtaggca gacttcaaag gacaacaagg ggatgaggat cagattcaag
 481 gatgacagct catatgagga tgtcaatggg atcagaaagc ctaaacatct gtatgtgtca
 541 atgccaaacg cccaatccag tatgaaggct gaagagataa caccaggaag attccgcact
 601 gcagtatgtg ggctatatcc tgcacagata aaggcaagga atatggtaag ccctgtcatg
 661 agtgtagttg ggtttttggc actagcaaaa gactggacat ctagaattga gaatggcttg
 721 ggcgcaccct gcaagttcat ggcagagtct cctattgctg ggagtttatc tgggaatcct
 781 gtgaatcgtg actatatcag acaaagacaa ggtgcacttg cagggatgga gccaaaggaa
 841 tttcaagccc tcaggcaaca ttcaaaggat gctggatgta cactagttga acatattgag
 901 tcaccatcgt caatatgggt gtttgctggg gcccctgata ggtgtccacc aacatgcttg
 961 tttgttggag ggatggctga gttaggtgcc ttctttttcta tacttcagga tatgaggaac
1021 acaatcatgg cttcaaaaac tgtgggcaca gctgatgaaa agcttcgaaa gaaatcatca
1081 ttctatcaat catacctcag acgcacacaa tcaatgggaa tacaactgga ccagaggata
1141 attgttatgt ttatggttgc ctggggaaag gaggcagtgg acaacttcca tctcggtgat
1201 gacatggatc cagagcttcg tagcctggct cagatcttga ttgaccagaa agtgaaggaa
1261 atctcgaacc aggagcctat gaaattataa tag
```

A (SEQ ID NO:29)

```
   1 MATMEEIQRE ISAHEGQLVI ARQKVKDAEK QYEKDPDDLN KRALHDRESV AASIQSKIDE
  61 LKRQLADRIA AGKNIGQDRD PTGVEPGDHL KERSALSYGN TLDLNSLDID EPTGQTADWL
 121 TIIVYLTSFV VPIILKALYM LTTRGRQTSK DNKGMRIRFK DDSSYEDVNG IRKPKHLYVS
 181 MPNAQSSMKA EEITPGRFRT AVCGLYPAQI KARNMVSPVM SVVGFLALAK DWTSRIEEWL
 241 GAPCKFMAES PIAGSLSGNP VNRDYIRQRQ GALAGMEPKE FQALRQHSKD AGCTLVEHIE
 301 SPSSIWVFAG APDRCPPTCL FVGGMAELGA FFSILQDMRN TIMASKTVGT ADEKLRKKSS
 361 FYQSYLRRTQ SMGIQLDQRI IVMFVAWGK EAVDNFHLGD DMDPELRSLA QILIDQKVKE
 421 ISNQEPMKL
```

B (SEQ ID NO:30)

FIGURE 15

DOBV N

```
   1 atggcaacat tagaggaact ccaaaaggaa atcaacaacc atgaaggtca attggtgata
  61 gccaggcaga aggtgaagga tgcagaaaag cagtatgaaa aggaccctga cgacctgaat
 121 aaaagggcat tgagtgatcg ggaaagcatt gcacaatcaa ttcagggaaa aatcgatgaa
 181 ttaaggagac agctggctga tcgtgtggca gcagggaaaa acatcggcaa agaaagggac
 241 ccaactgggc tagaccctgg agatcacctc aaagagaagt caatgctcag ttatggaaat
 301 gtcattgacc tcaaccatct tgacattgat gaacctacag ggcaaactgc agactggcta
 361 agcattgtga tctacctgac atcattgtg gtcccaatac tgttgaaggc tctttacatg
 421 cttaccacca gagggagaca aactactaaa gacaataagg gaatgaggat tcgatttaag
 481 gatgacagct cttttgaaga tgtgaatggg attcgaaagc caaagcacct gttcttgtca
 541 atgcccaatg cacaatctag tatgaaggca gatgagatta caccaggtcg gttcaggact
 601 gcaatctgtg gactataccc agcccaggtt aaggcaagga atttaatcag tcctgtgatg
 661 agtgtgattg ggtttgtagc ccttgcaaaa aactggacag aacgggttga agaatggctt
 721 gacctcccgt gcaagctact atctgagcca tctccaacgt ctttgaccaa aggcccatcc
 781 accaatcgtg actacttgaa tcaaagacaa ggagcgcttg caaaaatgga aacgaaggaa
 841 gctcaggctg tgaggaaaca tgccatagat gctggttgca acctcattga ccatatagac
 901 tcaccatcat caatctgggt ctttgcagga gcacctgata gatgccctcc tacctgcctg
 961 tttattgcag gcatggcaga gctaggtgca ttctttgctt gcctccagga catgaggaac
1021 accatcatgg catcaaaaac catcggaaca tctgaggaaa agctaaagaa aaagtcatct
1081 ttttaccaat cttacctacg gaggacacaa tctatgggga tacaactgga ccagcgcatc
1141 attgtgcttt ttatggttga ctggggaaaa gaggcagttg atagttttca tctcggtgac
1201 gatatggatc ctgagctccg gcgcctggca caggcattga ttgaccaaaa agtgaaggaa
1261 atatctaatc aggagccgct taagctttaa tag
```

A (SEQ ID NO:31)

```
  1 MATLEELQKE INNHEGQLVI ARQKVKDAEK QYEKDPDDLN KRALSDRESI AQSIQGKIDE
 61 LRRQLADRVA AGKNIGKERD PTGLDPGDHL KEKSMLSYGN VIDLNHLDID EPTGQTADWL
121 SIVIYLTSFV VPILLKALYM LTTRGRQTTK DNKGMRIRFK DDSSFEDVNG IRKPKHLFLS
181 MPNAQSSMKA DEITPGRFRT AICGLYPAQV KARNLISPVM SVIGFVALAK NWTERVEEWL
241 DLPCKLLSEP SPTSLTKGPS TNRDYLNQRQ GALAKMETKE AQAVRKHAID AGCNLIDHID
301 SPSSIWVFAG APDRCPPTCL FIAGMAELGA FFACLQDMRN TIMASKTIGT SEEKLKKKSS
361 FYQSYLRRTQ SMGIQLDQRI IVLFMVDWGK EAVDSFHLGD DMDPELRRLA QALIDQKVKE
421 ISNQEPLKL
```

B (SEQ ID NO:32)

FIGURE 16

SNV N

```
   1 atgagcaccc tcaaagaagt gcaagacaac attactctcc acgaacaaca actcgtgact
  61 gccaggcaga agctcaaaga tgcagagaga gcggtggaat tggaccccga tgatgttaac
 121 aaaagcacat tacagagcag acgggcagct gtgtctgcat tggagaccaa actcggagaa
 181 ctcaagcggg aactggctga tcttattgca gctcagaaat tggcttcaaa acctgttgat
 241 ccaacaggga ttgaacctga tgaccattta aaggaaaaat catcactgag atatggaaat
 301 gtccttgatg taaattccat tgacctagaa gaaccaagtg ggcaaacagc tgattggaaa
 361 tccatcggac tctacattct aagttttgca ttaccgatta tccttaaagc cttgtacatg
 421 ttatctacta gaggccgtca aacaatcaaa gaaaacaagg gaacaagaat tcgatttaag
 481 gatgattcat cttatgaaga agtcaatgga atacgtaaac caagacatct atatgtttct
 541 atgccaactg ctcagtctac aatgaaagca gatgagatta ctcctgggag gttccgtaca
 601 attgcttgtg ggttattccc ggcccaagtc aaagcaagga atattatcag tcctgttgtg
 661 ggtgtgattg ctttagtttt ctttgtgaaa gattggatgg aaagaattga tgactttctg
 721 gctgcacgtt gtccatttct acccgaacag aaagacccta gggatgctgc attggcaact
 781 aacagagcct attttataac acgtcaatta caggttgatg agtcaaaggt tagtgatatt
 841 gaggatctaa ttgctgatgc aagggctgag tctgccacta tattcgcaga tatcgccact
 901 cctcattcag tttgggtctt cgcatgtgct ccagatcgtt gtccacctac agcattatat
 961 gtggccggga tgccggagtt gggtgcattt tttgctattc ttcaggatat gaggaacacc
1021 ataatggcat caaatctgt ggggacatct gaagagaaat gaagaaaaa atcagcattc
1081 taccagtcat acttgagacg tactcagtca atggggattc aactggacca gaagataatc
1141 atcttataca tgagccattg gggaagagag gccgtgaatc acttccatct tggagatgat
1201 atggatcttg aacttaggga acttgcccag accctcgtag acatcaaggt cagggagatc
1261 tctaaccaag aaccacttaa actttaatag
```

A (SEQ ID NO:33)

```
  1 MSTLKEVQDN ITLHEQQLVT ARQKLKDAER AVELDPDDVN KSTLQSRRAA VSALETKLGE
 61 LKRELADLIA AQKLASKPVD PTGIEPDDHL KEKSSLRYGN VLDVNSIDLE EPSGQTADWK
121 SIGLYILSFA LPIILKALYM LSTRGRQTIK ENKGTRIRFK DDSSYEEVNG IRKPRHLYVS
181 MPTAQSTMKA DEITPGRFRT IACGLFPAQV KARNIISPVV GVIGFSFVK DWMERIDDFL
241 AARCPFLPEQ KDPRDAALAT NRAYFITRQL QVDESKVSDI EDLIADARAE SATIFADIAT
301 PHSVWVFACA PDRCPPTALY VAGMPELGAF FAILQDMRNT IMASKSVGTS EEKLKKKSAF
361 YQSYLRRTQS MGIQLDQKII ILYMSHWGRE AVNHFHLGDD MDLELRELAQ TLVDIKVREI
421 SNQEPLKL
```

B (SEQ ID NO:34)

FIGURE 17

ANDV N

```
   1 atgagcaccc tccaagaatt gcaggaaaac atcacagcac acgaacaaca gctcgtgact
  61 gctcggcaaa agcttaaaga tgccgagaag gcggtggagg tggacccgga tgacgttaac
 121 aagagcacac tacaaaatag acgggcagct gtgtctacat tggagaccaa actcggggaa
 181 ctcaagagac aacttgcaga tctggtggca gctcaaaaat tggctacaaa accagttgat
 241 ccaacagggc ttgagcctga tgaccatctg aaagagaaat catctttgag atatgggaat
 301 gtcctggatg ttaactcaat cgatttggaa gaaccgagtg gacagactgc tgattggaag
 361 gctataggag catatatctt agggtttgca attccgatca tactaaaagc cctatatatg
 421 ctgtcaaccc gtggaagaca gactgtgaaa gacaacaaag gaaccaggat aaggtttaag
 481 gatgattctt cctttgaaga ggtcaatggg atacgtaaac gaaacaccct ttatgtctca
 541 atgccaactg cacaatctac tatgaaggct gaggaaatta cgccaggacg tttaggaca
 601 attgcttgtg gcctctttcc agcacaggtc aaagctcgaa atataataag tcctgtgatg
 661 ggagtaatcg gatttggctt ctttgtgaag gactggatgg atcggataga ggaattcctg
 721 gctgcagagt gtccattcct gcctaagcca aaggttgcct cagaagcctt catgtctacc
 781 aacaagatgt attttctgaa tagacaaaga caagtcaatg aatctaaggt tcaagacatc
 841 attgatttaa tagatcatgc tgaaactgaa tctgctacct tgtttacaga aattgcaaca
 901 ccccattcag tctgggtgtt tgcatgtgcg cctgaccggt gcctccgac tgcattgtat
 961 gttgcagggg taccagaact tggtgcattc ttttccattc ttcaggacat gcgcaatacc
1021 atcatggcat ccaaatctgt ggggactgca gaagagaagc tgaagaagaa atctgccttt
1081 tatcaatctt acctaagaag gacacaatct atggggattc aactggacca gaaaatcata
1141 attctctaca tgctttcatg gggtaaagaa gctgtgaatc atttccatct tggtgatgat
1201 atggaccctg aactaaggca gctagctcaa tccctgattg acaccaaggt gaaggagatc
1261 tccaaccaag agccacttaa gttgtagtag
```

A (SEQ ID NO:35)

```
   1 MSTLQELQEN ITAHEQQLVT ARQKLKDAEK AVEVDPDDVN KSTLQNRRAA VSTLETKLGE
  61 LKRQLADLVA AQKLATKPVD PTGLEPDDHL KEKSSLRYGN VLDVNSIDLE EPSGQTADWK
 121 AIGAYILGFA IPIILKALYM LSTRGRQTVK DNKGTRIRFK DDSSFEEVNG IRKPKHLYVS
 181 MPTAQSTMKA EEITPGRFRT IACGLFPAQV KARNIISPVM GVIGFGFFVK DWMDRIEEFL
 241 AAECPFLPKP KVASEAFMST NKMYFLNRQR QVNESKVQDI IDLIDHAETE SATLFTEIAT
 301 PHSVWVFACA PDRCPPTALY VAGVPELGAF FSILQDMRNT IMASKSVGTA EEKLKKKSAF
 361 YQSYLRRTQS MGIQLDQKII ILYMLSWGKE AVNHFHLGDD MDPELRQLAQ SLIDTKVKEI
 421 SNQEPLKL
```

B (SEQ ID NO:36)

FIGURE 18

SOD

```
  1 atggctacaa aggctgtttg tgttttgaag ggtgacggcc cagttcaagg tattattaac
 61 ttcgagcaga aggaaagtaa tggaccagtg aaggtgtggg gaagcattaa aggactgact
121 gaaggcctgc atggattcca tgttcatgag tttggagata atacagcagg ctgtaccagt
181 gcaggtcctc actttaatcc tctatccgcg ctagccggtg ggccaaagga tgaagagagg
241 catgttggag acttgggcaa tgtgactgct gacaaagatg gtgtggccga tgtgtctatt
301 gaagattctg tgatctcact ctcaggagac cattgcatca ttggccgcac actggtggtc
361 catgaaaaag cagatgactt gggcaaaggt ggaaatgaag aaagtacaaa gacaggaaac
421 gctggaagtc gtttggcttg tggtgtaatt gggatcgccc agaatttgga attcacgcgt
481 caaaacaaa
```

A (SEQ ID NO:37)

```
  1 MATKAVCVLK GDGPVQGIIN FEQKESNGPV KVWGSIKGLT EGLHGFHVHE FGDNTAGCTS
 61 AGPHFNPLSA LAGGPKDEER HVGDLGNVTA DKDGVADVSI EDSVISLSGD HCIIGRTLVV
121 HEKADDLGKG GNEESTKTGN AGSRLACGVI GIAQNLEFTR QNK
```

B (SEQ ID NO:38)

FIGURE 19

SOD/HTNV G1

MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMSFGENSV
IGYVELPPVPLADTAQMVPESSCNMDNHQSLNTITKYTQVSWRGKADQSQSSQNSFE
TVSTEVDLKGTCVLKH

FIGURE 20 (SEQ ID NO:42)

SOD/PUUV G1

MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMRLGQGLV
VGSVELPSLPIQQVETLKLESSCNFDLHTSTAGQQSFTKWTWEIKGDLAENTQASST
SFQTKSSEVNLRGLCLIPT

FIGURE 21 (SEQ ID NO:43)

SOD/SEOV G1

MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMKFGETSV
SGYTELPPLSLQEAEQLVPESSCNMDNHQSLSTINKLTKVIWRKKANQESANQNSFE
LMESEVSFKGLCMLKH

FIGURE 22 (SEQ ID NO:44)

SOD/DOBV G1
MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMNFGESSV
TGKVELPPLLLTDAEALVPESSCNMDNHQSMSIIQKVTKVSWRKKADKAQAAKDSFE
TTSSEVNLKGTCTLSH

FIGURE 23 (SEQ ID NO:45)

SOD/SNV G1
MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMGLGQGYV
TGSVEITPILLTQVADLKIESSCNFDLHVPATTTQKYNQVDWTKKSSTTESTNAGAT
TFEAKTKEINLKGTCNIPP

FIGURE 24 (SEQ ID NO:46)

SOD/ANDV G1
MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMGLGQGYI
IGSTELGLISIEAASDIKLESSCNFDLHTTSMAQKSFTQVEWRKKSDTTDTTNAAST
TFEAQTKTVNLRGTCILAP

FIGURE 25 (SEQ ID NO:47)

SOD/HTNV N

MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMATMEELQ
REINAHEGQLVIARQKVRDAEKQYEKDPDELNKRTLTDREGVAVSIQAKIDELKRQL
ADRIATGKNLGKEQDPTGVEPGDHLKERSMLSYGNVLDLNHLDIDEPTGQTADWLSI
IVYLTSFVVPILLKALYMLTTRGRQTTKDNKGTRIRFKDDSSFEDVNGIRKPKHLYV
SLPNAQSSMKAEEITPGRYRTAVCGLYPAQIKARQMISPVMSVIGFLALAKDWSDRI
EQWLIEPCKLLPDTAAVSLLGGPATNRDYLRQRQVALGNMETKESKAIRQHAEAAGC
SMIEDIESPSSIWVFAGAPDRCPPTCLFIAGIAELGAFFSILQDMRNTIMASKTVGT
SEEKLRKKSSFYQSYLRRTQSMGIQLGQRIIVLFMVAWGKEAVDNFHLGDDMDPELR
TLAQSLIDVKVKEISNQEPLKL

FIGURE 26 (SEQ ID NO:48)

SOD/PUUV N

MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMSDLTDIQ
EEITRHEQQLVVARQKLKDAERAVEVYPDDVNKNTLQARQQTVSALEDKLADYKRRM
ADAVSRKKMDTKPTDPTGIEPDDHLKERSSLRYGNVLDVNAIDIEEPSGQTADWYTI
GVYVIGFTIPIILKALYMLSTRGRQTVKENKGTRIRFKDDTSFEDINGIRRPKHLYV
SMPTAQSTMKAEELTPGRFRTIVCGLPTQIQVRNIMSPVMGVIGFSFFVKDWPEKI
REFMEKECPFIKPEVKPGTPAQEVEFLKRNRVYFMTRQDVLDKNHVADIDKLIDYAA
AGDPTSPDDIESPNAPWVFACAPDRCPPTCIYVAGMAELGAFFSILQDMRNTIMASK
TVGTAEEKLKKKSSFYQSYLRRTQSMGIQLDQRIILLYMLEWGKEMVDHFHLGDGMD
PELRGLAQSLIDQKVKEISNQEPLKI

FIGURE 27 (SEQ ID NO:49)

SOD/SEOV N
MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMATMEEIQ
REISAHEGQLVIARQKVKDAEKQYEKDPDDLNKRALHDRESVAASIQSKIDELKRQL
ADRIAAGKNIGQDRDPTGVEPGDHLKERSALSYGNTLDLNSLDIDEPTGQTADWLTI
IVYLTSFVVPIILKALYMLTTRGRQTSKDNKGMRIRFKDDSSYEDVNGIRKPKHLYV
SMPNAQSSMKAEEITPGRFRTAVCGLYPAQIKARNMVSPVMSVVGFLALAKDWTSRI
EEWLGAPCKFMAESPIAGSLSGNPVNRDYIRQRQGALAGMEPKEFQALRQHSKDAGC
TLVEHIESPSSIWVFAGAPDRCPPTCLFVGGMAELGAFFSILQDMRNTIMASKTVGT
ADEKLRKKSSFYQSYLRRTQSMGIQLDQRIIVMFMVAWGKEAVDNFHLGDDMDPELR
SLAQILIDQKVKEISNQEPMKL

FIGURE 28 (SEQ ID NO:50)

SOD/DOBV N
MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMATLEELQ
KEINNHEGQLVIARQKVKDAEKQYEKDPDDLNKRALSDRESIAQSIQGKIDELRRQL
ADRVAAGKNIGKERDPTGLDPGDHLKEKSMLSYGNVIDLNHLDIDEPTGQTADWLSI
VIYLTSFVVPILLKALYMLTTRGRQTTKDNKGMRIRFKDDSSFEDVNGIRKPKHLFL
SMPNAQSSMKADEITPGRFRTAICGLYPAQVKARNLISPVMSVIGFVALAKNWTERV
EEWLDLPCKLLSEPSPTSLTKGPSTNRDYLNQRQGALAKMETKEAQAVRKHAIDAGC
NLIDHIDSPSSIWVFAGAPDRCPPTCLFIAGMAELGAFFACLQDMRNTIMASKTIGT
SEEKLKKKSSFYQSYLRRTQSMGIQLDQRIIVLFMVDWGKEAVDSFHLGDDMDPELR
RLAQALIDQKVKEISNQEPLKL

FIGURE 29 (SEQ ID NO:51)

SOD/SNV N
MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMSTLKEVQ
DNITLHEQQLVTARQKLKDAERAVELDPDDVNKSTLQSRRAAVSALETKLGELKREL
ADLIAAQKLASKPVDPTGIEPDDHLKEKSSLRYGNVLDVNSIDLEEPSGQTADWKSI
GLYILSFALPIILKALYMLSTRGRQTIKENKGTRIRFKDDSSYEEVNGIRKPRHLYV
SMPTAQSTMKADEITPGRFRTIACGLFPAQVKARNIISPVVGVIGFSFFVKDWMERI
DDFLAARCPFLPEQKDPRDAALATNRAYFITRQLQVDESKVSDIEDLIADARAESAT
IFADIATPHSVWVFACAPDRCPPTALYVAGMPELGAFFAILQDMRNTIMASKSVGTS
EEKLKKKSAFYQSYLRRTQSMGIQLDQKIIILYMSHWGREAVNHFHLGDDMDLELRE
LAQTLVDIKVREISNQEPLKL

FIGURE 30 (SEQ ID NO:52)

SOD/ANDV N
MATKAVCVLKGDGPVQGIINFEQKESNGPVKVWGSIKGLTEGLHGFHVHEFGDNTAG
CTSAGPHFNPLSALAGGPKDEERHVGDLGNVTADKDGVADVSIEDSVISLSGDHCII
GRTLVVHEKADDLGKGGNEESTKTGNAGSRLACGVIGIAQNLEFTRQNKMSTLQELQ
ENITAHEQQLVTARQKLKDAEKAVEVDPDDVNKSTLQNRRAAVSTLETKLGELKRQL
ADLVAAQKLATKPVDPTGLEPDDHLKEKSSLRYGNVLDVNSIDLEEPSGQTADWKAI
GAYILGFAIPIILKALYMLSTRGRQTVKDNKGTRIRFKDDSSFEEVNGIRKPKHLYV
SMPTAQSTMKAEEITPGRFRTIACGLFPAQVKARNIISPVMGVIGFGFFVKDWMDRI
EEFLAAECPFLPKPKVASEAFMSTNKMYFLNRQRQVNESKVQDIIDLIDHAETESAT
LFTEIATPHSVWVFACAPDRCPPTALYVAGVPELGAFFSILQDMRNTIMASKSVGTA
EEKLKKKSAFYQSYLRRTQSMGIQLDQKIIILYMLSWGKEAVNHFHLGDDMDPELRQ
LAQSLIDTKVKEISNQEPLKL

FIGURE 31 (SEQ ID NO:53)

METHODS AND REAGENTS FOR DIAGNOSING HANTAVIRUS INFECTION

CROSS-REFERENCE TO RELATED APPLICATION

This application is a 371 of PCT/US05/18066, filed on May 24, 2005 and claims benefit under 35 U.S.C. 119(e) of provisional application 60/581,027 filed on Jun. 18, 2004, which application is incorporated herein by reference in its entirety.

STATEMENT REGARDING FEDERALLY SPONSORED RESEARCH OR DEVELOPMENT

This invention was made with support under NIH Grant U01 AIO54779, from the National Institute of Allergy and Infectious Diseases. Accordingly, the United States Government may have certain rights in this invention

INCORPORATION BY REFERENCE OF MATERIAL ON COMPACT DISC

This application incorporates by reference the Sequence Listing contained on the compact disc (CRF Copy), filed concurrently herewith, containing the following file:

File name: 22009.0004seqlist.txt; File size: 172 KB.

TECHNICAL FIELD

The present invention pertains generally to hantaviruses. In particular, the invention relates to immunogenic reagents derived from multiple hantavirus serotypes, including immunogenic nucleocapsid and glycoprotein polypeptides, for use in compositions for diagnosis of hantavirus infection.

BACKGROUND

Hantaviruses (Bunyaviridae: Hantavirus) are lipid-enveloped, minus-sense RNA viruses. The RNA of the viral genome is tripartite, consisting of three fragments generally designated as S, M and L for small, medium and large genome fragments, respectively. The M segment encodes a precursor protein that is processed to form the two envelope glycoproteins, termed G1 and G2. The S segment encodes a nucleocapsid protein, termed N which forms the filamentous helical nucleocapsid of the virus and elicits the humoral response. The L segment of the genome encodes an RNA-dependent RNA polymerase (RDRP). Over 20 distinct hantaviruses are found in association with specific rodent or insectivore hosts worldwide. Their modes of transmission to humans, natural reservoirs, and the clinical features of human infection have been reviewed (see, e.g., Mertz et al., *Adv. Internal Med.* (1997) 42:369-421).

Hantavirus pulmonary syndrome (HPS), also known as hantavirus cardiopulmonary syndrome (HCPS) is an acute febrile illness with up to a 50% mortality rate. Patients present with nonspecific symptoms and progress rapidly to fulminant pulmonary edema and cardiovascular collapse. The predominant agent of HPS in North America is Sin Nombre virus (SNV; also known as Four Corners virus and Muerto Canyon virus). (Song et al., *Lancet* (1994) 344:1637; Khan et al., *J. Med. Virol* (1995) 46:281-286; Kahn et al., *Am. J. Med.* (1996) 100:46-48; Morzunov et al., *J. Virol* (1995) 69:1980-1983; Rollin et al., *J. Med. Virol* (1995) 46:35-39; Centers for Disease Control and Prevention, *Morbid. Mortal. Weekly Rep.* (1993) 43:45-48). At least three other hantaviruses have been associated with HPS in North America, including New York virus (NYV), Black Creek Canal virus (BCCV) and Bayou virus (BAYV).

Worldwide, a larger toll of illness is caused by the Eurasian hantaviruses that cause hemorrhagic fever with renal syndrome (HFRS). HFRS-associated viruses include Hantaan (HTNV), Puumala (PUUV), Seoul (SEOV), and Dobrava-Belgrade (DOBV) viruses (Lee et al., *J. Infect. Dis.* (1978) 137:298-308; Lee, et al., *J. Infect. Dis.* (1982) 146:638-644; Lee et al., *J. Infect. Dis.* (1982) 146:645-651; Brummer-Korvenkontio et al., *J. Infect. Dis.* (1980) 141:131-134). Clinical manifestations of HFRS are generally most severe for HTNV and DOBV infections, whereas PUUV infection is associated with a milder form of HFRS, nephropathia epidemica (NE), occurring in Scandinavia, Finland, Western Russia and Central Europe. Mortality rates of up to 20% have been reported from the most severe forms of HFRS.

Among the HFRS-associated hantaviruses, HTNV, SEOV and DOBV are antigenically similar. The HPS-associated viruses are also closely related to one another, and cross-react with PUUV. Antigenic cross-reactivity is most pronounced among the viral N proteins. In recombinant antigen diagnostic assays, the viral N antigen is dominant over the viral glycoproteins. Antibodies to the N antigen arise early in the course of infection and are universally detectable in convalescence. All persons with acute SNV infection have detectable antibodies against the SNV N antigen of the IgM class by the onset of clinical symptoms, and almost all have IgG antibodies directed against the N and G1 antigens (Bharadwaj et al., *J. Infect. Dis.* (2000) 182:43-48). SNV G1 antibodies are not reactive with the G1 antigens of other hantaviruses (Jenison et al., *J. Virol.* (1994) 68:3000-3006; Hjelle et al., *J. Gen. Virol.* (1994) 75:2881-2888).

Hantaviruses are transmitted to humans via inhalation of virus-contaminated aerosols of rodent saliva, urine and feces. A worker can contract hantavirus infection merely by entering into a room with infected rodents, which strongly supports the prevailing view that hantaviruses are transmitted through the air. This observation is also supported by a recent epidemiologic investigation showing that indoor exposures are extremely common. Person-to-person transmission has been demonstrated for the Andes virus (ANDV) in Argentina and is likely to be responsible for two family clusters in Chile. The virus may also be transmitted after rodent bites and possibly through ingestion of contaminated food or water.

All species of hantavirus appear to be primarily associated with a specific rodent host. There are three broad groups of hantaviruses and they are associated with the rodent subfamilies of Murinae, Arvicolinae and Sigmondontinae. The phylogenetic relations among rodents in these various subfamilies parallel, for the most part, the phylogenetic and antigenic relations of viruses associated with each particular reservoir. Each of these groups of hantaviruses contains one or more species or types that are known human pathogens. Information concerning the various hantaviruses is presented in Table 1.

TABLE 1

Hantavirus Identity

| Subfamily | Virus | Associated Disease | Animal Host | Location |
|---|---|---|---|---|
| Murinae | Hantaan | HFRS | *Apodemus agrarius* | Asia, Far East Russia |
| | Dobrava | HFRS | *A. flavicollis* *A. agrarius* | Balkans Europe |
| | Seoul | HFRS | *Rattus norvegicus* *R. rattus* | Worldwide |
| | Puumala | HFRS | *Cleothrianomys glareolus* | Europe |
| Sigmodontinae | Sin Nombre | HCPS | *Peromyscus maniculatus* (grassland form) | West and Central US and Canada |
| | Monongahela | HCPS | *P. maniculatus* (forest form) | Eastern US and Canada |
| | New York | | *P. leucopus* (eastern halotype) | Eastern US |
| | Blue River | HCPS | *P. leucopus* (SN/NW halotypes) | Central US |
| | Bayou | HCPS | *Oryzomys palustris* | Southwestern US |
| | Black Creek Canal | HCPS | *Sigmondon hispidus* (eastern form) | Florida |
| | Muleshoe | | *S. hispidus* (western form) | Southern US |
| | Cano Delgadito | | *S. alstoni* | Venezuela |
| | Andes | HCPS | *O. longicaudatus* | Argentina and Chile |
| | Oran | HCPS | *O. longicaudatus* | NW Argentina |
| | Lechiguanas | HCPS | *O. flavescens* | Central Argentina |
| | Bermejo | | *O. chacoensis* | NW Argentina |
| | Hu39694 | HCPS | Unknown | Central Argentina |
| | Pergamno | | *Akadon azarae* | Central Argentina |
| | Maciel | | *Bolomys abscurus* | Central Argentina |
| | Laguna Negra | HCPS | *Calomys laucha* | Paraguay and Bolivia |
| | Juquitiba | HCPS | Unknown | Brazil |
| | Rio Mamore | | *Oligoryzomys microtis* | Boliva and Peru |
| | El Moro Canyon | | *Reithrodontomys megalotis* | Western US and Mexico |
| | Rio Segundo | | *R. mexicanus* | Costa Rica |
| Arvicolinae | Propect Hill | | *Microtus pennsylvanicus* | N America |
| | Bloodland Lake | | *M. ochrogaster* | N America |
| | Prospect Hill-like | | *M. pennsylvanicus/ montanus/ochrogster* | N America |
| | Isla Vista | | *M. californicus* | Western US and Mexico |

Significant strides have been made in the management of hantavirus infection, but successful management requires that patients be diagnosed before the immediate preagonal stage of illness. Advances in tertiary care management have occurred that may reduce mortality due to hantavirus infection. However, since infection progresses very rapidly, these advances are likely to affect the prognosis only of those patients for whom a diagnosis can be made in a timely manner. A method for rapid detection of hantavirus antibodies appropriate for a rural setting and that could be applied during the early stages of illness could improve the prospects for early intervention.

Several assays have been attempted for the timely diagnosis of hantavirus infection. For example, a variety of formats for serologic diagnosis of hantavirus infection have been employed including bead agglutination, immunofluorescence and immunoprecipitation assays using laboratory-cultivated viruses, hemagglutination inhibition, plaque- and focus-reduction neutralization assays, and ELISA formats (Lee et al., *J. Infect. Dis.* (1978) 137:298-308; Lee et al., *J. Infect. Dis.* (1982) 146:638-644; Lee et al., *J. Infect. Dis.* (1982) 146:645-651; Lundkvist et al., *Clin. Diagnos. Lab. Immunol.* (1995) 2:82-86; Chu et al., *Virology* (1994) 198: 196-204; Elgh et al., *J. Med. Virol* (1995) 45:146-150).

Strip immunoblot assays have also been used in an attempt at efficient diagnosis of hantavirus infection (see, e.g., Hjelle et al., *J. Clin. Microbiol.* (1997) 35:600-608; Bharadwaj et al., *J. Infect. Dis.* (2000) 182:43-48; Yee, et al., *J. Wildl. Dis.*

(2003) 39:271-277). However, a universal assay for identifying multiple strains of hantaviruses is not currently available.

The wide-spread availability of an accurate, efficient and rapid assay for hantavirus infection would be highly desirable and could save a considerable number of lives.

SUMMARY OF THE INVENTION

The present invention provides a simple, accurate and efficient method for diagnosing hantavirus infection, as well as for determining the type of hantavirus present. The methods allow the rapid detection, e.g., in less than one hour, of hantavirus infection caused by several hantaviruses, such as hantaviruses from more than one hantavirus serotype. If infection is detected, the individual can be given appropriate treatment in adequate time to prevent death. The method utilizes N and/or G1 antigens and/or antibodies directed against these antigens from at least six different hantavirus serotypes, including HTNV, PUUV, SEOV, DOBV, SNV and ANDV. The assays provide a rapid and reliable diagnostic test and are suitable for use in facilities with relatively unsophisticated laboratory capabilities. Moreover, the assays can be used to screen wild rodents for hantavirus infection in order to determine if a particular rodent population is infected with the virus, thereby preventing infection in laboratory workers, field crews and others who work with and encounter wild rodents.

Recombinant techniques can be used to produce the products described herein to provide protein preparations devoid of other molecules normally present, such as other viral contaminants and harmful proteins.

Accordingly, in one embodiment, the invention is directed to a method of detecting hantavirus antibodies in a biological sample. The method comprises:

(a) contacting the biological sample with at least six hantavirus recombinant antigens, wherein the at least six hantavirus recombinant antigens comprise a combination of G1 and/or N antigens from hantavirus serotypes Hantaan (HTNV), Puumala (PUUV), Seoul (SEOV), Dobrava (DOBV), Sin Nombre (SNV) and Andes (ANDV) wherein at least one recombinant antigen from each of the serotypes is present, the contacting performed under conditions which allow hantavirus antibodies, when present in the biological sample, to bind to at least one of the G1 or N antigens to form an antibody/antigen complex; and (b) detecting the presence or absence of the antibody/antigen complex, thereby detecting the presence or absence of hantavirus antibodies in the sample. The at least six hantavirus recombinant antigens can be any combination of G1 and N antigens as long as at least one antigen from at least six hantavirus serotypes, viz. Hantaan (HTNV), Puumala (PUUV), Seoul (SEOV), Dobrava (DOBV), Sin Nombre (SNV) and Andes (ANDV), is present. In a preferred embodiment, the at least six hantavirus recombinant antigens are all N antigens.

In additional embodiments, the invention is directed to an immunodiagnostic test kit for detecting hantavirus infection. The test kit comprises:

(a) at least six hantavirus recombinant antigens, wherein the at least six hantavirus recombinant antigens comprise a combination of G1 and/or N antigens from hantavirus serotypes Hantaan (HTNV), Puumala (PUUV), Seoul (SEOV), Dobrava (DOBV), Sin Nombre (SNV) and Andes (ANDV) wherein at least one antigen from each of the serotypes is present;

(b) and instructions for conducting the immunodiagnostic test.

In a preferred embodiment, the at least six hantavirus recombinant antigens are all N antigens.

In further embodiments, the invention is directed to a method of detecting hantavirus antigens in a biological sample. The method comprises:

(a) contacting the biological sample with at least six different antibodies, wherein each of said antibodies is specific for at least one of six hantavirus antigens, wherein the six hantavirus antigens comprise a combination of G1 and/or N antigens from hantavirus serotypes Hantaan (HTNV), Puumala (PUUV), Seoul (SEOV), Dobrava (DOBV), Sin Nombre (SNV) and Andes (ANDV), wherein at least one antibody specific for at least one antigen from each of the serotypes is present, wherein the contacting is done under conditions which allow hantavirus antigens, when present in the biological sample, to bind to the antibodies to form an antibody/antigen complex; and (b) detecting the presence or absence of the antibody/antigen complex, thereby detecting the presence or absence of hantavirus antigens in the sample.

In certain embodiments of the above method, the antibodies are monoclonal antibodies.

In yet an additional embodiment, the invention is directed to an immunodiagnostic test kit for detecting hantavirus infection. The test kit comprises:

(a) at least six different antibodies, wherein each of the antibodies is specific for at least one of six hantavirus antigens, wherein the six hantavirus antigens comprise a combination of G1 and/or N antigens from hantavirus serotypes Hantaan (HTNV), Puumala (PUUV), Seoul (SEOV), Dobrava (DOBV), Sin Nombre (SNV) and Andes (ANDV), wherein at least one antibody specific for at least one antigen from each of the serotypes is present; and (b) instructions for conducting the immunodiagnostic test.

In certain embodiments of the above immunodiagnostic test kit, the antibodies are monoclonal antibodies.

In additional embodiments, the invention is directed to a solid support comprising at least six hantavirus recombinant antigens, wherein the at least six hantavirus recombinant antigens comprise a combination of G1 and/or N antigens from hantavirus serotypes Hantaan (HTNV), Puumala (PUUV), Seoul (SEOV), Dobrava (DOBV), Sin Nombre (SNV) and Andes (ANDV) wherein at least one antigen from each of the serotypes is present. The solid support can be a nitrocellulose strip.

In certain embodiments, the solid support further comprises at least one anti-human immunoglobulin antibody, such one or more antibodies selected from the group consisting of an anti-human IgM antibody, an anti-human IgG antibody and an anti-human IgA antibody, wherein the hantavirus antigens and the anti-human immunoglobulin antibody are immobilized in discrete positions on the solid support.

In additional embodiments, the solid support further comprises at least two internal controls, wherein one of the controls defines the lower detection limit for a positive result in an immunoassay using the solid support and the other control defines a highly positive result in an immunoassay using the solid support.

In further embodiments, the invention is directed to an immunodiagnostic test kit for detecting hantavirus. The test kit comprises:

(a) a solid support as described above; and (b) instructions for conducting the immunodiagnostic test.

In additional embodiments, the invention is directed to a method of detecting the presence of hantavirus antibodies in a biological sample. The method comprises:

(a) providing a biological sample;
(b) providing a solid support as described above;
(c) contacting the biological sample with the solid support, under conditions which allow hantavirus antibodies, if present in the biological sample, to bind with at least one of the hantavirus antigens to form an antibody/antigen complex; and
(d) detecting the presence of the antibody/antigen complex, thereby detecting the presence of hantavirus antibodies in the biological sample.

In certain embodiments, the method above further comprises:
(e) removing unbound hantavirus antibodies;
(f) providing one or more moieties capable of associating with the antibody/antigen complex; and
(g) detecting the presence of the one or more moieties, thereby detecting the presence of hantavirus antibodies in the biological sample.

In certain embodiments, the one or more moieties comprises a detectably labeled hantavirus antigen. In these and other embodiments, the detectable label can be an enzyme.

In yet an additional embodiment, the invention is directed to a method of preparing a blood supply comprising whole blood, platelets, plasma or serum, substantially free of hantavirus. The method comprises:
(a) screening aliquots of whole blood, platelets, plasma or serum from collected blood samples by the method of any one of the methods described above;
(b) eliminating any samples in which a hantavirus antigen or a hantavirus antibody is detected; and
(c) combining samples in which neither a hantavirus antigen or a hantavirus antibody is detected to provide a blood supply substantially free of hantavirus.

In any of the methods above, the biological sample can be from a human blood sample. Additionally, In any of the embodiments above, the G1 antigen(s) can comprise an amino acid sequence corresponding to the amino acid sequence of SEQ ID NO:40. The G1 antigen(s) can be one or more antigens comprising an amino acid sequence selected from the group consisting of SEQ ID NO:14, SEQ ID NO:16, SEQ ID NO:18, SEQ ID NO:20, SEQ ID NO:22, SEQ ID NO:24, SEQ ID NO:42, SEQ ID NO:43, SEQ ID NO:44, SEQ ID NO:45, SEQ ID NO:46 and SEQ ID NO:47.

Additionally, the N antigen(s) can comprise an amino acid sequence corresponding to the amino acid sequence of SEQ ID NO:39. In other embodiments, the N antigen(s) can be one or more antigens comprising an amino acid sequence selected from the group consisting of SEQ ID NO:26, SEQ ID NO:28, SEQ ID NO:30, SEQ ID NO:32, SEQ ID NO:34, SEQ ID NO:36, SEQ ID NO:48, SEQ ID NO:49, SEQ ID NO:50, SEQ ID NO:51, SEQ ID NO:52 and SEQ ID NO:53.

The G1 antigen(s) can comprise an amino acid sequence corresponding to the amino acid sequence of SEQ ID NO:40 and the N antigen(s) comprises an amino acid sequence corresponding to the amino acid sequence of SEQ ID NO:39. In additional embodiments, the G1 antigen(s) is one or more antigens comprising an amino acid sequence selected from the group consisting of SEQ ID NO:14, SEQ ID NO:16, SEQ ID NO:18, SEQ ID NO:20, SEQ ID NO:22, SEQ ID NO:24, SEQ ID NO:42, SEQ ID NO:43, SEQ ID NO:44, SEQ ID NO:45, SEQ ID NO:46 and SEQ ID NO:47, and the N antigen(s) is one or more antigens comprising an amino acid sequence selected from the group consisting of SEQ ID NO:26, SEQ ID NO:28, SEQ ID NO:30, SEQ ID NO:32, SEQ ID NO:34 and SEQ ID NO:36.

In additional embodiments, at least one G1 antigen is present from each of hantavirus serotypes HTNV, PUUV, SEOV, DOBV, SNV and ANDV, and at least one N antigen is present from each of hantavirus serotypes HTNV, PUUV, SEOV, DOBV, SNV and ANDV.

In further embodiments, at least one N antigen is present from each of hantavirus serotypes HTNV, PUUV, SEOV, DOBV, SNV and ANDV.

These and other embodiments of the subject invention will readily occur to those of skill in the art in view of the disclosure herein.

BRIEF DESCRIPTION OF THE FIGURES

FIGS. 1A and 1B (SEQ ID NOS:1 and 2) show a representative nucleotide sequence for the full-length M segment of HTNV isolate 76-118, encoding the G1 and G2 envelope proteins (FIG. 1A) and the corresponding amino acid sequence for the G1 protein (FIG. 1B).

FIGS. 2A and 2B (SEQ ID NOS:3 and 4) show a representative nucleotide sequence for the full-length M segment of PUUV isolate CG1820, encoding the G1 and G2 envelope proteins (FIG. 2A) and the corresponding amino acid sequence for the G1 protein (FIG. 2B).

FIGS. 3A and 3B (SEQ ID NOS:5 and 6) show a representative nucleotide sequence for the full-length M segment of SEOV isolate 80-39, encoding the G1 and G2 envelope proteins (FIG. 3A) and the corresponding amino acid sequence for the G1 protein (FIG. 3B).

FIGS. 4A and 4B (SEQ ID NOS:7 and 8) show a representative nucleotide sequence for the full-length M segment of DOBV, encoding the G1 and G2 envelope proteins (FIG. 4A) and the corresponding amino acid sequence for the G1 protein (FIG. 4B).

FIGS. 5A and 5B (SEQ ID NOS:9 and 10) show a representative nucleotide sequence for the full-length M segment of SNV isolate NM H10, encoding the G1 and G2 envelope proteins (FIG. 5A) and the corresponding amino acid sequence for the G1 protein (FIG. 5B).

FIGS. 6A and 6B (SEQ ID NOS:11 and 12) show a representative nucleotide sequence for the full-length M segment of ANDV isolate Chile-9717869, encoding the G1 and G2 envelope proteins (FIG. 6A) and the corresponding amino acid sequence for the G1 protein (FIG. 6B).

FIGS. 7A and 7B (SEQ ID NOS:13 and 14) show the nucleotide sequence (FIG. 7A) and the corresponding amino acid sequence (FIG. 7B) of a representative HTNV G1 peptide for use in the subject assays.

FIGS. 8A and 8B (SEQ ID NOS:15 and 16) show the nucleotide sequence (FIG. 8A) and the corresponding amino acid sequence (FIG. 8B) of a representative PUUV G1 peptide for use in the subject assays.

FIGS. 9A and 9B (SEQ ID NOS:17 and 18) show the nucleotide sequence (FIG. 9A) and the corresponding amino acid sequence (FIG. 9B) of a representative SEOV G1 peptide for use in the subject assays.

FIGS. 10A and 10B (SEQ ID NOS:19 and 20) show the nucleotide sequence (FIG. 10A) and the corresponding amino acid sequence (FIG. 10B) of a representative DOBV G1 peptide for use in the subject assays.

FIGS. 11A and 11B (SEQ ID NOS:21 and 22) show the nucleotide sequence (FIG. 11A) and the corresponding amino acid sequence (FIG. 11B) of a representative SNV G1 peptide for use in the subject assays.

FIGS. 12A and 12B (SEQ ID NOS:23 and 24) show the nucleotide sequence (FIG. 12A) and the corresponding amino acid sequence (FIG. 12B) of a representative ANDV G1 peptide for use in the subject assays.

FIGS. 13A and 13B (SEQ ID NOS:25 and 26) show a representative nucleotide sequence (FIG. 13A) and the corresponding amino acid sequence (FIG. 13B) of a full-length HTNV N from isolate 76-118 for use in the subject assays.

FIGS. 14A and 14B (SEQ ID NOS:27 and 28) show a representative nucleotide sequence (FIG. 14A) and the corresponding amino acid sequence (FIG. 14B) of a full-length PUUV N from isolate CG1820 for use in the subject assays.

FIGS. 15A and 15B (SEQ ID NOS:29 and 30) show a representative nucleotide sequence (FIG. 15A) and the corresponding amino acid sequence (FIG. 15B) of a full-length SEOV N from isolate 80-39 for use in the subject assays.

FIGS. 16A and 16B (SEQ ID NOS:31 and 32) show a representative nucleotide sequence (FIG. 16A) and the corresponding amino acid sequence (FIG. 16B) of a full-length DOBV N for use in the subject assays.

FIGS. 17A and 17B (SEQ ID NOS:33 and 34) show a representative nucleotide sequence (FIG. 17A) and the corresponding amino acid sequence (FIG. 17B) of a full-length SNV N from isolate NM H10 for use in the subject assays.

FIGS. 18A and 18B (SEQ ID NOS:35 and 36) show a representative nucleotide sequence (FIG. 18A) and corresponding amino acid sequence (FIG. 3018B) of a full-length ANDV N from isolate Chile-9717869 for use in the subject assays.

FIGS. 19A and 19B (SEQ ID NOS:37 and 38) show a representative human SOD nucleotide and amino acid sequence, respectively, used in the SOD fusions with the G1 and N antigens, described in the examples. The fused SOD sequence includes amino acids 1-158 of FIG. 19B (nucleotides 1-489 of FIG. 19A) which includes five amino acids of non-SOD sequence on the C-terminus (TRQNK, SEQ ID NO:41) in order to provide a restriction site for cloning.

FIG. 20 (SEQ ID NO:42) shows the amino acid sequence of a representative SOD/HTNV G1 fusion for use in the subject assays.

FIG. 21 (SEQ ID NO:43) shows the amino acid sequence of a representative SOD/PUUV G1 fusion for use in the subject assays.

FIG. 22 (SEQ ID NO:44) shows the amino acid sequence of a representative SOD/SEOV G1 fusion for use in the subject assays.

FIG. 23 (SEQ ID NO:45) shows the amino acid sequence of a representative SOD/DOBV G1 fusion for use in the subject assays.

FIG. 24 (SEQ ID NO:46) shows the amino acid sequence of a representative SOD/SNV G1 fusion for use in the subject assays.

FIG. 25 (SEQ ID NO:47) shows the amino acid sequence of a representative SOD/ANDV G1 fusion for use in the subject assays.

FIG. 26 (SEQ ID NO:48) shows the amino acid sequence of a representative SOD/HTNV N fusion for use in the subject assays.

FIG. 27 (SEQ ID NO:49) shows the amino acid sequence of a representative SOD/PUUV N fusion for use in the subject assays.

FIG. 28 (SEQ ID NO:50) shows the amino acid sequence of a representative SOD/SEOV N fusion for use in the subject assays.

FIG. 29 (SEQ ID NO:51) shows the amino acid sequence of a representative SOD/DOBV N fusion for use in the subject assays.

FIG. 30 (SEQ ID NO:52) shows the amino acid sequence of a representative SOD/SNV N fusion for use in the subject assays.

FIG. 31 (SEQ ID NO:53) shows the amino acid sequence of a representative SOD/ANDV N fusion for use in the subject assays.

DETAILED DESCRIPTION OF THE INVENTION

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology*, 3rd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

I. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a G1 polypeptide" includes a mixture of two or more such polypeptides, and the like.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

The term "antigen" when used with reference to the various hantavirus polypeptides for use with the present invention, refers to an N, G1, etc., polypeptide, whether native, recombinant or synthetic, which includes one or more epitopes that recognize hantavirus antibodies and which are derived from any of the various isolates of the hantavirus strain in question. Accordingly, a "hantavirus antigen" is an antigen derived from any of the hantavirus serotypes, strains and isolates, including, without limitation, any of the various isolates of the Murinae, Sigmodontinae and Arvicolinae subfamilies. For example, an SNV antigen will be derived from any of the various Sin Nombre virus isolates, such as the prototype New Mexico SNV isolate, 3H226, California isolates, British Columbia isolates, etc. Similarly, an SEOV antigen will be derived from any of the various Seoul virus isolates, and so on. Additional antigens for use in the present invention can be derived from other HPS- and HFRS-associated hantaviruses, including, but not limited to, Sin Nombre virus (SNV; also known as Four Corners virus and Muerto Canyon virus); Andes virus (ANDV); New York virus (NYV); Black Creek Canal virus (BCCV); Bayou virus (BAYV); Hantaan virus (HTNV), Puumala virus (PUUV), Seoul virus (SEOV), and Dobrava-Belgrade (DOBV) virus. The genomic sequences for these viruses are known and several antigenic sequences for use with the present invention are detailed further below.

The antigen in question need not include the full-length amino acid sequence of the reference molecule but can include only so much of the molecule as necessary in order for the polypeptide to react with the appropriate hantavirus antibodies. Thus, only one or few epitopes of the reference molecule need be present. Furthermore, the antigen may comprise a fusion protein between the full-length reference molecule or a fragment of the reference molecule, and another protein such as another hantavirus antigen and/or a protein that does not disrupt the reactivity of the hantavirus antigen. It is readily apparent that the antigen may therefore comprise the full-length sequence, fragments, truncated and partial sequences, as well as analogs, muteins and precursor forms of the reference molecule. The term also intends deletions, additions and substitutions to the reference sequence, so long as the antigen retains the ability to react with hantavirus antibodies.

In this regard, natural variation will occur from isolate to isolate within a particular hantavirus strain. Thus, the term is intended to encompass such variation and, in particular, an antigen that varies in its amino acid composition by not more than about 20 number percent, more preferably by not more than about 10 to 15 number percent, and most preferably, by not more than about 5 number percent, from the reference antigen. Proteins having substantially the same amino acid sequence as the reference molecule, but possessing minor amino acid substitutions that do not substantially affect the antibody binding capabilities of the antigen, are therefore within the definition of the reference polypeptide.

An antigen "derived from" a hantavirus serotype, strain or isolate intends an antigen which comprises a sequence of an antigen encoded by the reference hantavirus genome. Typically, the antigen includes one or more epitopes, and will generally have an amino acid sequence substantially homologous to the reference polypeptide, as defined below. Thus, the term "derived from" is used to identify the original source of a molecule but is not meant to limit the method by which the molecule is made which can be, for example, by chemical synthesis or recombinant means.

The terms "analog" and "mutein" refer to biologically active derivatives of the reference molecule, that retain desired activity, such as immunoreactivity in assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity and which are "substantially homologous" to the reference molecule as defined below. A number of conserved and variable regions are known between the various isolates and, in general, the amino acid sequences of epitopes derived from these regions will have a high degree of sequence homology, e.g., amino acid sequence homology of more than 50%, generally more than 60%-70%, when the two sequences are aligned. The term "mutein" refers to peptides having one or more peptide mimics ("peptoids"). Preferably, the analog or mutein has at least the same immunoreactivity as the native molecule. Methods for making polypeptide analogs and muteins are known in the art and are described further below.

The terms "analog" and "mutein" also encompasses purposeful mutations that are made to the reference molecule. Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the antigen of interest may include up to about 5-10 conservative or non-conservative amino acid substitutions, or even up to about 15-25, 50 or 75 conservative or non-conservative amino acid substitutions, or any integer between 5-75, so long as the desired function of the molecule remains intact. One of skill in the art can readily determine regions of the molecule of interest that can tolerate change by reference to Hopp/Woods and Kyte-Doolittle plots, well known in the art.

By "fragment" is intended an antigen consisting of only a part of the intact full-length polypeptide sequence and structure. The fragment can include a C-terminal deletion an N-terminal deletion, and/or an internal deletion of the native polypeptide. Representative G1 fragments for use in the present assays are shown in FIGS. 7-12 herein. By "immunogenic fragment" is meant a fragment of a hantavirus polypeptide that includes one or more epitopes and thus elicits one or more of the immunological responses described herein. An "immunogenic fragment" of a particular hantavirus protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein.

By "N antigen" is meant an antigen, as defined above, that is derived from the nucleocapsid protein of the hantavirus in question. The DNA and corresponding amino acid sequences for various hantavirus N proteins are known. For example, the nucleotide sequence and corresponding amino acid sequence for representative N antigens from HTNV, PUUV, SEOV, DOBV, SNV and ANDV are shown in FIGS. 13-18, respectively. Additionally, the S segments encoding the N proteins of a large number of isolates have been deposited with GenBank and are described further below. Additional sequences are described in International Publication No. WO 95/00648, published Jan. 5, 1995. Hjelle, et al., *J. Virol* (1994) 68:592-596 describes the amino acid sequences of N antigens derived from SNV, Prospect Hill Virus (PHV) and PUUV.

As explained above, N antigens for use in the present assays include the full-length or substantially full-length proteins, as well as fragments, fusions or mutants of the proteins, which include one or more epitopes such that reactivity with antibodies present in a biological sample from an individual with the particular hantavirus infection in question is retained. For example, N antigens for use in the assays described herein may be a recombinant fusion between the full-length SNV N sequence with another protein, such as another hantavirus antigen, and/or a fusion with a protein that aids in recombinant expression, such as with a 50 kDa *E. coli* maltose binding protein, or a human or yeast superoxide dismutase (SOD) protein. A representative immunoreactive fragment of the N protein useful in the present assays is a 43 amino acid amino terminal-proximal segment corresponding to the sequence of amino acids found at positions 17-59 of the N polypeptide, numbered relative to SNV NM 10 and having the amino acid sequence QLVTARQKLKDAERAVELDPD-DVNKSTLQSRRAAVSALETKLG (SEQ ID NO:39). This fragment includes an immunodominant epitope of the N protein and antibodies directed against this epitope are cross-reactive with N proteins from PUUV, SEOV and HTNV (see, e.g., Yamada et al., *J. Virol.* (1995) 69:1939-1943; and International Publication No. WO 95/06250, published Mar. 2, 1995). Thus, this fragment, as well as larger fragments including this sequence, will find use in the assays herein. For descriptions of epitopes of the N protein see, also, Lundkvist et al., *Clin. Diag. Lab. Immunol.* (1995) 2:82-86; and Gott et al., *Virus Res.* (1991) 19:1-16.

By "G1 antigen" is meant an antigen, as defined above, that is derived from the envelope glycoprotein known as G1, of the hantavirus in question. The DNA and corresponding amino acid sequences for various hantavirus G1 proteins are known. Representative G1 regions are shown in FIGS. 1-6 herein. Additionally, the M segments, encoding the G1 proteins from a number of isolates have been deposited with GenBank and are described further below. As explained above, G1 antigens for use in the present assays include the full-length or substantially full-length proteins, as well as fragments, fusions or mutants of the proteins, which include one or more epitopes such that reactivity with antibodies present in a biological sample from an individual with the particular hantavirus infection in question is retained. G1 antigens used in the assays described herein include fusions between the G1 antigen in question and a human superoxide dismutase (SOD) sequence shown in FIG. 19, to facilitate recombinant expression of the antigen. A number of additional representative immunoreactive fragments of the G1 protein from a number of hantavirus serotypes are shown in FIGS. 7-12 herein. Another representative immunoreactive fragment of the G1 protein is a 31 amino acid peptide mapped to a segment between amino acids 59 and 89, numbered relative to SNV NM H10 and having the amino acid sequence LKIESSCN-FDLHVPATTTQKYNQVDWTKKSS (SEQ ID NO:40). This portion of the G1 protein constitutes an immunoreactive linear epitope recognized by SNV antibodies from various SNV isolates (Jenison et al., *J. Virol.* (1994) 68:3000-3006). This fragment, as well as larger fragments including this sequence, will find use in the assays herein.

By "immunogenic" sequence of a hantavirus antigen is meant a molecule that includes an amino acid sequence with at least one hantavirus epitope such that the molecule is capable of reacting with antibodies directed against the hantavirus in question, as well as stimulating the production of antibodies in an appropriate host. By "epitope" is meant a site on an antigen to which specific B cells and/or T cells respond, rendering the hantavirus epitope in question capable of reacting with hantavirus antibodies present in a biological sample, as well as stimulating antibody production. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids or more.

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1985) *Proc. Natl. Acad. Sci. USA* 82:178-182; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

An "immunogenic composition" is a composition that comprises at least one immunogenic polypeptide (e.g., an N and/or G1 hantavirus antigen).

"Substantially purified" generally refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different isolates or strains of a hantavirus which antigenic determinants are not necessarily identical due to sequence variation, but which occur in equivalent positions in the hantavirus sequence in question. In general the amino acid sequences of equivalent antigenic determinants will have a high degree of sequence homology, e.g., amino acid sequence homology of more than 30%, usually more than 40%, such as more than 60%, and even more than 80-90% homology, when the two sequences are aligned.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

An "antibody" intends a molecule that specifically binds to an epitope of interest present in an antigen. By "specifically binds" is meant that the antibody recognizes and interacts with the epitope in a "lock and key" type of interaction to form a complex between the antigen and antibody, as opposed to non-specific binding that might occur between the antibody and, for instance, the test substrate with which the antibody is reacted. Thus, an anti-hantavirus G1 antibody is a molecule that specifically binds to an epitope of a hantavirus G1 protein. The term "antibody" as used herein includes antibodies obtained from both polyclonal and monoclonal preparations, as well as, the following: hybrid (chimeric) antibody molecules (see, for example, Winter et al., *Nature* (1991) 349: 293-299; and U.S. Pat. No. 4,816,567); F(ab')2 and F(ab) fragments; Fv molecules (non-covalent heterodimers, see, for example, Inbar et al., *Proc Natl Acad Sci USA* (1972) 69:2659-2662; and Ehrlich et al., *Biochem* (1980) 19:4091-4096); single-chain Fv molecules (sFv) (see, for example, Huston et al., *Proc Natl Acad Sci USA* (1988) 85:5879-5883); dimeric and trimeric antibody fragment constructs; minibodies (see, e.g., Pack et al., *Biochem* (1992) 31:1579-1584; Cumber et al., *J Immunology* (1992) 149B:120-126); humanized antibody molecules (see, for example, Riechmann et al., *Nature* (1988) 332:323-327; Verhoeyan et al., *Science* (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments, as well as chimeric and humanized homogeneous antibody populations, that exhibit immunological binding properties of the parent monoclonal antibody molecule.

As used herein, a "solid support" refers to a solid surface to which a macromolecule, e.g., protein, polypeptide, peptide, polynucleotide can be attached, such as a magnetic bead, latex bead, microtiter plate well, glass plate, nylon, agarose, polyacrylamide, silica particle, nitrocellulose membrane, and the like.

"Immunologically reactive" means that the antigen in question will react specifically with anti-hantavirus antibodies present in a biological sample from a hantavirus-infected individual.

"Immune complex" intends the combination formed when an antibody binds to an epitope on an antigen.

As used herein, a "biological sample" refers to a sample of tissue or fluid isolated from a subject such as, but not limited to, blood, plasma, serum, fecal matter, urine, bone marrow, bile, spinal fluid, lymph fluid, cerebrospinal fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. The samples detailed above need not necessarily be in the form obtained directly from the source. For example, the sample can be treated prior to use, such as, for example, by heating, centrifuging, etc. prior to analysis.

As used herein, the terms "label" and "detectable label" refer to a molecule capable of detection, including, but not limited to, radioactive isotopes, fluorescers, semiconductor nanocrystals, chemiluminescers, chromophores, enzymes, enzyme substrates, enzyme cofactors, enzyme inhibitors, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and α-β-galactosidase.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of novel diagnostic methods for accurately detecting hantavirus infection. The methods utilize hantavirus recombinant N and G1 antigens comprising immunodominant epitopes, and/or antibodies directed against these antigens, from at least six different hantavirus serotypes, including HTNV, PUUV, SEOV, DOBV, SNV and ANDV. In certain embodiments, the assays include, for example, six recombinant G1 antigens (and/or antibodies directed against six G1 antigens), one from each of the above serotypes, and/or six recombinant N antigens, one from each of the above serotypes. In alternative embodiments, the assay can include, for example, at least one recombinant N antigen derived from any one of these six serotypes, that produces antibodies that cross-react with one or more of the other five serotypes, and six recombinant G1 antigens, one from each of the six serotypes. For example, the assays can include an N antigen (and/or antibodies directed against the N antigen) from SNV. The assays will also include G1 antigens (and/or antibodies directed against G1 antigens), preferably from all six of the serotypes HTNV, PUUV, SEOV, DOBV, SNV and ANDV. Alternatively, the assay can include a G1 antigen (and/or antibodies thereto) from any one of these six serotypes, and six N antigens (and/or antibodies thereto) from each of these six serotypes. In another embodiment, the assay can include, for example, three G1 antigens (and/or antibodies thereto) from three of the six serotypes, and three N antigens (and/or antibodies thereto) from the other three of the six serotypes. Alternatively, the assay can include two G1 antigens (and/or antibodies thereto) and four N antigens (and/or antibodies thereto), or four G1 antigens (and/or antibodies thereto) and two N antigens (and/or antibodies thereto), or one G1 antigen (and/or antibodies thereto) and five N antigens (and/or antibodies thereto), or five G1 antigens (and/or antibodies thereto) and one N antigen (and/or antibodies thereto), or four G1 antigens (and/or antibodies thereto) and four N antigens (and/or antibodies thereto), or five G1 antigens (and/or antibodies thereto and five N antigens (and/or antibodies thereto), and so on. It is readily apparent that any combination of recombinant G1 and N antigens (and/or antibodies thereto) can be used so long as the six serotypes HTNV, PUUV, SEOV, DOBV, SNV and ANDV are represented.

The assays of the present invention can also utilize additional hantavirus antigens, derived from any of the various hantavirus strains described in Table 1 or others subsequently identified.

The use of hantavirus N and/or G1 antigens (and/or antibodies thereto) from the six serotypes HTNV, PUUV, SEOV, DOBV, SNV and ANDV, optionally in combination with other hantavirus proteins and/or antibodies, allows for the diagnosis of infection caused by any of the various known hantavirus serotypes. Moreover, the assays can be adapted such that the particular hantavirus serotype causing infection can be identified. For example, biological samples from patients infected with a variety of HPS- and HFRS-associated hantaviruses react with SNV N antigens, but not necessarily with SNV G1 antigens. Thus, the presence of reactivity with an SNV N antigen and the absence of reactivity with an SNV G1 antigen, indicates infection with a hantavirus other than SNV, and the like. It is readily apparent that a wide variety of antigens and combinations of antigens (or antibodies directed against these antigens) can be used in the present diagnostic assays.

The methods are useful for detecting hantavirus infection in humans, as well as in rodent populations. The methods can detect hantavirus infection in blood samples, including without limitation, in whole blood, serum and plasma. Thus, the methods can be used to diagnose hantavirus infection in a subject, such as a human or rodent subject, as well as to detect hantavirus contamination in donated blood samples. Aliquots from individual donated samples or pooled samples can be screened for the presence of hantavirus and those samples or pooled samples contaminated with hantavirus can be eliminated before they are combined. In this way, a blood supply substantially free of hantavirus contamination can be provided.

In order to further an understanding of the invention, a more detailed discussion is provided below regarding hantaviruses, as well as various hantavirus antigens and antibodies for use in the subject compositions and methods.

Hantavirus Antigens

As explained above, the hantavirus family of viruses belongs to the Bunyavirus genus and the viruses are enveloped, minus-sense RNA viruses. The RNA of the viral genome is tripartite, consisting of three fragments generally designated as S, M and L for small, medium and large genome fragments, respectively. The M segment encodes two envelope glycoproteins, termed G1 and G2, in a single open reading frame. The S segment encodes the nucleocapsid protein, termed N and the L segment of the genome encodes an RNA-dependent RNA polymerase.

Several distinct hantaviruses are found in association with specific rodent hosts worldwide (see, Table 1). As explained above, N and/or G1 antigens derived from at least six major hantavirus serotypes, HTNV, PUUV, SEOV, DOBV, SNV and ANDV, will find use herein. Sequences for N and G1 antigens from numerous isolates identified as belonging to these serotypes, and the nucleic acid sequences encoding these antigens, are known. Representative sequences from which G1 antigens can be derived are depicted in FIGS. 1-12 herein. Although the G1 antigens depicted in the figures include an N-terminal methionine, the G1 peptides for use herein need not include this methionine, especially if produced by synthetic means. The G1 antigens for use herein can include the full-length G1 protein or immunogenic fragments of the G1 protein. Particularly useful are fragments that include at least the region corresponding to the 31 amino acid sequence represented by amino acids 59-89, numbered relative to SNV NM H10 (LKIESSCNFDLHVPATTTQKYN-QVDWTKKSS (SEQ ID NO:40). This region of the G1 protein constitutes an immunoreactive linear epitope and is found in each of the G1 immunogenic fragments shown in FIGS. 7-12 herein. This sequence is not the same in the six hantavirus serotypes of interest herein. Thus, it is to be understood that an amino acid sequence from a non-SNV hantavirus that "corresponds" to this sequence is an amino acid segment from the non-SNV hantavirus that falls in the same region and displays homology to this sequence but does not necessarily show 100% identity to this sequence. The corresponding region in the other five hantavirus serotypes is readily identifiable from a review of FIGS. 7-12 herein.

Immunogenic G1 antigens comprising a sequence of amino acids corresponding to the sequence of amino acids shown in SEQ ID NO:40 can include, for example, 31 amino acids, up to the full-length of the G1 molecule, such as 31-500 amino acids, preferably 31-250 amino acids, even more preferably 31-150 amino acids, such as 31 to 50 . . . 60 . . . 70 . . . 75, 76, 77, 78, 79, 80, 81, 82, 83, 84, 85, 86 . . . 90 . . . 100 . . . 200 . . . 300 . . . 400 . . . 500, up to the full-length G1 molecule, or any integer within these ranges. Moreover, the G1 antigens for use herein may lack all or a portion of the transmembrane binding domain and/or the cytoplasmic tail found in the C-terminus of the envelope. Thus, the present invention contemplates the use of envelope polypeptides which retain the transmembrane binding domain and cytoplasmic tail, as well as antigens which lack all or a portion of the transmembrane binding domain and/or the cytoplasmic tail, as well as adjacent portions of the G1 protein. The location of such domains can be readily determined using computer programs and algorithms well known in the art, such as the Kyte-Doolittle technique, Kyte et al., *J. Mol. Biol.* (1982) 157:105-132.

Additional sequences from which the G1 antigens can be derived are well known. For example, G1 sequences can be derived from any of the various HTNV sequences such as those sequences deposited with NCBI under accession numbers NC_005219, AF345636, D25532, D25529, D00377, D00376, AF288645, AF366569, AF035831, Y00386, U38177, U37729, M14627 and L08753. G1 sequences can be derived from any of the various SNV sequences such as those sequences deposited with NCBI under accession numbers L37903, L25783, AF030552, AF030551 and U02471. G1 sequences can be derived from any of the various ANDV sequences such as those sequences deposited with NCBI under accession numbers NC_003467 and AF291703. G1 sequences can be derived from any of the various SEOV sequences such as those sequences deposited with NCBI under accession numbers AF458104, AB027521, AF288654, AF288652, AF288650 and S47716. G1 sequences can be derived from any of the various PUUV sequences such as those sequences deposited with NCBI under accession numbers NC_005223, AY526218, U14136, U22418, L08754, L08755, X61034, X55129 and M29979. G1 sequences can be derived from any of the various DOBV sequences such as those sequences deposited with NCBI under accession numbers NC_005234, AJ410616, AY168578, AY168577 and L33685.

Representative sequences from which N antigens can be derived are depicted in FIGS. 13-18 herein. As described above for the G1 antigens, the N antigens may or may not include an N-terminal methionine. The N antigens for use herein can include the full-length N protein or immunogenic fragments of the N protein. Particularly useful are fragments that include at least the region corresponding to the 43 amino acid sequence found at positions 17-59 of the N polypeptide, numbered relative to SNV NM H10 (QLVTARQKLKDAER-AVELDPDDVNKSTLQSRRAAVSALETKLG (SEQ ID NO:39). This region of the N protein includes an immunodominant epitope and antibodies directed against this epitope are cross-reactive with N proteins from PUUV, SEOV and HTNV.

This sequence is not the same in the six hantavirus serotypes of interest herein. Thus, it is to be understood that an amino acid sequence from a non-SNV hantavirus that "corresponds" to this sequence is an amino acid segment from the non-SNV hantavirus that falls in the same region and displays homology to this sequence but does not necessarily show 100% identity to this sequence. The corresponding region in the other five hantavirus serotypes is readily identifiable from a review of FIGS. 13-18 herein.

Immunogenic N antigens comprising a sequence of amino acids corresponding to the sequence of amino acids shown in SEQ ID NO:39 can include, for example, 43 amino acids, up to the full-length of the N molecule, such as 43-350 amino acids, preferably 43-300 amino acids, more preferably 43-200 amino acids, even more preferably 43-100 amino acids, such as 43 to 60 . . . 70 . . . 80 . . . 90 . . . 100 . . . 200 . . . 300 . . . 400, up to the full-length N molecule, or any integer within these ranges.

Additional sequences from which the N antigens can be derived are well known. For example, N sequences can be derived from any of the various HTNV sequences such as those sequences deposited with NCBI under accession numbers AB127998, AB027101, AB027523, AB027097, D25533, AF288646, AF288644, AF427324, AF427323, AF427322, AF427320, AF427319, AF427318, AF366568, AY017064, AF321095, AF321094, AF288296, U37768 and M14626. N sequences can be derived from any of the various SNV sequences such as those sequences deposited with NCBI under accession numbers NC_005216, L37904, L25784, L33816, L33683 and U02474. N sequences can be derived from any of the various ANDV sequences such as those sequences deposited with NCBI under accession numbers NC_003466, AF325966, AF0044660 and AF291702. N sequences can be derived from any of the various SEOV sequences such as those sequences deposited with NCBI under accession numbers NC_005236, AF488708, AF488707, AY273791, AB027522, AF329390, AF288655, AF288653, AF288643, AF406965, AY006465. N sequences can be derived from any of the various PUUV sequences such as those sequences deposited with NCBI under accession numbers NC_005224, AY526219, AJ314601, AJ314600, AJ314599, AJ314598, AJ314597, AF442613, AF367071, AF367070, AF367068, AF367067, AF367066, AF367065, AF367064, AJ277030, AJ277076, AJ277075, AJ277034, AJ277033, AJ277032, AJ277031, AJ238791, AJ238790, AJ238789, AJ238788, X61035, AB010731, AB010730, U14137, AF294652, U22423, L08804, L11347 and M32750. N sequences can be derived from any of the various DOBV sequences such as those sequences deposited with NCBI under accession numbers NC_005233, AJ616854, AJ410619, AJ410615, AJ131673, AJ131672, AJ269550, AJ269549, AJ009775, AJ009773, AY168576 and L41916.

The recombinant N and G1 antigens can be provided as discrete products or as fusions of the various N and G1 antigens, with or without other hantavirus antigens from one of more of these six serotypes, as well as with antigens derived from serotypes in addition to HTNV, PUUV, SEOV, DOBV, SNV and ANDV. By way of example, fusions can comprise G1 antigens from the six serotypes above. This fusion can be used alone or in combination with a second fusion including one or more N antigens from one or more of these six serotypes. Similarly, fusions can comprise N antigens from the six serotypes above and this fusion can be used alone or in combination with a second fusion including one or more G1 antigens from one or more of these six serotypes. Alternatively, all N and G1 antigens can be provided in a single fusion, or multiple fusions. It is readily apparent that fusion proteins of the subject invention can take any number of forms so long as N and/or G1 antigens from HTNV, PUUV, SEOV, DOBV, SNV and ANDV are present. If a fusion is produced, the polypeptides need not be organized in the same order as found in the native virus. Thus, for example, a G1 polypeptide can be fused to the N-terminus or C-terminus of an N polypeptide, etc. Other possible fusion proteins include a fusion of a human or yeast superoxide dismutase (SOD) protein, or fragment of the SOD protein, with a hantavirus G1 and/or N polypeptide. For examples of recombinant proteins expressed as human SOD fusion antigens, see Barr et al., *Vaccine* (1987) 5:90-101; Pichuantes et al., *Proteins Struct. Fuct. Genet.* (1989) 6:324-327; Pichuantes et al., *J. Biol. Chem.* (1990) 23:13890-13898.

Antigens for use with the present invention can be obtained using standard techniques. For example, the hantavirus antigens are conveniently generated using recombinant methods, well known in the art. See, e.g., International Publication No. WO 95/00648, published Jan. 5, 1995; International Publication No. WO 95/06240, published Mar. 2, 1995; and Hjelle, et al., *J. Virol* (1994) 68:592-596, for descriptions of the recombinant production of hantavirus antigens.

Oligonucleotide probes can be devised based on the known sequences of the hantavirus genome and used to probe genomic or cDNA libraries for hantavirus genes encoding for the antigens useful in the present invention. The genes can then be further isolated using standard techniques and, if desired, restriction enzymes employed to mutate the gene at desired portions of the full-length sequence.

Similarly, hantavirus genes can be isolated directly from infected tissue using known techniques, such as by phenol extraction (see, e.g., International Publication No. WO 95/00648, published Jan. 5, 1995), and the sequence can be further manipulated to produce any desired alterations. See, e.g., Sambrook et al., supra, for a description of techniques used to obtain and isolate DNA. Finally, the genes encoding the hantavirus antigens can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259: 6311.

Polynucleotides can comprise coding sequences for the various polypeptides which occur naturally or can include artificial sequences which do not occur in nature. These polynucleotides can be ligated to form a coding sequence for a fusion protein, if desired, using standard molecular biology techniques.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements. The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

If present, the signal sequence can be the native leader found in association with the hantavirus polypeptide of interest. For example, if the hantavirus polypeptide being expressed is a G1 antigen, all or a portion of the native G1 leader sequence can be included. Alternatively, a heterologous signal sequence can be present which can increase the efficiency of secretion. A number of representative leader sequences are known in the art and include, without limitation, the yeast α-factor leader, the TPA signal peptide, the Ig signal peptide, and the like. Sequences for these and other leader sequences are well known in the art.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the polypeptide of interest. Mutants or analogs of hantavirus polypeptides for use in the subject compositions may be prepared by the deletion of a portion of the sequence encoding the molecule of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci. USA* 79:6409.

In order to facilitate recombinant expression, the molecule of interest can be expressed as a fusion protein, such as a fusion with, e.g., a 50 kDa *E. coli* maltose binding protein, a fusion with a human or yeast superoxide dismutase (SOD) or fragment thereof, or as a ubiquitin fusion protein.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The hantavirus antigens are used herein as diagnostics to detect the presence of reactive antibodies directed against the virus in a biological sample. Furthermore, the antigens can be used to determine which hantavirus type is responsible for infection. The antigens may also be used to produce antibodies for use in diagnostics.

Hantavirus Antibodies

The hantavirus antigens can be used to produce hantavirus-specific polyclonal and monoclonal antibodies. Hantavirus-specific polyclonal and monoclonal antibodies specifically bind to hantavirus antigens. Polyclonal antibodies can be produced by administering the hantavirus antigen to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against hantavirus-specific epitopes present in the proteins can also be readily produced. Normal B cells from a mammal, such as a mouse (see, e.g., Kohler and Milstein, *Nature* (1975) 256:495-497), or a rabbit (see, e.g., U.S. Pat. No. 5,675,063 incorporated herein by reference in its entirety), immunized with a hantavirus antigen, can be fused with, for example, HAT-sensitive mouse myeloma cells to produce hybridomas. Hybridomas producing hantavirus-specific antibodies can be identified using RIA or ELISA and isolated by cloning in semi-solid agar or by limiting dilution. Clones producing hantavirus-specific antibodies are isolated by another round of screening.

It may be desirable to provide chimeric antibodies. Chimeric antibodies composed of human and non-human amino acid sequences may be formed from the mouse monoclonal antibody molecules to reduce their immunogenicity in humans (Winter et al. (1991) *Nature* 349:293; Lobuglio et al. (1989) *Proc. Nat. Acad. Sci. USA* 86:4220; Shaw et al. (1987) *J. Immunol* 138:4534; and Brown et al. (1987) *Cancer Res.* 47:3577; Riechmann et al. (1988) *Nature* 332:323; Verhoeyen et al. (1988) *Science* 239:1534; and Jones et al. (1986) *Nature* 321:522; EP Publication No. 519,596, published 23 Dec. 1992; and U.K. Patent Publication No. GB 2,276,169, published 21 Sep. 1994).

Antibody molecule fragments, e.g., $F(ab')_2$, Fv, and sFv molecules, that are capable of exhibiting immunological binding properties of the parent monoclonal antibody molecule can be produced using known techniques. Inbar et al. (1972) *Proc. Nat. Acad. Sci. USA* 69:2659; Hochman et al.

(1976) *Biochem* 15:2706; Ehrlich et al. (1980) *Biochem* 19:4091; Huston et al. (1988) *Proc. Nat. Acad. Sci. USA* 85(16):5879; and U.S. Pat. Nos. 5,091,513 and 5,132,405, to Huston et al.; and 4,946,778, to Ladner et al.

In the alternative, a phage-display system can be used to expand monoclonal antibody molecule populations in vitro. Saiki, et al. (1986) *Nature* 324:163; Scharf et al. (1986) *Science* 233:1076; U.S. Pat. Nos. 4,683,195 and 4,683,202; Yang et al. (1995) *J Mol Biol* 254:392; Barbas, III et al. (1995) *Methods: Comp. Meth Enzymol* 8:94; Barbas, III et al. (1991) *Proc Natl Acad Sci USA* 88:7978.

Once generated, the phage display library can be used to improve the immunological binding affinity of the Fab molecules using known techniques. See, e.g., Figini et al. (1994) *J. Mol. Biol.* 239:68. The coding sequences for the heavy and light chain portions of the Fab molecules selected from the phage display library can be isolated or synthesized, and cloned into any suitable vector or replicon for expression. Any suitable expression system can be used, including those described above.

Antibodies which are directed against hantavirus epitopes, are particularly useful for detecting the presence of hantavirus or hantavirus antigens in a sample, such as a serum sample from a hantavirus-infected human. An immunoassay for a hantavirus antigen may utilize one antibody or several antibodies either alone or in combination with hantavirus antigens. An immunoassay for a hantavirus antigen may use, for example, a monoclonal antibody directed towards a hantavirus epitope, a combination of monoclonal antibodies directed towards epitopes of one hantavirus polypeptide, monoclonal antibodies directed towards epitopes of different hantavirus polypeptides, polyclonal antibodies directed towards the same hantavirus antigen, polyclonal antibodies directed towards different hantavirus antigens, or a combination of monoclonal and polyclonal antibodies. Immunoassay protocols may be based, for example, upon competition, direct reaction, or sandwich type assays using, for example, labeled antibody and are described further below. The labels may be, for example, fluorescent, chemiluminescent, or radioactive.

The hantavirus antibodies may further be used to isolate hantavirus particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind hantavirus particles or antigens from a biological sample, such as blood or plasma. The bound hantavirus particles or antigens are recovered from the column matrix by, for example, a change in pH.

Hantavirus Diagnostic Assays

As explained above, the immunogenic hantavirus antigens and antibodies to the antigens can be used in assays to identify hantavirus infection. Typically, the presence of hantavirus in a biological sample will be determined by the presence of antibodies to hantavirus in the sample, although in appropriate cases the presence of the viral proteins may be detected and used as an indicator of hantavirus in the sample. The reagents can be used for detecting hantavirus in blood samples, including without limitation, in whole blood, serum and plasma. The antigens and antibodies can be used to detect hantavirus infection in a subject, such as a human or rodent subject, as well as to detect hantavirus contamination in donated blood samples. Thus, aliquots from individual donated samples or pooled samples can be screened for the presence of hantavirus and those samples or pooled samples contaminated with hantavirus can be eliminated before they are combined. In this way, a blood supply substantially free of hantavirus contamination can be provided. By "substantially free of hantavirus" is meant that the presence of hantavirus is not detected using the assays described herein, preferably using the strip immunoblot assay described more fully below.

Assays for use herein include Western blots; agglutination tests; enzyme-labeled and mediated immunoassays, such as ELISAs; biotin/avidin type assays; radioimmunoassays; immunoelectrophoresis; immunoprecipitation, strip immunoblot assays, and the like. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody or antigen in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

In one aspect of the invention, the hantavirus G1 and/or N antigens from at least the six hantavirus serotypes, HTNV, PUUV, SEOV, DOBV, SNV and ANDV, are used for capture or detection or both of anti-hantavirus antibodies in a sample. In another aspect of the invention, antibodies to the hantavirus antigens can be used for the capture or detection or both of hantavirus antigens in a sample. By "capture" of an analyte (i.e., anti-hantavirus antibodies or hantavirus antigens in a sample) is meant that the analyte can be separated from other components of the sample by virtue of the binding of the capture molecule. Typically, the capture molecule is associated with a solid support, either directly or indirectly. Typically, the detection molecule is associated with a detectable label, either directly or indirectly.

Typically, a solid support is first reacted with a solid phase component (e.g., the hantavirus G1 and/or N antigens from at least the six hantavirus serotypes, HTNV, PUUV, SEOV, DOBV, SNV and ANDV and/or anti-hantavirus antibodies) under suitable binding conditions such that the component is sufficiently immobilized to the support. Sometimes, immobilization to the support can be enhanced by first coupling to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigen or antibody to the support include polysaccharides, polylactic acids, polyglycolic acids, polymeric amino acids, amino acid copolymers, and the like. Such molecules and methods of coupling these molecules are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing the ligand component (i.e., hantavirus antigens or antibodies) under suitable binding conditions. After washing to remove any non-bound ligand, a secondary binder moiety can be added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with the hantavirus G1 and/or N antigens from at least the six hantavirus serotypes, HTNV, PUUV, SEOV, DOBV, SNV and ANDV, and/or antibodies according to the present invention. A biological sample containing or suspected of containing either anti-hantavirus immunoglobulin molecules or hantavirus antigens is then added to the coated wells. After a period of incubation sufficient to allow antigen-antibody binding, the plate(s) can be washed to remove unbound moieties and a detectably labeled secondary binding molecule added. The secondary binding molecule is allowed to react with any captured sample, the plate washed and the presence of the secondary binding molecule detected using methods well known in the art.

In one particular format, an ELISA antigen sandwich format is used. In this case, the solid support is coated with the hantavirus G1 and/or N antigens from at least the six hantavirus serotypes, HTNV, PUUV, SEOV, DOBV, SNV and ANDV. The sample is then contacted with the support under conditions that allow anti-hantavirus antibodies, if present, to bind one or more or the hantavirus antigens to form an antigen/antibody complex. Unbound reagents are removed and an enzymatically labeled antigen that reacts with the bound antigen/antibody complex, such as a labeled hantavirus N and/or G1 antigen, is added. An enzyme substrate is used to generate a signal.

In another format, the solid support is coated with species-specific anti-isotypic antibodies (e.g., anti-human IgM antibodies, anti-human IgG antibodies, anti-human IgA antibodies, etc). The support is then contacted with the sample under conditions that allow binding of antibodies present in the sample to the anti-isotypic antibodies. Unbound antibodies can be removed and the presence of bound anti-hantavirus antibodies is detected using labeled hantavirus antigens of the present invention. The label will typically be an enzyme label, e.g., a HRP, AP.

In another embodiment, the presence of bound hantavirus ligands from a biological sample can be readily detected using a secondary binder comprising an antibody directed against the antibody ligands. A number of anti-human immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Other formats for detection of anti-hantavirus antibodies in a sample are known and the combination of hantavirus antigens of the present invention can be used with any known format that employs a hantavirus antigen. See, e.g., Lee et al., *J. Infect. Dis.* (1978) 137:298-308; Lee et al., *J. Infect. Dis.* (1982) 146:638-644; Lee et al., *J. Infect. Dis.* (1982) 146:645-651; Lundkvist et al., *Clin. Diagnos. Lab. Immunol.* (1995) 2:82-86; Chu et al., *Virology* (1994) 198:196-204; Elgh et al., *J. Med. Virol* (1995) 45:146-150; Hjelle et al., *J. Clin. Microbiol.* (1997) 35:600-608; Bharadwaj et al., *J. Infect. Dis.* (2000) 182:43-48; Yee, et al., *J. Wildl. Dis.* (2003) 39:271-277).

The hantavirus G1 and/or N antigens from at least the six hantavirus serotypes, HTNV, PUUV, SEOV, DOBV, SNV and ANDV, can be used in an IgM capture ELISA as follows. Anti-human IgM antibodies (e.g., goat anti-human IgM antibodies) are attached to a solid support, the support is contacted with a sample to be tested for the presence of human IgM to hantavirus, under conditions that would allow the binding of the anti-hantavirus IgM, if present, to one or more of the anti-human IgM antibodies attached to the solid support, to form antibody/antibody complexes. The hantavirus G1 and/or N antigens from at least the six hantavirus serotypes, HTNV, PUUV, SEOV, DOBV, SNV and ANDV are added under conditions that would allow binding to the anti-hantavirus IgM in the antibody/antibody complexes forming an antibody/antibody/antigen complex. Unbound antigens are removed and detectably labeled anti-hantavirus antibodies are added under conditions that would allow binding to the bound antigens. The presence of IgM to hantavirus in the sample is determined by the presence of detectably labeled anti-hantavirus antibodies to the bound anti-human IgM Ab/human anti-hantavirus IgM/antigen complexes attached to the solid support. Alternatively, the hantavirus antigens themselves may be detectably labeled, this dispensing with the need for detectably labeled anti-hantavirus antibodies.

The hantavirus G1 and/or N antigens from at least the six hantavirus serotypes, HTNV, PUUV, SEOV, DOBV, SNV and ANDV can also be used in an indirect IgG ELISA as follows. Antibodies specific for antigens are attached to a solid support, the support is contacted with the hantavirus G1 and/or N antigens from at least the six hantavirus serotypes, HTNV, PUUV, SEOV, DOBV, SNV and ANDV under conditions that would allow binding to the anti-hantavirus antibodies bound to the support to form antibody/antigen complexes. Unbound antigens are removed and the support is contacted with a sample to be tested for the presence of human IgG to hantavirus under conditions that would allow binding of human anti-hantavirus IgG, if present, to the antigens in the antibody/antigen complexes. The presence of bound anti-hantavirus IgG can be detected using a detectably labeled anti-human IgG antibody.

While some of the foregoing assay formats are termed "ELISA" (Enzyme Linked ImmunoSorbant Assay) assays, it will be apparent to one of skill in the art that the use of a detectable label other than an "enzyme linked" binding moiety is possible and may be desirable in many situations. Other suitable detectable labels are described herein and are well known in the art.

Assays can also be conducted in solution, such that the hantavirus antigens or antibodies and ligands specific for these molecules form complexes under precipitating conditions. In one particular embodiment, the molecules can be attached to a solid phase particle (e.g., an agarose bead or the like) using coupling techniques known in the art, such as by direct chemical or indirect coupling. The coated particle is then contacted under suitable binding conditions with a biological sample suspected of containing hantavirus antibodies or antigens. Cross-linking between bound antibodies causes the formation of complex aggregates which can be precipitated and separated from the sample using washing and/or centrifugation. The reaction mixture can be analyzed to determine the presence or absence of complexes using any of a number of standard methods, such as those immunodiagnostic methods described above.

In yet a further embodiment, an immunoaffinity matrix can be provided, wherein, for example, a polyclonal population of antibodies from a biological sample suspected of containing hantavirus antibodies is immobilized to a substrate. An initial affinity purification of the sample can be carried out using immobilized antigens. The resultant sample preparation will thus only contain anti-hantavirus moieties, avoiding potential nonspecific binding properties in the affinity support. A number of methods of immobilizing immunoglobulins (either intact or in specific fragments) at high yield and good retention of antigen binding activity are known in the art. Once the immunoglobulin molecules have been immobilized to provide an immunoaffinity matrix, labeled molecules are contacted with the bound antibodies under suitable binding conditions. After any non-specifically bound hantavirus antigen has been washed from the immunoaffinity support, the presence of bound antigen can be determined by assaying for label using methods known in the art.

In a particularly preferred embodiment of the invention, a strip immunoblot assay (SIA) is used to detect hantavirus antibodies in a biological sample using the hantavirus G1 and/or N antigens from at least the six hantavirus serotypes, HTNV, PUUV, SEOV, DOBV, SNV and ANDV, immobilized on the test strip. SIA techniques are well known in the art and combine traditional western and dot blotting techniques, e.g., the RIBA® (Chiron Corp., Emeryville, Calif.) SIA. In these assays, the hantavirus antigens are immobilized as individual, discrete portions, e.g., as bands or dots, on a membranous support. Thus, by "discretely immobilized" on a membrane support is meant that the antigens are present as separate components and not mixed, such that reactivity or lack thereof with each of the antigens present can be assessed. A biological sample suspected of containing antibodies to hantavirus is then reacted with the test membrane. Visualization of anti-hantavirus reactivity in the biological sample is accomplished using anti-human immunoglobulin enzyme-conjugates in conjunction with a colorimetric enzyme substrate. Internal controls, such as anti-human IgM antibody and anti-human IgG antibody, can also be present on the test membrane. The assay can be performed manually or used in an automated format.

Solid supports which can be used in the practice of the strip immunoblot assays include, but are not limited to, membrane supports derived from a number of primary polymers including cellulose, polyamide (nylon), polyacrylonitrile, polyvinylidene difluoride, polysulfone, polypropylene, polyester, polyethylene and composite resins consisting of combinations or derivatives of the above. Particularly preferred are supports derived from cellulose, such as nitrocellulose membranes, as well as nylon membranes. The substrate generally includes the desired membrane with an inert plastic backing as a support.

The amount of antigen applied to the membrane varies, depending on the antigen in question. Generally, the antigen will be applied to the strip in an amount of about 20-500 ng/strip, preferably 50-250 ng/strip, more preferably 75-150 ng/strip. One of skill in the art can readily determine the amount of antigen necessary to produce a useable result. Alternatively, two concentrations of the antigens can be present, such as a low concentration and a high concentration. Thus, for example, an SNV N antigen can be provided in a concentration as specified above, as well as in one or more additional bands, in a concentration of about, e.g., 25-200 ng, such as 50-150 ng, e.g., 100 ng/strip. The high level control will be present in an amount sufficiently higher to give a highly positive result, such as at 200-500 ng, particularly 250-350 ng, e.g., 300 ng/strip. It is apparent that the concentration of antigen to be applied to the test strip will vary depending on the specific antigen used and can be readily determined by one of skill in the art.

The anti-immunoglobulin antibodies, such as anti-human IgM antibody, anti-human IgG antibody and/or anti-human IgA antibody, can be present in a single concentration, or in two concentrations, one low and one high. For example, anti-IgG antibody can be present in a concentration of about 50-250 ng/ml, more preferably about 75-200 ng/ml and most preferably about 100-185 ng/ml. A higher concentration of anti-IgG antibody can also be present along with the low concentration of anti-IgG, to provide another internal control, such as at a concentration of about 400-1200 ng/ml, more preferably about 450-1000 ng/ml and most preferably about 500-950 ng/ml.

After reacting the membrane support with the desired antigens and Ig molecules, any non-immobilized solid-phase components are removed from the membrane by washing, and the membrane-bound components are then contacted with a biological sample suspected of containing antibodies to hantavirus, under suitable binding conditions. After washing to remove any non-bound antibodies, a secondary binder moiety is added under suitable binding conditions, where the secondary binder is capable of associating selectively with bound antibodies. The presence of the secondary binder can then be detected using techniques well known in the art.

In a particularly preferred embodiment, the presence of bound anti-hantavirus antigen ligands from a biological sample can be readily detected using a secondary binder comprising an antibody directed against the antibody ligands. A number of anti-human immunoglobulin (Ig) molecules are known in the art such as commercially available goat anti-human Ig or rabbit anti-human Ig. Ig molecules for use herein will be of the IgG, IgA or IgM type. The Ig molecules can be readily conjugated to a detectable enzyme label, such as horseradish peroxidase, glucose oxidase, β-galactosidase, alkaline phosphatase and urease, among others, using methods known to those of skill in the art. An appropriate enzyme substrate is then used to generate a detectable signal.

Furthermore, a conjugate against human heavy- and light-chain antibodies can be used to render the SIA capable of detecting both IgG and IgM responses. This design may serve to increase sensitivity of detection of antibody responses in the early stages of infection.

The above-described assay reagents, including hantavirus antigens and/or antibodies thereto, the solid supports with bound reagents, as well as other detection reagents, can be provided in kits, with suitable instructions and other necessary reagents, in order to conduct the assays as described above. The kit may also include control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Cloning and Expression of Hantavirus Recombinant G1 Proteins

The hantavirus G1 antigens shown in Table 2 were prepared as follows. Nucleotide fragments encoding recombinant G1 antigens including 80-83 amino acids of the G1 protein of HTNV, PUUV, SEOV, DOBV, SNV and ANDV were synthesized using a combination of oligonucleotides corresponding to the region of interest for each strain. The portion of the G1 protein sequence in the recombinant antigen is indicated in Table 2. These fragments were annealed, ligated and cloned into a subcloning vector and the correct nucleotide sequence was confirmed by DNA sequencing. The region of interest was excised by restriction endonuclease treatment and cloned along with the ADH2/GAPDH promoter fragment into pBS24.1. Plasmid pBS24.1 is a high copy number expression vector that has been extensively used to express a great variety of recombinant proteins (Pichuantes et al., *J. Biol. Chem.* (1990) 23:13890-13898; Pichuantes et al., "Expression of heterologous gene products in yeast." In: Cleland J L, Craik C, editors. Protein engineering: a guide to design and production (1996) New York, N.Y., Wiley-Liss, Inc., pp 129-161). It contains 2μ and inverted repeats (IR) sequences for autonomous replication, the α-factor terminator to ensure transcription termination, and the leu2-d and URA3, for selection. The β-lactamase gene for ampicillin resistance and the ColE1 origin of replication are also present in this vector for selection and autonomous replication in *Escherichia coli*.

For SOD fusion constructs, the region of interest was cloned into a genetically engineered pBS24.1 vector that already contained the ADH2/GAPDH promoter along with the human SOD gene. The nucleotide sequence and amino acid sequences of the human SOD used in the cloning of the hantavirus recombinant antigens is described in Hallewell et al., *Bio/Technology* (1987) 5:363-366. The resulting plasmids were transformed into *S. cerevisiae* strain AD3 and expression of the recombinant proteins was monitored by SDS-PAGE and immunoblot analysis. The various SOD/G1 fusions produced include the G1 sequences shown in FIGS. 7-12 fused to the C-terminus of the SOD sequence shown in FIG. 19. The SOD/G1 fusions are represented by SEQ ID NOS:42-47.

The following protocol was followed to produce the SOD fusions. Although this discussion details the production of the SNV G1/SOD fusion, the remaining fusions were produced in the same way. Since expression of extensive portions of the full-length G1 was hampered by instability and variable expression, a smaller (82-aa) portion of SNV G1 (residues 35-117 relative to the initiating methionine of isolate NM H10) was used in a fusion with the human superoxide dismutase (SOD) sequence shown in FIG. 19. The small G1 fragment was synthesized by PCR from pFCV-M-1275 (Yamada et al., *J. Virol* (1995) 69:1939-1943) using primers that introduced an NcoI site on the 5'-end and a SalI site and two stop codons on the 3'-end. The 268 bp NcoI/SalI-digested fragment was used to replace the 347 bp insert of pSOD/HIV2PR113 (Pichuantes et al., *J. Biol. Chem.* (1990) 265: 13890-13898), creating the construct pSOD/G1. A 603 bp StuI/SalI fragment of pSOD/G1 was ligated into the vector pSI1/PR179 (Pichuantes et al., *Proteins Struct. Funct. Genet.* (1989) 6:324-327) to provide the ADH2/GAPDH promoter. The 2093 bp BamHI/SalI cassette of the resulting construct was then introduced into the yeast expression vector pBS24.1 to create the final expression construct pSOD/SNV-G1. The protein was expressed as a 23 kD SOD-G1 fusion in the protease-deficient (prbl 1122, pep 4-3) *Saccharomyces cerevisiae* strain AB122 (Pichuantes et al., *Protein Engineering Principles and Practice* (1996) Chapter 5, pp. 129-161, Cleland and Craik, eds. Wiley-Liss, Inc., New York). The 82-aa portion of G1 expressed in this construct spans the immunodominant epitope and contains some additional flanking sequence. The sequence of the SNV G1 portion of the antigen is shown in FIG. 11B.

TABLE 2

Hantavirus G1 Antigens Expressed in *S. cerevisiae*

| Hantavirus Antigen | Amino Acid Sequence* | SEQ ID NO | Construct | Molecular Weight (kDa) |
|---|---|---|---|---|
| HTNV G1 | S34-H113 | 14 | Recombinant, nonfusion | 9.1 |
| SOD/HTNV G1 | S34-H113 | 42 | Recombinant, SOD fusion | 26.1 |
| PUUV G1 | R39-T121 | 16 | Recombinant, nonfusion | 9.4 |
| SOD/PUUV G1 | R39-T121 | 43 | Recombinant, SOD fusion | 26.4 |
| SEOV G1 | K32-H111 | 18 | Recombinant, nonfusion | 9.4 |
| SOD/SEOV G1 | K32-H111 | 44 | Recombinant, SOD fusion | 26.3 |
| DOBV G1 | N34-H116 | 20 | Recombinant, nonfusion | 9 |
| SOD/DOBV G1 | N34-H116 | 45 | Recombinant, SOD fusion | 26 |
| SNV G1 | G35-P117 | 22 | Recombinant, nonfusion | 9.3 |
| SOD/SNV G1 | G35-P117 | 46 | Recombinant, SOD fusion | 26.2 |
| ANDV G1 | G35-P117 | 24 | Recombinant, nonfusion | 9.3 |
| SOD/ANDV G1 | G35-P117 | 47 | Recombinant, SOD fusion | 26.2 |

*The amino acid sequences of the proteins produced also included a methionine (M) on the N-terminal end of the G1 sequences.

Example 2

Cloning and Expression of Hantavirus Recombinant N Proteins

The hantavirus N antigens shown in Table 3 were prepared as follows. The genes for the Hantavirus nucleocapsid proteins of PUUV, SEOV, SNV and ANDV were amplified by PCR using DNA from hantavirus recombinant plasmids as templates. The portions of the hantavirus N protein sequence in the recombinant proteins is indicated in Table 3. The nucleocapsid genes of HTNV and DOBV were chemically synthesized. Cloning and expression was performed essentially as described above. The various N antigens produced are shown in FIGS. 13-18 and the SOD sequence that was present directly contiguous to the N-terminus of the N antigen/SOD fusions is shown in FIG. 19.

TABLE 3

Hantavirus N Antigens Expressed in *S. cerevisiae*

| Hantavirus Antigen | Amino Acid Sequence* | SEQ ID NO | Construct | Molecular Weight (kDa) |
|---|---|---|---|---|
| HTNV N | M1-L429 | 26 | Recombinant, nonfusion | 48.5 |
| SOD/HTNV N | M1-L429 | 48 | Recombinant, SOD fusion | 65.3 |
| PUUV N | M1-I433 | 28 | Recombinant, nonfusion | 49.8 |
| SOD/PUUV N | M1-I433 | 49 | Recombinant, SOD fusion | 66.7 |
| SEOV N | M1-L429 | 30 | Recombinant, nonfusion | 48.4 |
| SOD/SEOV N | M1-L429 | 50 | Recombinant, SOD fusion | 65.3 |
| DOBV N | M1-L429 | 32 | Recombinant, nonfusion | 48.5 |
| SOD/DOBV N | M1-L429 | 51 | Recombinant, SOD fusion | 65.3 |
| SNV N | M1-L429 | 34 | Recombinant, nonfusion | 48.4 |
| SOD/SNV N | M1-L429 | 52 | Recombinant, SOD fusion | 65.4 |
| ANDV N | M1-L428 | 36 | Recombinant, nonfusion | 48.4 |
| SOD/ANDV N | M1-L428 | 53 | Recombinant, SOD fusion | 65.2 |

Example 3

Purification of Hantavirus Recombinant Proteins

The hantavirus proteins, recombinant produced as described above, were purified by lysing the transformed *S. cerevisiae* cells in lysis buffer (50 mM Tris, 0.15 M NaCl, 1 mM EDTA, pH 8) using a Dino-Mill apparatus. The lysate was washed several times with 1-3 M urea in lysis buffer and protein was solubilized by increasing the pH to 11.5 and then subjected to gel filtration chromatography. The purification of recombinant ANDV G and DOBV G proteins also included ammonium sulfate precipitation and solubilization with PBS, 0.1% SDS, 1 mM EDTA.

Example 4

Polyclonal Antibody Production Using the Hantavirus Recombinant Proteins

The purified recombinant SOD fused G1 antigens of HTNV, PUUV, SEOV, DOBV, SNV and ANDV and the recombinant non-fused N proteins of SEOV, DOBV, SNV and ANDV (see Tables 2 and 3 above) were used to produce rabbit polyclonal antibodies. Two rabbits were immunized and 50 ml of antiserum were produced. The polyclonal antibodies were then tested against the recombinant proteins using Western Blot analysis on a 4-20% Tris Glycine gel. The antibodies produced against each of the six G1 antigens were shown to be cross-reactive with the G1 antigens of the different subtypes. Similarly, the antibodies produced against each of the four N proteins were shown to be cross-reactive with the N antigens of the different subtypes.

Example 5

Strip Immunoblot Assay (SIA)

The recombinant G1 antigens and N antigens, with or without the SOD sequence, from the six serotypes, as described above are used in an SIA, such as the RIBA® test (Chiron Corp., Emeryville, Calif.). The membrane consists of nitrocellulose with an inert plastic backing as support. Six of the G1 antigens, one from each HTNV, PUUV, SEOV, DOBV, SNV and ANDV, and six of the N antigens, one from each of HTNV, PUUV, SEOV, DOBV, SNV and ANDV, are applied in discrete bands to nitrocellulose strips at concentrations of 75-150 ng/strip. As internal controls, additional bands contain purified human IgG at a low level, Level I (50-150 ng/strip) and high level, Level II (250-350 ng/strip).

The assay procedure is performed according to the manufacturer's instructions. All steps are performed at room temperature. Each strip is numbered and then placed in a separate tube to which is added a 1:50 dilution of human serum in a specimen diluent buffer (phosphate-buffered saline (PBS) with bovine protein stabilizers and detergents, 0.1% sodium azide and 0.05% gentamicin sulfate as preservatives). The tubes are rocked gently for 4 to 4.5 h, the solution removed by aspiration, and 1 ml of fresh diluent is added to each tube. The tubes are rocked for 30 minutes, the solution removed by aspiration and 1 ml of wash buffer made from wash buffer concentrate (50×) (phosphate-buffered detergent solution with 0.01% thimerosal as a preservative) is added to each tube. The contents of each tube are emptied into a single wash vessel and the strips are washed by swirling for 20 seconds. The wash buffer is decanted and 30 ml of fresh buffer added and the process repeated. Residual solution is removed by aspiration and 20 ml of conjugate solution (peroxidase-labeled goat anti-human IgG (heavy and light chains), with bovine protein stabilizers, containing 0.01% thimerosal as a preservative) is added. The vessel is rotated at 110 rpm for 9-11 minutes, the conjugate solution is decanted and the wash step is repeated three times. Residual solution is again removed by aspiration and 20 ml of substrate/developer (4-chloro-1-napthol in methanol/phosphate-buffered hydrogen peroxide) added, followed by rotation for 15-20 minutes at 110 rpm. The solution is decanted and the strips are washed twice in distilled water. Developed strips are placed face up on absorbent paper and allowed to dry for 30 minutes in the dark.

A serum is considered reactive against a given antigen only if reactivity is greater than or equal to the level I IgG control band, which is defined to represent a 1+ reactivity. A reactivity equivalent to the level II IgG control band is considered to represent a reactivity of 3+. Reactivity intensity intermediate between the level I and level II IgG control bands is considered to be 2+, and reactivity stronger than the level II band is considered to be 4+.

Thus, novel methods for detecting hantavirus infection are disclosed. Although preferred embodiments of the subject invention have been described in some detail, it is understood that obvious variations can be made without departing from the spirit and the scope of the invention as described herein.

The invention claimed is:

1. A method of detecting hantavirus antibodies in a biological sample, comprising:
    (a) contacting said biological sample with at least six hantavirus recombinant antigens, wherein the at least six hantavirus recombinant antigens comprise a combination of N antigens from hantavirus serotypes Hantaan (HTNV), Puumala (PUUV), Seoul (SEOV), Dobrava (DOBV), Sin Nombre (SNV) and Andes (ANDV) wherein at least one recombinant antigen from each of the serotypes is present, said contacting performed under conditions which allow hantavirus antibodies, when present in the biological sample, to bind to at least one of said N antigens to form an antibody/antigen complex, and wherein said N antigens comprise one or more amino acid sequences selected from the group consisting of SEQ ID NO:28, SEQ ID NO:32, SEQ ID NO:34, SEQ ID NO:48, SEQ ID NO:49, SEQ ID NO:50, SEQ ID NO:51, SEQ ID NO:52 and SEQ ID NO:53; and
    (b) detecting the presence or absence of said antibody/antigen complex, thereby detecting the presence or absence of hantavirus antibodies in said sample.

2. An immunodiagnostic test kit for detecting hantavirus infection, said test kit comprising:
    (a) at least six hantavirus recombinant antigens, wherein the at least six hantavirus recombinant antigens comprise a combination of N antigens from hantavirus serotypes Hantaan (HTNV), Puumala (PUUV), Seoul (SEOV), Dobrava (DOBV), Sin Nombre (SNV) and Andes (ANDV) wherein at least one N antigen from each of the serotypes is present, and wherein said N antigens comprise one or more amino acid sequences selected from the group consisting of SEQ ID NO:28, SEQ ID NO:32, SEQ ID NO:34, SEQ ID NO:48, SEQ ID NO:49, SEQ ID NO:50, SEQ ID NO:51, SEQ ID NO:52 and SEQ ID NO:53;
    (b) and instructions for conducting the immunodiagnostic test.

3. A solid support comprising at least six hantavirus recombinant antigens, wherein the at least six hantavirus recombinant antigens comprise a combination of N antigens from hantavirus serotypes Hantaan (HTNV), Puumala (PUUV), Seoul (SEOV), Dobrava (DOBV), Sin Nombre (SNV) and Andes (ANDV) wherein at least one N antigen from each of the serotypes is present, and wherein said N antigens comprise one or more amino acid sequences selected from the group consisting of SEQ ID NO:28, SEQ ID NO:32, SEQ ID NO:34, SEQ ID NO:48, SEQ ID NO:49, SEQ ID NO:50, SEQ ID NO:51, SEQ ID NO:52 and SEQ ID NO:53.

4. The solid support of claim 3, wherein the solid support is a nitrocellulose strip.

5. An immunodiagnostic test kit for detecting hantavirus, said test kit comprising:
    (a) a solid support according to claim 3; and
    (b) instructions for conducting the immunodiagnostic test.

6. A method of detecting the presence of hantavirus antibodies in a biological sample, said method comprising:

(a) providing a biological sample;

(b) providing a solid support according to claim 3;

(c) contacting said biological sample with said solid support, under conditions which allow hantavirus antibodies, if present in the biological sample, to bind with at least one of the hantavirus antigens to form an antibody/antigen complex; and (d) detecting the presence of the antibody/antigen complex, thereby detecting the presence of hantavirus antibodies in the biological sample.

7. The method of claim 6, further comprising:

(e) removing unbound hantavirus antibodies;

(f) providing one or more moieties capable of associating with said antibody/antigen complex; and (g) detecting the presence of said one or more moieties, thereby detecting the presence of hantavirus antibodies in the biological sample.

8. The method of claim 7, wherein said one or more moieties comprises a detectably labeled hantavirus antigen.

9. The method of claim 8, wherein the detectable label is an enzyme.

10. The method of any one of claim 1 and 6, wherein said biological sample is from a human blood sample.

11. An immunodiagnostic test kit for detecting hantavirus infection, said test kit comprising:

(a) at least six hantavirus recombinant antigens, wherein the at least six hantavirus recombinant antigens comprise the amino acid sequences of SEQ ID NO:26, SEQ ID NO:28, SEQ ID NO:30, SEQ ID NO:32, SEQ ID NO:34, and SEQ ID NO:36, respectively;

(b) and instructions for conducting the immunodiagnostic test.

12. A solid support comprising at least six hantavirus recombinant antigens, wherein the at least six hantavirus recombinant antigens comprise the amino acid sequences of SEQ ID NO:26, SEQ ID NO:28, SEQ ID NO:30, SEQ ID NO:32, SEQ ID NO:34, and SEQ ID NO:36, respectively.

* * * * *

SEQUENCE LISTING

<160> NUMBER OF SEQ ID NOS: 53

<210> SEQ ID NO 1
<211> LENGTH: 3616
<212> TYPE: DNA
<213> ORGANISM: Hantaan virus

<400> SEQUENCE: 1

```
tagtagtaga caccgcaaaa gaaagcagtc aatcagcaac atggggatat ggaagtggct      60
agtgatggcc agtttagtat ggcctgtttt gacactgaga aatgtctatg acatgaaaat     120
tgagtgcccc catacagtaa gttttgggga aaacagtgtg ataggttatg tagaattacc     180
ccccgtgcca ttggccgaca cagcacagat ggtgcctgag agttcttgta acatggataa     240
tcaccaatcg ttgaatacaa taacaaaata tacccaagta agttggagag gaaaggctga     300
tcagtcacag tctagtcaaa attcatttga gacagtgtcc actgaagttg acttgaaagg     360
aacatgtgtt ctaaaacaca aaatggtgga agaatcatac cgtagtagga aatcagtaac     420
ctgttacgac ctgtcttgca atagcactta ctgcaagcca acactataca tgattgtacc     480
aattcatgca tgcaatatga tgaaaagctg tttgattgca ttgggaccat acagagtaca     540
ggtggtttat gagagaagtt actgtatgac aggagtcctg attgaaggga aatgctttgt     600
cccagatcaa agtgtggtca gtattatcaa gcatgggatc tttgatattg caagtgttca     660
tattgtatgt ttctttgttg cagttaaagg gaatacttat aaaattttg aacaggttaa     720 gaaatccttt gaatcaacat gcaatgatac agagaataaa gtgcaaggat attatatttg     780
tattgtaggg ggaaactctg caccaatata tgttccaaca cttgatgatt tcagatccat     840
ggaagcattt acaggaatct tcagatcacc acatgggggaa gatcatgatc tggctggaga     900
agaaattgca tcttattcta tagtcggacc tgccaatgca aaagttcctc atagtgctag     960
ctcagataca ttgagcttga ttgcctattc aggtatacca tcttattctt cccttagcat    1020
cctaacaagt tcaacagaag ctaagcatgt attcagcccc gggttgttcc caaaacttaa    1080
tcacacaaat tgtgataaaa gtgccatacc actcatatgg actgggatga ttgatttacc    1140
```

-continued

```
tggatactac gaagctgtcc acccttgtac agttttttgc gtattatcag gtcctggggc    1200
atcatgtgaa gccttttctg aaggcgggat tttcaacata acctctccca tgtgcttagt    1260
gtcaaaacaa aatcgattcc ggttaacaga acagcaagtg aattttgtgt gtcagcgagt    1320
ggacatggac attgttgtgt actgcaacgg gcagaggaaa gtaatattaa caaaaactct    1380
agttattgga cagtgtatat atactataac aagcttattc tcattactac ctggagtagc    1440
acattctatt gctgttgaat tgtgtgtacc tgggttccat ggttgggcca cagctgctct    1500
gcttgttaca ttctgtttcg gatgggttct tataccagca attacattta tcatactaac    1560
agtcctaaag ttcattgcta atattttca cacaagtaat caagagaata ggctaaaatc     1620
agtacttaga aagataaagg aagagtttga aaaacaaaa ggctcaatgg tatgtgatgt     1680
ctgcaagtat gagtgtgaaa cctataaaga attaaaggca cacggggtat catgccccca    1740
atctcaatgt ccttactgtt ttactcattg tgaacccaca gaagcagcat tccaagctca    1800
ttacaaggta tgccaagtta ctcacagatt cagggatgat ctaaagaaaa ctgttactcc    1860
tcaaaatttt acaccaggat gttaccggac actaaattta tttagataca aaagcaggtg    1920
ctacatcttt acaatgtgga tatttcttct tgtcttagaa tccatactgt gggctgcaag    1980
tgcatcagag acaccattaa ctcctgtctg gaatgacaat gcccatgggg taggttctgt    2040
tcctatgcat acagatttag agcttgattt ctctttaaca tccagttcca agtatacata    2100
ccgtaggaag ttaacaaacc cacttgagga agcacaatcc attgacctac atattgaaat    2160
agaagaacag acaattggtg ttgatgtgca tgctctagga cactggtttg atggtcgtct    2220
taaccttaaa acatccttc actgttatgg tgcttgtaca aagtatgaat cccttggca     2280 tactgcaaag tgccattatg aaagagatta ccaatatgag acgagctggg gttgtaatcc    2340
atcagattgt cctggggtgg gcacaggctg tacagcatgt ggtttatacc tagatcaact    2400
gaaaccagtt ggtagtgctt ataaaattat cacaataagg tacagcagga gagtctgtgt    2460
tcagtttggg gaggaaaacc tttgtaagat aatagacatg aatgattgtt ttgtatctag    2520
gcatgttaag gtctgcataa ttggtacagt atctaaattc tctcagggtg ataccttatt    2580
gttttttgga ccgcttgaag gtggtggtct aatatttaaa cactggtgta catccacatg    2640
tcaatttggt gacccaggag atatcatgag tccaagagac aaaggttttt tatgccctga    2700
gtttccaggt agtttcagga agaaatgcaa ctttgctact acccctattt gtgagtatga    2760
tggaaatatg gtctcaggtt acaagaaagt gatggcgaca attgattcct tccaatcttt    2820
taatacaagc actatgcact tcactgatga aaggatagag tggaaagacc ctgatggaat    2880
gctaagggac catataaaca ttttagtaac gaaggacatt gactttgata accttggtga    2940
aaatccttgc aaaattggcc tacaaacatc ttctattgag ggggcctggg ttctggtgt     3000 ggggttcaca ttaacatgtc tggtatcact aacagaatgt cctacctttt tgacctcaat    3060
aaaggcttgt gataaggcta tctgttatgg tgcagagagt gtaacattga caagaggaca    3120
aaatacagtc aaggtatcag ggaaaggtgg ccatagtggt tcaacattta ggtgttgcca    3180
tgggagggac tgttcacaaa ttggactcca tgctgctgca cctcaccttg acaaggtaaa    3240
tgggatttct gagatagaaa atagtaaagt atatgatgat ggggcaccgc aatgtgggat    3300
aaaatgttgg tttgttaaat caggggaatg gatttcaggg atattcagtg gtaattggat    3360
tgtactcatt gtcctctgtg tatttctatt gttctccttg gttttactaa gcattctctg    3420 tccccgtaagg aagcataaaa aatcatagct aaattctgtg actatcctgt tcttatgtat    3480
```

```
agctttaaca tatatactaa tttttatatt ccagtatact ctatctaaca cactaaaaaa    3540
aatagtagct ttctaaccac aaaacttaga ttcttcttct gtatgatgtc ttaacatctt    3600
gcggtgtcta ctacta                                                    3616
```

<210> SEQ ID NO 2
<211> LENGTH: 1135
<212> TYPE: PRT
<213> ORGANISM: Hantaan virus

<400> SEQUENCE: 2

```
Met Gly Ile Trp Lys Trp Leu Val Met Ala Ser Leu Val Trp Pro Val
1               5                   10                  15

Leu Thr Leu Arg Asn Val Tyr Asp Met Lys Ile Glu Cys Pro His Thr
            20                  25                  30

Val Ser Phe Gly Glu Asn Ser Val Ile Gly Tyr Val Glu Leu Pro Pro
        35                  40                  45

Val Pro Leu Ala Asp Thr Ala Gln Met Val Pro Glu Ser Ser Cys Asn
    50                  55                  60

Met Asp Asn His Gln Ser Leu Asn Thr Ile Thr Lys Tyr Thr Gln Val
65                  70                  75                  80

Ser Trp Arg Gly Lys Ala Asp Gln Ser Gln Ser Ser Gln Asn Ser Phe
                85                  90                  95

Glu Thr Val Ser Thr Glu Val Asp Leu Lys Gly Thr Cys Val Leu Lys
            100                 105                 110

His Lys Met Val Glu Glu Ser Tyr Arg Ser Arg Lys Ser Val Thr Cys
        115                 120                 125

Tyr Asp Leu Ser Cys Asn Ser Thr Tyr Cys Lys Pro Thr Leu Tyr Met
    130                 135                 140

Ile Val Pro Ile His Ala Cys Asn Met Met Lys Ser Cys Leu Ile Ala
145                 150                 155                 160

Leu Gly Pro Tyr Arg Val Gln Val Val Tyr Glu Arg Ser Tyr Cys Met
                165                 170                 175

Thr Gly Val Leu Ile Glu Gly Lys Cys Phe Val Pro Asp Gln Ser Val
            180                 185                 190

Val Ser Ile Ile Lys His Gly Ile Phe Asp Ile Ala Ser Val His Ile
        195                 200                 205

Val Cys Phe Phe Val Ala Val Lys Gly Asn Thr Tyr Lys Ile Phe Glu
    210                 215                 220

Gln Val Lys Lys Ser Phe Glu Ser Thr Cys Asn Asp Thr Glu Asn Lys
225                 230                 235                 240

Val Gln Gly Tyr Tyr Ile Cys Ile Val Gly Gly Asn Ser Ala Pro Ile
                245                 250                 255

Tyr Val Pro Thr Leu Asp Asp Phe Arg Ser Met Glu Ala Phe Thr Gly
            260                 265                 270

Ile Phe Arg Ser Pro His Gly Glu Asp His Asp Leu Ala Gly Glu Glu
        275                 280                 285

Ile Ala Ser Tyr Ser Ile Val Gly Pro Ala Asn Ala Lys Val Pro His
    290                 295                 300

Ser Ala Ser Ser Asp Thr Leu Ser Leu Ile Ala Tyr Ser Gly Ile Pro
305                 310                 315                 320

Ser Tyr Ser Ser Leu Ser Ile Leu Thr Ser Ser Thr Glu Ala Lys His
                325                 330                 335

Val Phe Ser Pro Gly Leu Phe Pro Lys Leu Asn His Thr Asn Cys Asp
            340                 345                 350
```

```
Lys Ser Ala Ile Pro Leu Ile Trp Thr Gly Met Ile Asp Leu Pro Gly
            355                 360                 365

Tyr Tyr Glu Ala Val His Pro Cys Thr Val Phe Cys Val Leu Ser Gly
        370                 375                 380

Pro Gly Ala Ser Cys Glu Ala Phe Ser Glu Gly Gly Ile Phe Asn Ile
385                 390                 395                 400

Thr Ser Pro Met Cys Leu Val Ser Lys Gln Asn Arg Phe Arg Leu Thr
                405                 410                 415

Glu Gln Gln Val Asn Phe Val Cys Gln Arg Val Asp Met Asp Ile Val
            420                 425                 430

Val Tyr Cys Asn Gly Gln Arg Lys Val Ile Leu Thr Lys Thr Leu Val
        435                 440                 445

Ile Gly Gln Cys Ile Tyr Thr Ile Ser Leu Phe Ser Leu Leu Pro
    450                 455                 460

Gly Val Ala His Ser Ile Ala Val Glu Leu Cys Val Pro Gly Phe His
465                 470                 475                 480

Gly Trp Ala Thr Ala Ala Leu Leu Val Thr Phe Cys Phe Gly Trp Val
                485                 490                 495

Leu Ile Pro Ala Ile Thr Phe Ile Ile Leu Thr Val Leu Lys Phe Ile
            500                 505                 510

Ala Asn Ile Phe His Thr Ser Asn Gln Glu Asn Arg Leu Lys Ser Val
        515                 520                 525

Leu Arg Lys Ile Lys Glu Glu Phe Glu Lys Thr Lys Gly Ser Met Val
    530                 535                 540

Cys Asp Val Cys Lys Tyr Glu Cys Glu Thr Tyr Lys Glu Leu Lys Ala
545                 550                 555                 560

His Gly Val Ser Cys Pro Gln Ser Gln Cys Pro Tyr Cys Phe Thr His
                565                 570                 575

Cys Glu Pro Thr Glu Ala Ala Phe Gln Ala His Tyr Lys Val Cys Gln
            580                 585                 590

Val Thr His Arg Phe Arg Asp Asp Leu Lys Lys Thr Val Thr Pro Gln
        595                 600                 605

Asn Phe Thr Pro Gly Cys Tyr Arg Thr Leu Asn Leu Phe Arg Tyr Lys
    610                 615                 620

Ser Arg Cys Tyr Ile Phe Thr Met Trp Ile Phe Leu Leu Val Leu Glu
625                 630                 635                 640

Ser Ile Leu Trp Ala Ala Ser Ala Ser Glu Thr Pro Leu Thr Pro Val
                645                 650                 655

Trp Asn Asp Asn Ala His Gly Val Gly Ser Val Pro Met His Thr Asp
            660                 665                 670

Leu Glu Leu Asp Phe Ser Leu Thr Ser Ser Ser Lys Tyr Thr Tyr Arg
        675                 680                 685

Arg Lys Leu Thr Asn Pro Leu Glu Glu Ala Gln Ser Ile Asp Leu His
    690                 695                 700

Ile Glu Ile Glu Glu Gln Thr Ile Gly Val Asp Val His Ala Leu Gly
705                 710                 715                 720

His Trp Phe Asp Gly Arg Leu Asn Leu Lys Thr Ser Phe His Cys Tyr
                725                 730                 735

Gly Ala Cys Thr Lys Tyr Glu Tyr Pro Trp His Thr Ala Lys Cys His
            740                 745                 750

Tyr Glu Arg Asp Tyr Gln Tyr Glu Thr Ser Trp Gly Cys Asn Pro Ser
        755                 760                 765
```

-continued

Asp Cys Pro Gly Val Gly Thr Gly Cys Thr Ala Cys Gly Leu Tyr Leu
770             775                 780

Asp Gln Leu Lys Pro Val Gly Ser Ala Tyr Lys Ile Ile Thr Ile Arg
785             790                 795                 800

Tyr Ser Arg Arg Val Cys Val Gln Phe Gly Glu Glu Asn Leu Cys Lys
                805                 810                 815

Ile Ile Asp Met Asn Asp Cys Phe Val Ser Arg His Val Lys Val Cys
            820                 825                 830

Ile Ile Gly Thr Val Ser Lys Phe Ser Gln Gly Asp Thr Leu Leu Phe
        835                 840                 845

Phe Gly Pro Leu Glu Gly Gly Leu Ile Phe Lys His Trp Cys Thr
850                 855                 860

Ser Thr Cys Gln Phe Gly Asp Pro Gly Asp Ile Met Ser Pro Arg Asp
865             870                 875                 880

Lys Gly Phe Leu Cys Pro Glu Phe Pro Gly Ser Phe Arg Lys Lys Cys
                885                 890                 895

Asn Phe Ala Thr Thr Pro Ile Cys Glu Tyr Asp Gly Asn Met Val Ser
            900                 905                 910

Gly Tyr Lys Lys Val Met Ala Thr Ile Asp Ser Phe Gln Ser Phe Asn
        915                 920                 925

Thr Ser Thr Met His Phe Thr Asp Glu Arg Ile Glu Trp Lys Asp Pro
930             935                 940

Asp Gly Met Leu Arg Asp His Ile Asn Ile Leu Val Thr Lys Asp Ile
945                 950                 955                 960

Asp Phe Asp Asn Leu Gly Glu Asn Pro Cys Lys Ile Gly Leu Gln Thr
                965                 970                 975

Ser Ser Ile Glu Gly Ala Trp Gly Ser Gly Val Gly Phe Thr Leu Thr
            980                 985                 990

Cys Leu Val Ser Leu Thr Glu Cys Pro Thr Phe Leu Thr Ser Ile Lys
        995                 1000                1005

Ala Cys Asp Lys Ala Ile Cys Tyr Gly Ala Glu Ser Val Thr Leu
    1010            1015            1020

Thr Arg Gly Gln Asn Thr Val Lys Val Ser Gly Lys Gly His
    1025            1030            1035

Ser Gly Ser Thr Phe Arg Cys Cys His Gly Glu Asp Cys Ser Gln
    1040            1045            1050

Ile Gly Leu His Ala Ala Ala Pro His Leu Asp Lys Val Asn Gly
    1055            1060            1065

Ile Ser Glu Ile Glu Asn Ser Lys Val Tyr Asp Asp Gly Ala Pro
    1070            1075            1080

Gln Cys Gly Ile Lys Cys Trp Phe Val Lys Ser Gly Glu Trp Ile
    1085            1090            1095

Ser Gly Ile Phe Ser Gly Asn Trp Ile Val Leu Ile Val Leu Cys
    1100            1105            1110

Val Phe Leu Leu Phe Ser Leu Val Leu Leu Ser Ile Leu Cys Pro
    1115            1120            1125

Val Arg Lys His Lys Lys Ser
    1130            1135

<210> SEQ ID NO 3
<211> LENGTH: 3682
<212> TYPE: DNA
<213> ORGANISM: Puumala virus

<400> SEQUENCE: 3

-continued

```
tagtagtaga ctccgcaaga agaagcaaac acagatcaat atgggagaac ttagtccagt    60
ttgtctgtat ctgcttctcc agggtctatt actatgtaat acaggggctg ccagaaacct   120
taatgagctt aaaatggaat gtccacatac tattagatta gggcagggtc ttgttgtggg   180
ttcagtagaa ttgccatctc ttccaataca gcaggtcgag acactaaagc tggagagttc   240
ttgtaatttt gatctacata ccagtacagc aggacaacaa tcattcacaa aatggacatg   300
ggaaattaaa ggtgatcttg cagagaacac acaggcatca tcaacaagtt ttcaaacaaa   360
aagcagtgaa gtgaatttga gaggattatg tttgatccct actttagtgg ttgaaacagc   420
agcaagaatg cgaaaaacaa tagcatgtta tgacctgtca tgcaatcaaa cagtgtgtca   480
gcctactgtc tatttaatgg gacctatcca gacttgtata acaactaaaa gttgtctctt   540
gagtttaggt gatcaaagga ttcaagtaaa ttatgaaaaa acatactgtg tttctgggga   600
ccttgttgaa ggtatctgtt ttaatccaat acatacaatg gcactctctc aacctagtca   660
tacatatgat ataatgacca tgatggttcg ctgtttcttg gtaataaaga aagtgacttc   720
tggtgacagt atgaagattg aaaagaactt tgagactctt gttcaaaaaa atggctgcac   780
agctaataac ttccaagggt attatatctg tcttataggg agtagttcag agcccttata   840
tgttccagca ttagatgatt atcgttcagc tgaagttctt tcaaggatgg catttgcacc   900
acatggtgaa gatcatgata ttgagaaaaa tgcagtgagt gcaatgcgta ttgctggaaa   960
ggtgacagga aaggtgccat caacagaatc atcagataca gtacagggga ttgcattttc  1020
aggtagtcct ctttatacat ctactggtgt cttgacatca aaagatgatc ctgtctacat  1080
ttgggctcct ggaatcataa tggaaggaaa ccattctatt tgtgaaaaga agaccttacc  1140
ccttacatgg actggtttta tttcattgcc tggagagatt gaaaaaacaa cacaatgtac  1200
agtattttgt acattggctg gaccaggtgc agattgtgaa gcttactctg aaacaggcat  1260
cttcaacata agttcaccta cttgcttaat aaatcgtgtc cagagattcc gtggttcaga  1320
acagcaaata aagtttgtgt gccagagagt ggacatggat atcactgttt actgtaatgg  1380
gatgaagaaa gtcattctca ccaagaccct agttattgga caatgcattt atacttttac  1440
tagtattttc tctctaatcc ctggtgttgc acattccctt gctgttgaat tatgtgtacc  1500
tggtcttcat ggttgggcaa ctatgctatt attactaaca ttttgttttg ctgggtctt   1560
aataccaact ataacaatga tcctgctaaa gatattgatt gcattcgcat acttatgttc  1620
taaatataac acagattcga aattcaggat cttgattgag aaagtgaaaa gagagtacca  1680
gaaaacaatg ggttcaatgg tttgtgaagt gtgtcagtat aatgtgagga ctgcaaaaga  1740
actggagtca catagaaaga gttgttccat tggttcatgc ccttattgtc tcaatccatc  1800
tgaggcaaca acatctgccc ttcaggctca tttaaagtg tgtaagctca gatcacggtt  1860
tcaggagaat ttaagaaagt cattaacggt atatgagcct atgcaagggt gctaccggac  1920
tttatccctc tttagatata ggagtcggtt ctttgtgggt ctagtctggt gcgtgttatt  1980
ggttcatcac ttaattgtat gggctgccag tgctgaaaca caaaatttaa atgcaggttg  2040
gacagacaca gcacatggat ctagaattat acctatgaaa actgatctgg aattagactt  2100
ctctcttcag tcatcagcaa gctatacata taggagacag ctacaaaacc cagcaaacga  2160
acaagagaaa atcccatttc atctgcagtt aagcaaacaa gtgattcatg cagagatcca  2220
gcatttaggt cattggatgg atgctacatt taatcttaaa actgcatttc actgctatgg  2280
ctcatgtgag aagtatgctt atccttggca gacagcaggt tgtttcatag aaaaagatta  2340
```

-continued

```
tgaatatgag actggttggg gttgtaatcc acctgattgc ccaggggtag ggacaggctg    2400
tactgcttgt ggggtatacc ttgataaatt aaaatcagtt ggaaaggttt tcaaaattgt    2460
gtccttaaga tacacaagga aagtatgcat tcagttgggc acagaacaaa catgtaagac    2520
tgttgatagt aatgactgtc tcattaccac ttcagttaaa gtgtgcttga tagggaccat    2580
atcaaaattc caaccatctg acactttgct atttctaggt ccactacagc agggtggtct    2640
gatatttaaa caatggtgca ctacaacatg ccagtttggc gatcccgggg acataatgag    2700
cacacctaca ggcatgaagt gcccagaatt aaatggttct tttagaaaga aatgtgcatt    2760
tgcaacaact ccagtttgcc agtttgatgg aaatacaatt tcaggctata agaggatgat    2820
tgccacaaag gattcatttc aatctttcaa tgtgacagaa ccccatattt ctacaagtgc    2880
acttgaatgg attgatcctg acagctcact tagggaccat attaatgtaa ttgtgagtcg    2940
tgatctatcc ttccaagacc taagtgaaac accatgtcaa attgatttag caacagcctc    3000
tatagatgga gcatggggtt caggagttgg ttttaatctg gtttgtactg ttagtttaac    3060
agaatgttct gcatttctga catcaatcaa ggcctgtgat gctgcaatgt gttatgggtc    3120
caccacagcc aatctagttc gagggcaaaa taccattcat atcgtcggta agggtgggca    3180
ttctggttca aaatttatgt gttgtcatga cacaaaatgt tctagcaccg gtctagttgc    3240
agctgcacca cacttagatc gtgtgacacc atacaatcag gctgatagtg acaaaatctt    3300
tgatgatggg gcaccagaat gtggtatgtc atgttggttt aaaaaatcag gtgaatggat    3360
tcttggggtt ttgaacggga attggatggt tgttgctgta ctggtagtat tactgatctt    3420
gtccatactc ttattcacat tatgttgtcc tcgtagacct agttacagga aagaacataa    3480
gccctaagtt ttgcttacta acataattat tgtattctgt ttattgacac aattaccata    3540
tgattaactg tattccccca tcttatatct tatataatat tctttattta atcactatat    3600
agaaaaaaaa ctagcacttt actaattaaa ttaccccata ccgattatgc ctggactttt    3660
gttcttgcgg agtctactac ta                                             3682
```

<210> SEQ ID NO 4
<211> LENGTH: 1148
<212> TYPE: PRT
<213> ORGANISM: Puumala virus

<400> SEQUENCE: 4

```
Met Gly Glu Leu Ser Pro Val Cys Leu Tyr Leu Leu Leu Gln Gly Leu
1               5                   10                  15

Leu Leu Cys Asn Thr Gly Ala Ala Arg Asn Leu Asn Glu Leu Lys Met
            20                  25                  30

Glu Cys Pro His Thr Ile Arg Leu Gly Gln Gly Leu Val Val Gly Ser
        35                  40                  45

Val Glu Leu Pro Ser Leu Pro Ile Gln Gln Val Glu Thr Leu Lys Leu
    50                  55                  60

Glu Ser Ser Cys Asn Phe Asp Leu His Thr Ser Thr Ala Gly Gln Gln
65                  70                  75                  80

Ser Phe Thr Lys Trp Thr Trp Glu Ile Lys Gly Asp Leu Ala Glu Asn
                85                  90                  95

Thr Gln Ala Ser Ser Thr Ser Phe Gln Thr Lys Ser Ser Glu Val Asn
            100                 105                 110

Leu Arg Gly Leu Cys Leu Ile Pro Thr Leu Val Val Glu Thr Ala Ala
        115                 120                 125

Arg Met Arg Lys Thr Ile Ala Cys Tyr Asp Leu Ser Cys Asn Gln Thr
```

```
            130                 135                 140
Val Cys Gln Pro Thr Val Tyr Leu Met Gly Pro Ile Gln Thr Cys Ile
145                 150                 155                 160

Thr Thr Lys Ser Cys Leu Leu Ser Leu Gly Asp Gln Arg Ile Gln Val
                165                 170                 175

Asn Tyr Glu Lys Thr Tyr Cys Val Ser Gly Asp Leu Val Glu Gly Ile
            180                 185                 190

Cys Phe Asn Pro Ile His Thr Met Ala Leu Ser Gln Pro Ser His Thr
        195                 200                 205

Tyr Asp Ile Met Thr Met Met Val Arg Cys Phe Leu Val Ile Lys Lys
    210                 215                 220

Val Thr Ser Gly Asp Ser Met Lys Ile Glu Lys Asn Phe Glu Thr Leu
225                 230                 235                 240

Val Gln Lys Asn Gly Cys Thr Ala Asn Asn Phe Gln Gly Tyr Tyr Ile
                245                 250                 255

Cys Leu Ile Gly Ser Ser Glu Pro Leu Tyr Val Pro Ala Leu Asp
            260                 265                 270

Asp Tyr Arg Ser Ala Glu Val Leu Ser Arg Met Ala Phe Ala Pro His
        275                 280                 285

Gly Glu Asp His Asp Ile Glu Lys Asn Ala Val Ser Ala Met Arg Ile
    290                 295                 300

Ala Gly Lys Val Thr Gly Lys Val Pro Ser Thr Glu Ser Ser Asp Thr
305                 310                 315                 320

Val Gln Gly Ile Ala Phe Ser Gly Ser Pro Leu Tyr Thr Ser Thr Gly
                325                 330                 335

Val Leu Thr Ser Lys Asp Asp Pro Val Tyr Ile Trp Ala Pro Gly Ile
            340                 345                 350

Ile Met Glu Gly Asn His Ser Ile Cys Glu Lys Lys Thr Leu Pro Leu
        355                 360                 365

Thr Trp Thr Gly Phe Ile Ser Leu Pro Gly Glu Ile Glu Lys Thr Thr
    370                 375                 380

Gln Cys Thr Val Phe Cys Thr Leu Ala Gly Pro Gly Ala Asp Cys Glu
385                 390                 395                 400

Ala Tyr Ser Glu Thr Gly Ile Phe Asn Ile Ser Ser Pro Thr Cys Leu
                405                 410                 415

Ile Asn Arg Val Gln Arg Phe Arg Gly Ser Glu Gln Ile Lys Phe
            420                 425                 430

Val Cys Gln Arg Val Asp Met Asp Ile Thr Val Tyr Cys Asn Gly Met
        435                 440                 445

Lys Lys Val Ile Leu Thr Lys Thr Leu Val Ile Gly Gln Cys Ile Tyr
    450                 455                 460

Thr Phe Thr Ser Ile Phe Ser Leu Ile Pro Gly Val Ala His Ser Leu
465                 470                 475                 480

Ala Val Glu Leu Cys Val Pro Gly Leu His Gly Trp Ala Thr Met Leu
                485                 490                 495

Leu Leu Leu Thr Phe Cys Phe Gly Trp Val Leu Ile Pro Thr Ile Thr
            500                 505                 510

Met Ile Leu Leu Lys Ile Leu Ile Ala Phe Ala Tyr Leu Cys Ser Lys
        515                 520                 525

Tyr Asn Thr Asp Ser Lys Phe Arg Ile Leu Ile Glu Lys Val Lys Arg
    530                 535                 540

Glu Tyr Gln Lys Thr Met Gly Ser Met Val Cys Glu Val Cys Gln Tyr
545                 550                 555                 560
```

```
Glu Cys Glu Thr Ala Lys Glu Leu Ser His Arg Lys Ser Cys Ser
                565                 570                 575

Ile Gly Ser Cys Pro Tyr Cys Leu Asn Pro Ser Glu Ala Thr Thr Ser
            580                 585                 590

Ala Leu Gln Ala His Phe Lys Val Cys Lys Leu Arg Ser Arg Phe Gln
        595                 600                 605

Glu Asn Leu Arg Lys Ser Leu Thr Val Tyr Glu Pro Met Gln Gly Cys
    610                 615                 620

Tyr Arg Thr Leu Ser Leu Phe Arg Tyr Arg Ser Arg Phe Phe Val Gly
625                 630                 635                 640

Leu Val Trp Cys Val Leu Leu Val His His Leu Ile Val Trp Ala Ala
            645                 650                 655

Ser Ala Glu Thr Gln Asn Leu Asn Ala Gly Trp Thr Asp Thr Ala His
        660                 665                 670

Gly Ser Arg Ile Ile Pro Met Lys Thr Asp Leu Glu Leu Asp Phe Ser
    675                 680                 685

Leu Gln Ser Ser Ala Ser Tyr Thr Tyr Arg Arg Gln Leu Gln Asn Pro
690                 695                 700

Ala Asn Glu Gln Glu Lys Ile Pro Phe His Leu Gln Leu Ser Lys Gln
705                 710                 715                 720

Val Ile His Ala Glu Ile Gln His Leu Gly His Trp Met Asp Ala Thr
            725                 730                 735

Phe Asn Leu Lys Thr Ala Phe His Cys Tyr Gly Ser Cys Glu Lys Tyr
            740                 745                 750

Ala Tyr Pro Trp Gln Thr Ala Gly Cys Phe Ile Glu Lys Asp Tyr Glu
        755                 760                 765

Tyr Glu Thr Gly Trp Gly Cys Asn Pro Pro Asp Cys Pro Gly Val Gly
    770                 775                 780

Thr Gly Cys Thr Ala Cys Gly Val Tyr Leu Asp Lys Leu Lys Ser Val
785                 790                 795                 800

Gly Lys Val Phe Lys Ile Val Ser Leu Arg Tyr Thr Arg Lys Val Cys
            805                 810                 815

Ile Gln Leu Gly Thr Glu Gln Thr Cys Lys Thr Val Asp Ser Asn Asp
            820                 825                 830

Cys Leu Ile Thr Ser Val Lys Val Cys Leu Ile Gly Thr Ile Ser
        835                 840                 845

Lys Phe Gln Pro Ser Asp Thr Leu Leu Phe Leu Gly Pro Leu Gln Gln
    850                 855                 860

Gly Gly Leu Ile Phe Lys Gln Trp Cys Thr Thr Thr Cys Gln Phe Gly
865                 870                 875                 880

Asp Pro Gly Asp Ile Met Ser Thr Pro Thr Gly Met Lys Cys Pro Glu
            885                 890                 895

Leu Asn Gly Ser Phe Arg Lys Lys Cys Ala Phe Ala Thr Thr Pro Val
            900                 905                 910

Cys Gln Phe Asp Gly Asn Thr Ile Ser Gly Tyr Lys Arg Met Ile Ala
        915                 920                 925

Thr Lys Asp Ser Phe Gln Ser Phe Asn Val Thr Glu Pro His Ile Ser
    930                 935                 940

Thr Ser Ala Leu Glu Trp Ile Asp Pro Asp Ser Ser Leu Arg Asp His
945                 950                 955                 960

Ile Asn Val Ile Val Ser Arg Asp Leu Ser Phe Gln Asp Leu Ser Glu
            965                 970                 975
```

```
Thr Pro Cys Gln Ile Asp Leu Ala Thr Ala Ser Ile Asp Gly Ala Trp
            980                 985                 990
Gly Ser Gly Val Gly Phe Asn Leu Val Cys Thr Val Ser Leu Thr Glu
            995                 1000                1005
Cys Ser Ala Phe Leu Thr Ser Ile Lys Ala Cys Asp Ala Ala Met
        1010                1015                1020
Cys Tyr Gly Ser Thr Thr Ala Asn Leu Val Arg Gly Gln Asn Thr
        1025                1030                1035
Ile His Ile Val Gly Lys Gly Gly His Ser Gly Ser Lys Phe Met
        1040                1045                1050
Cys Cys His Asp Thr Lys Cys Ser Ser Thr Gly Leu Val Ala Ala
        1055                1060                1065
Ala Pro His Leu Asp Arg Val Thr Pro Tyr Asn Gln Ala Asp Ser
        1070                1075                1080
Asp Lys Ile Phe Asp Asp Gly Ala Pro Glu Cys Gly Met Ser Cys
        1085                1090                1095
Trp Phe Lys Lys Ser Gly Glu Trp Ile Leu Gly Val Leu Asn Gly
        1100                1105                1110
Asn Trp Met Val Val Ala Val Leu Val Val Leu Leu Ile Leu Ser
        1115                1120                1125
Ile Leu Leu Phe Thr Leu Cys Cys Pro Arg Arg Pro Ser Tyr Arg
        1130                1135                1140
Lys Glu His Lys Pro
        1145

<210> SEQ ID NO 5
<211> LENGTH: 3651
<212> TYPE: DNA
<213> ORGANISM: Seoul virus

<400> SEQUENCE: 5
tagtagtaga ctccgcaaga aacagcagtt aaataacagc aggatcatgt ggagtttgct      60
attactggcc gctttagttg gccaaggctt tgcattaaaa aatgtgtttg acatgagaat     120
tcagtgcccc cactcagtca aatttgggga aacaagtgtg tcaggctaca cagaactgcc     180
cccactctca ttacaggagg cagaacagct ggtgccagag agctcatgca acatggacaa     240
ccaccaatca ctctcaacaa taaataaatt aaccaaggtc atatggcgga aaaaggcaaa     300
tcaggaatca gcaaaccaga attcatttga acttatggag agtgaagtca gctttaaagg     360
gttgtgtatg ttaaagcata aatggttgaa gaatcctac agaaatagga gatcagtaat      420
ctgttatgat ctagcctgta atagtacatt ctgtaagcca actgtctaca tgattgttcc     480
tatacatgca tgcaacatga tgaaaagctg tttgattggt cttggtcctt acagagtcca     540
ggtcgtttat gaaaggacat actgcactac gggtatattg acagaaggaa aatgctttgt     600
tcctgacaag gctgtcgtca gtgcattgaa gagaggcatg tacgccatag caagcataga     660
gacaatctgc ttttttattc atcagaaagg aatacatat aagatagtga ctgccatcac     720
atcggcaatg ggctccaaat gtaataatac agatactaaa gttcaagggt attatatctg     780
tattattggt gggaactctg cccccgtata tgcccctgct ggtgaagact ttagggcaat     840
ggaggttttt tccgggatta ttacatcacc gcatggagaa gaccatgatc ccctggcga      900 agaaattgca acataccaga tttcagggca gatagaggca aaaatccctc atacagtgag     960
ctccaagaac ttaaaattga ctgcttttgc aggtattcca tcatactcat caaccagtat    1020
attgactgct tcagaagatg gtcgtttcat atttagtcct ggtctatttc ctaacctaaa    1080
```

-continued

```
tcagtcagtc tgtgacaaca atgcactccc tttaatctgg aggggcctaa ttgatttaac    1140
aggatactat gaggcagtcc acccttgcaa tgtattctgt gtcttatcag gaccaggtgc    1200
ttcatgtgaa gccttttcag aaggaggtat tttcaatatt acttccccaa tgtgtcttgt    1260
gtccaagcaa ataggttta gagcagctga gcagcagatc agctttgttt gccaaagggt     1320
tgatatggat attatagtgt actgtaatgg tcagaaaaag acaatcctaa caaaaacatt    1380
agttataggc caatgcattt atactattac aagtctcttt tcactgttac cagggggttgc   1440
ccattctatt gctattgagt tgtgtgttcc aggatttcat ggctgggcca cagctgcact    1500
tttgatcaca ttctgctttg ctgggtatt gattcctgca tgtacattag ctattctttt     1560
agttcttaag tttttgcaa atatcctcca cacaagcaat caagagaacc gattcaaagc     1620
cattctacgg aaaataaagg aggagtttga aaaacaaag ggttccatgg tttgtgagat     1680
ctgtaagtac gagtgtgaaa cattaaagga attgaaggca cataatctat catgtgttca    1740
aggggaatgc ccatattgct ttacccactg tgaaccgaca gaaactgcaa ttcaggcaca    1800
ttacaaagtt tgtcaagcca cccaccgatt cagagaagat ttaaaaaaga ctgtgactcc    1860
tcaaaatatt gggcctggtt gttaccgaac attaaatctt tttaggtata aagtaggtg     1920
ttatattctg acaatgtgga ctcttcttct cattattgaa tccattctct gggcagcaag    1980
tgcagcagaa atccccttg tccctctctg gacagataat gctcatggtg ttgggagtgt     2040
tcctatgcat acagaccttg aattagactt ttctttgcca tctagttcta ggtacacata    2100
taaaagacat ctcacaaacc cagttaatga ccaacagagt gtctcattgc acatagaaat    2160
tgaaagtcaa ggcattggtg ctgatgtcca tcatcttgga cattggtatg atgcaagatt    2220
gaatttaaaa acctcatttc attgttatgg tgcctgcaca aaatatcaat atccatggca    2280
cactgcaaaa tgccattttg agaaagatta tgagtatgaa aatagctggg catgcaaccc    2340
cccagattgc ccaggggttg gtacaggttg tactgcttgt gggttatatc tcgatcaatt    2400
gaagccggta ggaacagcct ttaaaattat aagtgtaaga tacagtagaa aagtgtgcgt    2460
gcagtttggt gaagagtacc tttgtaaaac aattgatatg aacgattgct ttgtgactag    2520
gcatgccaaa atatgtataa ttgggactgt atctaagttt tctcaaggtg cactctact    2580
atttctgggg cccatggaag gaggtggtat aatctttaaa cactggtgca cgtctacctg    2640
tcactttgga gaccctggtg atgtcatggg tccaaaggat aaaccattta tttgccctga    2700
attcccaggg caattcagga aaaaatgtaa ctttgccaca actccagttt gtgaatatga    2760
tgggaatatt atctcaggct ataagaaagt tcttgcaaca attgattctt ccaatcatt    2820
taacacaagc aatatacact tcactgatga gagaattgaa tggagagacc ctgatggtat    2880
gcttcgggat catattaata tcgttatttc taaagatatt gattttgaaa atttggctga    2940
gaatccttgt aaagtagggc tccaggcagc aaacatagaa ggtgcctggg ttcaggtgt    3000
cgggtttaca ctcacatgcc aggtgtctct cacagaatgc ccaacatttc tcacgtcaat    3060
aagggcctgt gacatggcaa tttgttatgg tgcagaaagt gtgacactct cacgaggaca    3120
aaatactgtc aaaattaccg ggaaaggtgg ccatagtggt tcctcattta agtgctgtca    3180
tgggaaagaa tgttcattaa ctggcctcca agccagtgca ccacatttag ataaggtaaa    3240
tggaatctct gagttagaaa atgagaaagt ttatgatgat ggtgcacctg aatgtggcat    3300
tacttgttgg tttaaaaaat caggtgaatg ggtatgggg ataatcaatg gaactgggg     3360
tgtcctaatt gtcttgtgtg tcctgctgct ctttctctt atcctgttga gcatcctgtg     3420
```

-continued

```
tcctgttaga aagcataaaa aatcataaat cctgcttatt aatcttcata gcatgtatcg    3480
agttttaaac actttaccat taaaaactta acctggctct aatatctgat aactaacttt    3540
cattttattt ttatatggga ttaattacta aaaaaaatac tctcttctat ctcccaatct    3600
tttattgatt caccggggtg ttgtcttgac atcttgcgga gtctactact a             3651
```

<210> SEQ ID NO 6
<211> LENGTH: 1133
<212> TYPE: PRT
<213> ORGANISM: Seoul virus

<400> SEQUENCE: 6

```
Met Trp Ser Leu Leu Leu Ala Ala Leu Val Gly Gln Gly Phe Ala
 1               5                  10                  15

Leu Lys Asn Val Phe Asp Met Arg Ile Gln Cys Pro His Ser Val Lys
                20                  25                  30

Phe Gly Glu Thr Ser Val Ser Gly Tyr Thr Glu Leu Pro Pro Leu Ser
            35                  40                  45

Leu Gln Glu Ala Glu Gln Leu Val Pro Glu Ser Ser Cys Asn Met Asp
        50                  55                  60

Asn His Gln Ser Leu Ser Thr Ile Asn Lys Leu Thr Lys Val Ile Trp
65                  70                  75                  80

Arg Lys Lys Ala Asn Gln Glu Ser Ala Asn Gln Asn Ser Phe Glu Leu
                85                  90                  95

Met Glu Ser Glu Val Ser Phe Lys Gly Leu Cys Met Leu Lys His Arg
            100                 105                 110

Met Val Glu Glu Ser Tyr Arg Asn Arg Arg Ser Val Ile Cys Tyr Asp
        115                 120                 125

Leu Ala Cys Asn Ser Thr Phe Cys Lys Pro Thr Val Tyr Met Ile Val
    130                 135                 140

Pro Ile His Ala Cys Asn Met Met Lys Ser Cys Leu Ile Gly Leu Gly
145                 150                 155                 160

Pro Tyr Arg Val Gln Val Val Tyr Glu Arg Thr Tyr Cys Thr Thr Gly
                165                 170                 175

Ile Leu Thr Glu Gly Lys Cys Phe Val Pro Asp Lys Ala Val Val Ser
            180                 185                 190

Ala Leu Lys Arg Gly Met Tyr Ala Ile Ala Ser Ile Glu Thr Ile Cys
        195                 200                 205

Phe Phe Ile His Gln Lys Gly Asn Thr Tyr Lys Ile Val Thr Ala Ile
    210                 215                 220

Thr Ser Ala Met Gly Ser Lys Cys Asn Asn Thr Asp Thr Lys Val Gln
225                 230                 235                 240

Gly Tyr Tyr Ile Cys Ile Ile Gly Gly Asn Ser Ala Pro Val Tyr Ala
                245                 250                 255

Pro Ala Gly Glu Asp Phe Arg Ala Met Glu Val Phe Ser Gly Ile Ile
            260                 265                 270

Thr Ser Pro His Gly Glu Asp His Asp Leu Pro Gly Glu Glu Ile Ala
        275                 280                 285

Thr Tyr Gln Ile Ser Gly Gln Ile Glu Ala Lys Ile Pro His Thr Val
    290                 295                 300

Ser Ser Lys Asn Leu Lys Leu Thr Ala Phe Ala Gly Ile Pro Ser Tyr
305                 310                 315                 320

Ser Ser Thr Ser Ile Leu Thr Ala Ser Glu Asp Gly Arg Phe Ile Phe
                325                 330                 335
```

```
Ser Pro Gly Leu Phe Pro Asn Leu Asn Gln Ser Val Cys Asp Asn Asn
            340                 345                 350

Ala Leu Pro Leu Ile Trp Arg Gly Leu Ile Asp Leu Thr Gly Tyr Tyr
        355                 360                 365

Glu Ala Val His Pro Cys Asn Val Phe Cys Val Leu Ser Gly Pro Gly
    370                 375                 380

Ala Ser Cys Glu Ala Phe Ser Glu Gly Gly Ile Phe Asn Ile Thr Ser
385                 390                 395                 400

Pro Met Cys Leu Val Ser Lys Gln Asn Arg Phe Arg Ala Ala Glu Gln
                405                 410                 415

Gln Ile Ser Phe Val Cys Gln Arg Val Asp Met Asp Ile Ile Val Tyr
            420                 425                 430

Cys Asn Gly Gln Lys Lys Thr Ile Leu Thr Lys Thr Leu Val Ile Gly
        435                 440                 445

Gln Cys Ile Tyr Thr Ile Thr Ser Leu Phe Ser Leu Leu Pro Gly Val
    450                 455                 460

Ala His Ser Ile Ala Ile Glu Leu Cys Val Pro Gly Phe His Gly Trp
465                 470                 475                 480

Ala Thr Ala Ala Leu Leu Ile Thr Phe Cys Phe Gly Trp Val Leu Ile
                485                 490                 495

Pro Ala Cys Thr Leu Ala Ile Leu Leu Val Leu Lys Phe Phe Ala Asn
            500                 505                 510

Ile Leu His Thr Ser Asn Gln Glu Asn Arg Phe Lys Ala Ile Leu Arg
        515                 520                 525

Lys Ile Lys Glu Glu Phe Glu Lys Thr Lys Gly Ser Met Val Cys Glu
    530                 535                 540

Ile Cys Lys Tyr Glu Cys Glu Thr Leu Lys Glu Leu Lys Ala His Asn
545                 550                 555                 560

Leu Ser Cys Val Gln Gly Glu Cys Pro Tyr Cys Phe Thr His Cys Glu
                565                 570                 575

Pro Thr Glu Thr Ala Ile Gln Ala His Tyr Lys Val Cys Gln Ala Thr
            580                 585                 590

His Arg Phe Arg Glu Asp Leu Lys Lys Thr Val Thr Pro Gln Asn Ile
        595                 600                 605

Gly Pro Gly Cys Tyr Arg Thr Leu Asn Leu Phe Arg Tyr Lys Ser Arg
    610                 615                 620

Cys Tyr Ile Leu Thr Met Trp Thr Leu Leu Ile Ile Glu Ser Ile
625                 630                 635                 640

Leu Trp Ala Ala Ser Ala Ala Glu Ile Pro Leu Val Pro Leu Trp Thr
                645                 650                 655

Asp Asn Ala His Gly Val Gly Ser Val Pro Met His Thr Asp Leu Glu
            660                 665                 670

Leu Asp Phe Ser Leu Pro Ser Ser Arg Tyr Thr Tyr Lys Arg His
        675                 680                 685

Leu Thr Asn Pro Val Asn Asp Gln Gln Ser Val Ser Leu His Ile Glu
    690                 695                 700

Ile Glu Ser Gln Gly Ile Gly Ala Asp Val His His Leu Gly His Trp
705                 710                 715                 720

Tyr Asp Ala Arg Leu Asn Leu Lys Thr Ser Phe His Cys Tyr Gly Ala
                725                 730                 735

Cys Thr Lys Tyr Gln Tyr Pro Trp His Thr Ala Lys Cys His Phe Glu
            740                 745                 750

Lys Asp Tyr Glu Tyr Glu Asn Ser Trp Ala Cys Asn Pro Pro Asp Cys
```

```
                755             760             765
Pro Gly Val Gly Thr Gly Cys Thr Ala Cys Gly Leu Tyr Leu Asp Gln
770                 775                 780

Leu Lys Pro Val Gly Thr Ala Phe Lys Ile Ile Ser Val Arg Tyr Ser
785                 790                 795                 800

Arg Lys Val Cys Val Gln Phe Gly Glu Glu Tyr Leu Cys Lys Thr Ile
                805                 810                 815

Asp Met Asn Asp Cys Phe Val Thr Arg His Ala Lys Ile Cys Ile Ile
            820                 825                 830

Gly Thr Val Ser Lys Phe Ser Gln Gly Asp Thr Leu Leu Phe Leu Gly
        835                 840                 845

Pro Met Glu Gly Gly Gly Ile Ile Phe Lys His Trp Cys Thr Ser Thr
850                 855                 860

Cys His Phe Gly Asp Pro Gly Asp Val Met Gly Pro Lys Asp Lys Pro
865                 870                 875                 880

Phe Ile Cys Pro Glu Phe Pro Gly Gln Phe Arg Lys Lys Cys Asn Phe
                885                 890                 895

Ala Thr Thr Pro Val Cys Glu Tyr Asp Gly Asn Ile Ile Ser Gly Tyr
            900                 905                 910

Lys Lys Val Leu Ala Thr Ile Asp Ser Phe Gln Ser Phe Asn Thr Ser
        915                 920                 925

Asn Ile His Phe Thr Asp Glu Arg Ile Glu Trp Arg Asp Pro Asp Gly
930                 935                 940

Met Leu Arg Asp His Ile Asn Ile Val Ile Ser Lys Asp Ile Asp Phe
945                 950                 955                 960

Glu Asn Leu Ala Glu Asn Pro Cys Lys Val Gly Leu Gln Ala Ala Asn
                965                 970                 975

Ile Glu Gly Ala Trp Gly Ser Gly Val Gly Phe Thr Leu Thr Cys Gln
            980                 985                 990

Val Ser Leu Thr Glu Cys Pro Thr  Phe Leu Thr Ser Ile Arg Ala Cys
        995                 1000                1005

Asp Met Ala Ile Cys Tyr Gly  Ala Glu Ser Val Thr  Leu Ser Arg
    1010                1015                1020

Gly Gln Asn Thr Val Lys Ile  Thr Gly Lys Gly  His Ser Gly
    1025                1030                1035

Ser Ser Phe Lys Cys Cys His  Gly Lys Glu Cys Ser  Leu Thr Gly
    1040                1045                1050

Leu Gln Ala Ser Ala Pro His  Leu Asp Lys Val Asn  Gly Ile Ser
    1055                1060                1065

Glu Leu Glu Asn Glu Lys Val  Tyr Asp Asp Gly Ala  Pro Glu Cys
    1070                1075                1080

Gly Ile  Thr Cys Trp Phe Lys  Ser Gly Glu Trp  Val Met Gly
    1085                1090                1095

Ile Ile  Asn Gly Asn Trp Val  Val Leu Ile Val Leu  Cys Val Leu
    1100                1105                1110

Leu Leu  Phe Ser Leu Ile Leu  Leu Ser Ile Leu Cys  Pro Val Arg
    1115                1120                1125

Lys His  Lys Lys Ser
    1130

<210> SEQ ID NO 7
<211> LENGTH: 3644
<212> TYPE: DNA
<213> ORGANISM: Dobrava virus
```

<400> SEQUENCE: 7

```
tagtagtaga ctccgcaaga acagcagtt aaataacagc atgatcatgt ggggtctact      60
attgacaatg attttgatcg attttggggc atccttaagg aatgtttatg acatgaagat    120
agaatgccca cattcaatca actttgggga gagcagtgta acaggtaagg tggaattacc    180
accccttctg ctcacagatg cagaggcctt ggtcccggag agttcttgta acatggacaa    240
ccatcagtct atgtcaatta tacaaaaagt gacaaaagtg agttggagaa aaaaggcaga    300
caaagcccaa gctgccaagg actcatttga gacaacatca agcgaggtta atctgaaggg    360
gacatgcaca ttgagtcata ggatggttga agaatcctac aggaatagga gatcagtgat    420
atgctatgac ttgtcttgca attcaacaca ttgtaagcca acgatgcata tgattgtgcc    480
tgtgcactca tgcaacatga tgaaaagctg tctggttggg cttgggcctt atcgaatcca    540
agttgtctat gaaagaacct actgtacaac tggtatacta acagaaggga agtgttttgt    600
gccagaccag agtattgtca gtgtcatcaa gaatggggtt tttgacattg caagtgtgag    660
cattgtctgt ttttttatca gagttaaagg aactaactac aagataatgg cgagtattaa    720
aacagcaact gcaaataact gtaatgacac tgacaataag gttcaaggat attaccttg    780
tattgttggg ggaaattctt ctcctgtgta tgcaccttca accactgatt ttagatctat    840
ggaagcactt gctagccttt taagagctcc tcatggtgag gaccatgatt tatctggaga    900
agaggttgca acttattcaa ttgccgggca aattgaaggc aaaatcccac atactgcaaa    960
tgcagcaaac atgctatttta ctgcattctc aggaattcct agttactctt cattgagtgt   1020
ttttattgga agtcaagatg ggcctattat ttatagccca ggattgtttc ccaagttgaa   1080
ccaatcttca tgtgataagg tcgcactacc attgatatgg aagggtaca tagatctacc    1140
tggctattat gaaacagttc acccgtgtaa tgtcttttgt gtgctatctg gcccaggagc   1200
atcatgtgag gcattctcag aaggtggtat tttcaatatt acatccccta catgccttgt   1260
gtcaaagcaa aatcggttca gggcagctga gcagcaagtc aatttcgtat gccagcgagt   1320
cgaccaagac attattatct actgtaatgg acaaaagaag acaatttga ccaagacatt    1380
agtgattggg cagtgtattt attcagtgac tagtttgttt tcaataatgc ctggggtagc   1440
acattcaatt gcaatcgaat tatgtgtacc agggttccat ggctgggcaa ctgctgctct   1500
tctcaccaca ttctgctttg ctggatact gatcccttcc atcacattgg ctgtattggt    1560
tgtcttaaag tttttttgcag caatcttaca taatagctct caagaaaacc gttttaaaat   1620
tatcctaagg aagattaaag aagaattga aaagactaag ggctcaatgg tttgtgaagt    1680
gtgcaagtat gagtgtgaaa cagggaagga gcttaaagcc cataaattgt cttgccctca   1740
gtcacagtgt ccttattgct ttacacattg tgagcctaca gaatctgcct tccaggcaca   1800
ttataaagtg tgccaggcaa cacacaggtt tagagatgat tgaagaaaa caataacacc    1860
tcaatctaca agcccggtt gttaccggac attaaatctc tttaggtata aagtaggtg     1920
ttacatttt acagtgtggg tcaccctgct aatcattgaa tcaatcatgt gggcagctag   1980
cgcatcagaa aatgttttgg agccaagctg gaatgacaac gcacatggtg ttggtgttgt    2040
cccaatgcat actgatctgg aactagattt ttctcttccg tcaagttcta agtacacata   2100
taaagaaaaa ctgacaagtc cattaaatca agaacaatca gtagatcttc acatagagat   2160
agagagtcaa gggatttcta caagtgttca tgcattaggt cattggtttg atgggagact   2220
taatttaaag acatcttttc attgttatgg tgcatgtact aagtatgaat atccttggca   2280
```

```
tacagcaaaa tgccactttg aaagggattt cgagtatgag aacagctggg gctgtaatcc    2340
tgctgattgc cctgggattg gtacgggctg tactgcatgc ggactataca ttgaccaact    2400
taaacctgta ggcagtgcat acaagctaat cacagtccgt tacagccgta agtatgtgt    2460 tcagtttggt gaagaaaacc tatgtaagac aattgacatg aatgattgct ttgttacaag    2520
acatgtcaaa gtatgcatta taggtacagt ttcaaagttc tcacaaggtg atacctagt    2580 attcctgggc cctatggaag gtgggggctt aatatttaag gattggtgca ctagcacatg    2640
ccaatttggt gatcctgggg acattatgag tcctaaagac aaagggttta gctgccctga    2700
cttcacaggc cacttccgga aaaatgcaa ctttgcaaca cacctgtat gcgagtatga    2760 tggtaatatg gtctctaggt ataagaaagt aatggcaact attgattcct ttcagtcatt    2820
taacactagc tcaattcatt acacagatga aaggattgaa cggaaggacc ctgatgggat    2880
gcttaaggac catctcaata tacttgtcac aaaagacatt gactttgaaa accttgggga    2940
gaacccgtgc aaagtagggc ttcaaacatc atcaatagaa ggtgcatggg gctctggggt    3000
tggtttcacc cttacttgtc aaatctcact gacagaatgt tctcgctttc tgacatccat    3060
taaagcatgt gacatggcaa tctgttatgg tgcacaaagt gtcacactca ttagaggcca    3120
aaatacagtg aaggtttccg ggaagggtgg gcatagtggc tcttcattca agtgttgtca    3180
agggacagat tgctctcagc agggggctaca agcaagcgca ccacacctag acaaagtcaa    3240
tggaattgtt gaacaagata gtgaaaaagt ctatgatgat ggtgcaccac aatgtggcat    3300
ttcatgctgg tttgttaagt ctggggagtg gataacagga atctttaatg gaaactggat    3360
tgtcattgtt gtgcttgttt tcttcatact atccttaatc ttacttagtc ttttatgccc    3420
cattcgtaag cataagcgct cataagtaaa tactagagaa acctattagc atgtccctat    3480
atatagcctt taacaatgca atttttatata tcagttttaaa cttctgtact tattaatttt    3540 ttacattttat taacctagtt atctaaaaaa aataactcct tcattactat aaatcttagt    3600
ccttagtatg tgggtatttc tatatcttgc ggagtctact acta              3644
```

```
<210> SEQ ID NO 8
<211> LENGTH: 1134
<212> TYPE: PRT
<213> ORGANISM: Dobrava virus

<400> SEQUENCE: 8

Met Ile Met Trp Gly Leu Leu Leu Thr Met Ile Leu Ile Asp Phe Gly
1               5                   10                  15

Ala Ser Leu Arg Asn Val Tyr Asp Met Lys Ile Glu Cys Pro His Ser
                20                  25                  30

Ile Asn Phe Gly Glu Ser Ser Val Thr Gly Lys Val Glu Leu Pro Pro
            35                  40                  45

Leu Leu Leu Thr Asp Ala Glu Ala Leu Val Pro Glu Ser Ser Cys Asn
        50                  55                  60

Met Asp Asn His Gln Ser Met Ser Ile Ile Gln Lys Val Thr Lys Val
65                  70                  75                  80

Ser Trp Arg Lys Lys Ala Asp Lys Ala Gln Ala Ala Lys Asp Ser Phe
                85                  90                  95

Glu Thr Thr Ser Ser Glu Val Asn Leu Lys Gly Thr Cys Thr Leu Ser
                100                 105                 110

His Arg Met Val Glu Glu Ser Tyr Arg Asn Arg Arg Ser Val Ile Cys
            115                 120                 125

Tyr Asp Leu Ser Cys Asn Ser Thr His Cys Lys Pro Thr Met His Met
```

```
            130                 135                 140
Ile Val Pro Val His Ser Cys Asn Met Met Lys Ser Cys Leu Val Gly
145                 150                 155                 160

Leu Gly Pro Tyr Arg Ile Gln Val Val Tyr Glu Arg Thr Tyr Cys Thr
                165                 170                 175

Thr Gly Ile Leu Thr Glu Gly Lys Cys Phe Val Pro Asp Gln Ser Ile
            180                 185                 190

Val Ser Val Ile Lys Asn Gly Val Phe Asp Ile Ala Ser Val Ser Ile
        195                 200                 205

Val Cys Phe Phe Ile Arg Val Lys Gly Thr Asn Tyr Lys Ile Met Ala
    210                 215                 220

Ser Ile Lys Thr Ala Thr Ala Asn Asn Cys Asn Asp Thr Asp Asn Lys
225                 230                 235                 240

Val Gln Gly Tyr Tyr Leu Cys Ile Val Gly Asn Ser Ser Pro Val
                245                 250                 255

Tyr Ala Pro Ser Thr Thr Asp Phe Arg Ser Met Glu Ala Leu Ala Ser
            260                 265                 270

Leu Leu Arg Ala Pro His Gly Glu Asp His Asp Leu Ser Gly Glu Glu
        275                 280                 285

Val Ala Thr Tyr Ser Ile Ala Gly Gln Ile Glu Gly Lys Ile Pro His
    290                 295                 300

Thr Ala Asn Ala Ala Asn Met Leu Phe Thr Ala Phe Ser Gly Ile Pro
305                 310                 315                 320

Ser Tyr Ser Ser Leu Ser Val Phe Ile Gly Ser Gln Asp Gly Pro Ile
                325                 330                 335

Ile Tyr Ser Pro Gly Leu Phe Pro Lys Leu Asn Gln Ser Ser Cys Asp
            340                 345                 350

Lys Val Ala Leu Pro Leu Ile Trp Glu Gly Tyr Ile Asp Leu Pro Gly
        355                 360                 365

Tyr Tyr Glu Thr Val His Pro Cys Asn Val Phe Cys Val Leu Ser Gly
    370                 375                 380

Pro Gly Ala Ser Cys Glu Ala Phe Ser Glu Gly Gly Ile Phe Asn Ile
385                 390                 395                 400

Thr Ser Pro Thr Cys Leu Val Ser Lys Gln Asn Arg Phe Arg Ala Ala
                405                 410                 415

Glu Gln Gln Val Asn Phe Val Cys Gln Arg Val Asp Gln Asp Ile Ile
            420                 425                 430

Ile Tyr Cys Asn Gly Gln Lys Lys Thr Ile Leu Thr Lys Thr Leu Val
        435                 440                 445

Ile Gly Gln Cys Ile Tyr Ser Val Thr Ser Leu Phe Ser Ile Met Pro
    450                 455                 460

Gly Val Ala His Ser Ile Ala Ile Glu Leu Cys Val Pro Gly Phe His
465                 470                 475                 480

Gly Trp Ala Thr Ala Ala Leu Leu Thr Thr Phe Cys Phe Gly Trp Ile
                485                 490                 495

Leu Ile Pro Ser Ile Thr Leu Ala Val Leu Val Leu Lys Phe Phe
            500                 505                 510

Ala Ala Ile Leu His Asn Ser Ser Gln Glu Asn Arg Phe Lys Ile Ile
        515                 520                 525

Leu Arg Lys Ile Lys Glu Glu Phe Glu Lys Thr Lys Gly Ser Met Val
    530                 535                 540

Cys Glu Val Cys Lys Tyr Glu Cys Glu Thr Gly Lys Glu Leu Lys Ala
545                 550                 555                 560
```

```
His Asn Leu Ser Cys Pro Gln Ser Gln Cys Pro Tyr Cys Phe Thr His
                565                 570                 575
Cys Glu Pro Thr Glu Ser Ala Phe Gln Ala His Tyr Lys Val Cys Gln
            580                 585                 590
Ala Thr His Arg Phe Arg Asp Asp Leu Lys Lys Thr Ile Thr Pro Gln
        595                 600                 605
Ser Thr Ser Pro Gly Cys Tyr Arg Thr Leu Asn Leu Phe Arg Tyr Lys
    610                 615                 620
Ser Arg Cys Tyr Ile Phe Thr Val Trp Val Thr Leu Leu Ile Ile Glu
625                 630                 635                 640
Ser Ile Met Trp Ala Ala Ser Ala Ser Glu Asn Val Leu Glu Pro Ser
                645                 650                 655
Trp Asn Asp Asn Ala His Gly Val Gly Val Val Pro Met His Thr Asp
            660                 665                 670
Leu Glu Leu Asp Phe Ser Leu Pro Ser Ser Lys Tyr Thr Tyr Lys
        675                 680                 685
Arg Lys Leu Thr Ser Pro Leu Asn Gln Glu Gln Ser Val Asp Leu His
    690                 695                 700
Ile Glu Ile Glu Ser Gln Gly Ile Ser Thr Ser Val His Ala Leu Gly
705                 710                 715                 720
His Trp Phe Asp Gly Arg Leu Asn Leu Lys Thr Ser Phe His Cys Tyr
                725                 730                 735
Gly Ala Cys Thr Lys Tyr Glu Tyr Pro Trp His Thr Ala Lys Cys His
            740                 745                 750
Phe Glu Arg Asp Phe Glu Tyr Glu Asn Ser Trp Gly Cys Asn Pro Ala
        755                 760                 765
Asp Cys Pro Gly Ile Gly Thr Gly Cys Thr Ala Cys Gly Leu Tyr Ile
    770                 775                 780
Asp Gln Leu Lys Pro Val Gly Ser Ala Tyr Lys Leu Ile Thr Val Arg
785                 790                 795                 800
Tyr Ser Arg Lys Val Cys Val Gln Phe Gly Glu Glu Asn Leu Cys Lys
                805                 810                 815
Thr Ile Asp Met Asn Asp Cys Phe Val Thr Arg His Val Lys Val Cys
            820                 825                 830
Ile Ile Gly Thr Val Ser Lys Phe Ser Gln Gly Asp Thr Leu Val Phe
        835                 840                 845
Leu Gly Pro Met Glu Gly Gly Leu Ile Phe Lys Asp Trp Cys Thr
    850                 855                 860
Ser Thr Cys Gln Phe Gly Asp Pro Gly Asp Ile Met Ser Pro Lys Asp
865                 870                 875                 880
Lys Gly Phe Ser Cys Pro Asp Phe Thr Gly His Phe Arg Lys Lys Cys
                885                 890                 895
Asn Phe Ala Thr Thr Pro Val Cys Glu Tyr Asp Gly Asn Met Val Ser
            900                 905                 910
Arg Tyr Lys Lys Val Met Ala Thr Ile Asp Ser Phe Gln Ser Phe Asn
        915                 920                 925
Thr Ser Ser Ile His Tyr Thr Asp Glu Arg Ile Glu Arg Lys Asp Pro
    930                 935                 940
Asp Gly Met Leu Lys Asp His Leu Asn Ile Leu Val Thr Lys Asp Ile
945                 950                 955                 960
Asp Phe Glu Asn Leu Gly Glu Asn Pro Cys Lys Val Gly Leu Gln Thr
                965                 970                 975
```

Ser Ser Ile Glu Gly Ala Trp Gly Ser Gly Val Gly Phe Thr Leu Thr
        980                 985                 990

Cys Gln Ile Ser Leu Thr Glu Cys Ser Arg Phe Leu Thr Ser Ile Lys
        995                 1000                1005

Ala Cys Asp Met Ala Ile Cys Tyr Gly Ala Gln Ser Val Thr Leu
        1010            1015                1020

Ile Arg Gly Gln Asn Thr Val Lys Val Ser Gly Lys Gly Gly His
        1025            1030                1035

Ser Gly Ser Ser Phe Lys Cys Cys Gln Gly Thr Asp Cys Ser Gln
        1040            1045                1050

Gln Gly Leu Gln Ala Ser Ala Pro His Leu Asp Lys Val Asn Gly
        1055            1060                1065

Ile Val Glu Gln Asp Ser Glu Lys Val Tyr Asp Asp Gly Ala Pro
        1070            1075                1080

Gln Cys Gly Ile Ser Cys Trp Phe Val Lys Ser Gly Glu Trp Ile
        1085            1090                1095

Thr Gly Ile Phe Asn Gly Asn Trp Ile Val Ile Val Val Leu Val
        1100            1105                1110

Phe Phe Ile Leu Ser Leu Ile Leu Leu Ser Leu Leu Cys Pro Ile
        1115            1120                1125

Arg Lys His Lys Arg Ser
        1130

<210> SEQ ID NO 9
<211> LENGTH: 3696
<212> TYPE: DNA
<213> ORGANISM: Sin Nombre hantavirus

<400> SEQUENCE: 9
tagtagtaga ctccgcacga agaagcaaac actgaataaa ggagatacag aatggtaggg      60
tgggtttgca tcttcctcgt ggtccttact actgcaactg ctgggctaac acggaatctt     120
tatgagttga agatagaatg tccacatact gtgggtttag gtcagggtta cgtgacaggt     180
tcagtggaaa ttcacaccta ttctcttaac gcaggtagctg atctgaagat tgagagttct     240
tgtaatttcg atttgcatgt cccggctacc actacccaaa atacaatca ggttgactgg     300
accaaaaaaa gttcaactac agaaagcaca atgcaggtg caactacatt tgaggctaaa     360
acaaaagaga taatttgaa aggcacatgt aatattcctc caactacatt tgaagctgca     420
tataaatcaa ggaagacagt aatttgttat gatttagcct gtaatcaaac acattgtctt     480
cctacggtcc atttgattgc tcctgttcaa acgtgcatgt ctgtgcggag ctgtatgata     540
ggtttgctgt caagcaggat tcaagtgata tatgagaaga catactgcgt tacaggtcaa     600
ttaatagagg ggctatgttt catcccaaca catacaattg cactcacaca acctggtcat     660
acctatgata ctatgacatt gccagtgact tgtttttag tagctaaaaa gttgggaaca     720
cagcttaagc tggctgttga gttagagaaa ctgattactg gtgtaagttg cacagaaaac     780
agctttcaag ttactacat ctgtttttatc gggaaacatt cagagccctt atttgtgcca     840
acaatggagg attataggtc agctgagtta tttacccgta tggttttaaa tccgagaggt     900
gaagatcatg accctgatca aaatggacaa ggtttaatga aatagctgg gcctgttaca     960
gctaaggtgc catctacaga aacaactgaa acaatgcaag gaattgcatt tgctggagca    1020
ccaatgtata gctctttctc aaccctcgtg aggaaggctg atcctgagta tgtcttctca    1080
ccaggtataa ttgcagaatc aaatcatagt gtttgtgata aaaaaacagt acccccttaca   1140

```
tggacagggt ttttggcagt ttctggagag atagagaaaa taacaggctg tacagtcttc    1200
tgtacattgg ctggacctgg tgctagttgt gaagcatact cagaaacagg aatctttaat    1260
ataagttctc ctacttgtct agtgaataaa gttcaaaaat tcagaggctc agaacagagg    1320
attaacttca tgtgccaaag agttgatcaa gatgtagttg tctattgtaa tggacaaaag    1380
aaagtcattc ttaccaaaac tctggtcata ggccaatgca tttatacatt cactagttta    1440
ttctcactaa tcccaggagt tgcccattct cttgctgtag agctatgtgt tccaggcctt    1500
catggctggg ctacaacggc attactgatt acttttttgct ttggctggct ccttataccg    1560
gcagtcacct taattatact gaagatcctg aggttgctca ctttctcatg ctcacattat    1620
tccacagaat caaaattcaa agttatctta gaagggttaa aggttgaata tcagaaaaca    1680
atgggctcta tggtgtgtga tatttgccac cacgaatgcg aaacagcaaa agaacttgaa    1740
acacataaga aaagctgtcc agaaggtcaa tgcccgtatt gtatgacaat aactgaatcc    1800
actgagagtg ctctccaagc ccattttgca atctgtaagc taacaaacag gtttcaggaa    1860
aacttaaaaa agtcattgaa acgcccagaa gtacggaaag gttgttacag gacactggga    1920
gtttttagat acaagagcag atgttatgtt ggtttagtat ggggaattct tttaacaact    1980
gaactgatca tatgggcagc cagtgcagac acccctttaa tggagtctgg ttggtctgac    2040
acagcacatg gtgtgggcat aattcctatg aagacagatt tggagcttga ttttgcattg    2100
gcctcatcat cttcttacag ttataggcga aagcttgtta atcctgctaa tcaagaagaa    2160 acactcccctt ttcatttcca gttagataaa caagtagtgc atgcagagat ccagaaccta    2220
ggacattgga tggatggcac attcaacata aaaactgctt ttcactgtta tggggagtgt    2280
aaaaaatatg cctatccttg gcaaacagcc aagtgtttct ttgaaaagga ttatcaatat    2340
gaaacaagtt ggggctgtaa tccaccagac tgtccagggg taggtacagg ttgtacagct    2400
tgtggggtgt accttgataa gctccgttcg gttgggaaag cgtacaagat agtatcactc    2460
aaatatacac ggaaggtgtg tattcaatta ggaacagaac aaacttgtaa acatatagat    2520
gtaaatgatt gcctggttac cccttctgtc aaagtttgta tgattggtac tatatcaaag    2580
ctccagccag gtgataccttt ttgttcttta ggtcctttag agcagggtgg gatcattctt    2640
aagcaatggt gtacaacatc atgtgtgttt ggagatcccg gtgatattat gtcaacaaca    2700
agtgggatgc ggtgcccaga acatactgga tcttttagaa agatctgtgg gtttgctacg    2760
acaccaacat gtgagtatca aggcaacaca gtgtctggat ccaacgcat gatggcaact    2820 cgagattctt tccagtcatt caatgtgaca gaaccacata tcactagcaa ccgacttgag    2880
tggattgatc cagatagcag tatcaaagat cacattaata tggttttaaa tcgagatgtt    2940
tcctttcagg atctaagtga taacccatgc aaggttgacc tgcatacaca atcaattgac    3000
ggggcctggg gttcaggagt aggttttacg ttggtatgta ctgtggggct tacagagtgt    3060 gcaaattta taacttcaat taaagcatgt gattctgcca tgtgttatgg agccacagtg    3120
acaaatctgc ttagagggtc taacacagtt aaagttgttg gtaaaggtgg gcattctgga    3180
tctttgttta aatgctgcca tgatactgac tgtaccgaag aagggttagc agcatctcca    3240
ccacatttag acagggttac aggctataat caaatagatt ctgataaagt ttatgatgac    3300
ggtgcaccgc cctgtacaat caagtgctgg ttcaccaagt caggtgaatg ctgttgggca    3360
atccttaatg gcaattgggt ggtagttgct gttctgattg taattttgat attatcgata    3420
ctccttttta gctttttttg tcctgtcaga agtagaaaga ataaagctaa ttagtgaata    3480
tatatgtgag caagagtatg acaacattat ttcattatat gtatgttctt atatcaataa    3540
```

-continued

```
catttgtata ttcccataac cgaaatattt atactaattt ttattttat acaagtatta       3600 actaacccat taacagctaa aaaaaacaaa tccttaacac ctatataatc ccatttgctt       3660
attacgaggc ttttgttcct gcggagcata ctacta                                3696
```

<210> SEQ ID NO 10
<211> LENGTH: 1140
<212> TYPE: PRT
<213> ORGANISM: Sin Nombre hantavirus

<400> SEQUENCE: 10

```
Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Ile Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Ile Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
```

-continued

```
                340                 345                 350
Ser Val Cys Asp Lys Lys Thr Val Pro Leu Thr Trp Thr Gly Phe Leu
            355                 360                 365
Ala Val Ser Gly Glu Ile Glu Lys Ile Thr Gly Cys Thr Val Phe Cys
        370                 375                 380
Thr Leu Ala Gly Pro Gly Ala Ser Cys Glu Ala Tyr Ser Glu Thr Gly
385                 390                 395                 400
Ile Phe Asn Ile Ser Ser Pro Thr Cys Leu Val Asn Lys Val Gln Lys
                405                 410                 415
Phe Arg Gly Ser Glu Gln Arg Ile Asn Phe Met Cys Gln Arg Val Asp
            420                 425                 430
Gln Asp Val Val Tyr Cys Asn Gly Gln Lys Lys Val Ile Leu Thr
        435                 440                 445
Lys Thr Leu Val Ile Gly Gln Cys Ile Tyr Thr Phe Thr Ser Leu Phe
        450                 455                 460
Ser Leu Ile Pro Gly Val Ala His Ser Leu Ala Val Glu Leu Cys Val
465                 470                 475                 480
Pro Gly Leu His Gly Trp Ala Thr Thr Ala Leu Leu Ile Thr Phe Cys
                485                 490                 495
Phe Gly Trp Leu Leu Ile Pro Ala Val Thr Leu Ile Ile Leu Lys Ile
            500                 505                 510
Leu Arg Leu Leu Thr Phe Ser Cys Ser His Tyr Ser Thr Glu Ser Lys
        515                 520                 525
Phe Lys Val Ile Leu Glu Arg Val Lys Val Glu Tyr Gln Lys Thr Met
        530                 535                 540
Gly Ser Met Val Cys Asp Ile Cys His His Glu Cys Glu Thr Ala Lys
545                 550                 555                 560
Glu Leu Glu Thr His Lys Lys Ser Cys Pro Glu Gly Gln Cys Pro Tyr
                565                 570                 575
Cys Met Thr Ile Thr Glu Ser Thr Glu Ser Ala Leu Gln Ala His Phe
            580                 585                 590
Ala Ile Cys Lys Leu Thr Asn Arg Phe Gln Glu Asn Leu Lys Lys Ser
        595                 600                 605
Leu Lys Arg Pro Glu Val Arg Lys Gly Cys Tyr Arg Thr Leu Gly Val
        610                 615                 620
Phe Arg Tyr Lys Ser Arg Cys Tyr Val Gly Leu Val Trp Gly Ile Leu
625                 630                 635                 640
Leu Thr Thr Glu Leu Ile Ile Trp Ala Ala Ser Ala Asp Thr Pro Leu
                645                 650                 655
Met Glu Ser Gly Trp Ser Asp Thr Ala His Gly Val Gly Ile Ile Pro
            660                 665                 670
Met Lys Thr Asp Leu Glu Leu Asp Phe Ala Leu Ala Ser Ser Ser Ser
        675                 680                 685
Tyr Ser Tyr Arg Arg Lys Leu Val Asn Pro Ala Asn Gln Glu Glu Thr
        690                 695                 700
Leu Pro Phe His Phe Gln Leu Asp Lys Gln Val Val His Ala Glu Ile
705                 710                 715                 720
Gln Asn Leu Gly His Trp Met Asp Gly Thr Phe Asn Ile Lys Thr Ala
                725                 730                 735
Phe His Cys Tyr Gly Glu Cys Lys Lys Tyr Ala Tyr Pro Trp Gln Thr
            740                 745                 750
Ala Lys Cys Phe Phe Glu Lys Asp Tyr Gln Tyr Glu Thr Ser Trp Gly
        755                 760                 765
```

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
            805                 810                 815

Gln Thr Cys Lys His Ile Asp Val Asn Asp Cys Leu Val Thr Pro Ser
        820                 825                 830

Val Lys Val Cys Met Ile Gly Thr Ile Ser Lys Leu Gln Pro Gly Asp
    835                 840                 845

Thr Leu Leu Phe Leu Gly Pro Leu Glu Gln Gly Ile Ile Leu Lys
850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
            885                 890                 895

Lys Ile Cys Gly Phe Ala Thr Thr Pro Thr Cys Glu Tyr Gln Gly Asn
        900                 905                 910

Thr Val Ser Gly Phe Gln Arg Met Met Ala Thr Arg Asp Ser Phe Gln
    915                 920                 925

Ser Phe Asn Val Thr Glu Pro His Ile Thr Ser Asn Arg Leu Glu Trp
930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
            965                 970                 975

Leu His Thr Gln Ser Ile Asp Gly Ala Trp Gly Ser Gly Val Gly Phe
        980                 985                 990

Thr Leu Val Cys Thr Val Gly Leu Thr Glu Cys Ala Asn Phe Ile Thr
    995                 1000                1005

Ser Ile Lys Ala Cys Asp Ser Ala Met Cys Tyr Gly Ala Thr Val
    1010            1015                1020

Thr Asn Leu Leu Arg Gly Ser Asn Thr Val Lys Val Val Gly Lys
    1025            1030                1035

Gly Gly His Ser Gly Ser Leu Phe Lys Cys Cys His Asp Thr Asp
    1040            1045                1050

Cys Thr Glu Glu Gly Leu Ala Ala Ser Pro Pro His Leu Asp Arg
    1055            1060                1065

Val Thr Gly Tyr Asn Gln Ile Asp Ser Asp Lys Val Tyr Asp Asp
    1070            1075                1080

Gly Ala Pro Pro Cys Thr Ile Lys Cys Trp Phe Thr Lys Ser Gly
    1085            1090                1095

Glu Trp Leu Leu Gly Ile Leu Asn Gly Asn Trp Val Val Val Ala
    1100            1105                1110

Val Leu Ile Val Ile Leu Ile Leu Ser Ile Leu Leu Phe Ser Phe
    1115            1120                1125

Phe Cys Pro Val Arg Ser Arg Lys Asn Lys Ala Asn
    1130            1135                1140

<210> SEQ ID NO 11
<211> LENGTH: 3671
<212> TYPE: DNA
<213> ORGANISM: Andes virus -continued

```
<400> SEQUENCE: 11
tagtagtaga ctccgcaaga agaagcaaaa aattaaagaa gtgagtttaa aatggaaggg      60
tggtatctgg ttgttcttgg agtctgctat acgctgacac tggcaatgcc caagaccatt    120
tatgagctta aaatggaatg cccgcacact gtgggtctcg gtcaaggtta catcattggc    180
tcaacagaac taggtttgat ctcaattgag gctgcatctg atataaagct cgagagctct    240
tgcaattttg atcttcatac aacatctatg cccagaaga gtttcaccca agttgaatgg    300
agaaagaaaa gtgacacaac tgataccaca aatgctgcgt ccactacctt tgaagcacaa    360
actaaaactg ttaaccttag agggacttgt atactggcac tgaactcta tgatacattg    420
aagaaagtaa aaaagacagt cctgtgctat gatctaacat gtaatcaaac acattgtcag    480
ccaactgtct atctgattgc acctgtattg acatgcatgt caataagaag ttgtatggct    540
agtgtgttta caagcaggat tcaggtgatt tatgaaaaga cacattgtgt aacaggtcag    600
ctgattgagg tcagtgttt caacccagca cacacattga cattatctca gcctgctcac    660
acttatgata ctgtcaccct tcctatctct tgttttttca caccaaagaa gtcggagcaa    720
ctaaaagtta taaaaacatt tgaaggaatt ctgacgaaga caggttgcac ggagaatgca    780
ttgcagggtt attatgtgtg tttttttaggg agtcattcag aacctttaat tgttccgagt    840
ttggaggaca tacggtctgc tgaagttgtt agtaggatgc ttgtacaccc taggggagaa    900
gaccatgatg ccatacagaa ttcacaaagt cacttaagaa tagtgggacc tatcacagca    960
aaagtgccat caactagttc cacagatacc ctaaagggga cagcctttgc aggcgtccca   1020
atgtatagct ctttatctac actagtcaga atgcagacc cagaatttgt attttctcca   1080
ggtatagtac ctgaatctaa tcacagtaca tgtgataaga agacagtacc tatcacatgg   1140
acaggctacc taccaatatc aggtgagatg gaaaaagtga ctggatgtac agttttttgt   1200
acactagcag gacctggtgc tagttgtgag gccattctg aaaatggtat atttaacatc   1260
agttctccaa catgtcttgt aaacaaagtc caaagatttc gtggatctga acagaaaata   1320
aattttatct gtcagcgggt agatcaggat gttgttgtat actgcaatgg gcaaaagaaa   1380
gtcatattaa ccaaaacttt ggttattggg cagtgtattt atacattcac aagcctattt   1440
tcattgatgc ctgatgtagc ccactcattg gctgtagaat tatgtgtccc gggattacat   1500
ggatgggcca ctgtcatgct tctatcaaca ttctgctttg ggtgggtctt gattcctgcg   1560
gtcacattaa taatattaaa gtgtctaagg gttttgacgt tttcttgttc ccattacact   1620
aatgagtcaa aatttaaatt catcctggaa aaagttaaaa ttgaatacca aaagactatg   1680
ggatcaatgg tgtgcgatgt atgtcatcat gagtgtgaaa cagcaaaaga acttgaatca   1740
catagacaga gttgtatcaa tggacaatgt ccttattgca tgcaataac tgaagcaact   1800
gaaagtgcct tgcaagccca ttattccatt tgtaaattga caggaagatt tcaggaggca   1860
ctgaaaaagt cacttaaaaa gccagaggta aaaaaaggtt gttacagaac actcggggta   1920
tttagatata aaagtagatg ttatgtgggt ttggtatggt gcctattgtt gacatgtgaa   1980
attgttattt gggccgcaag tgcagagact ccactaatgg agtcaggctg gtcagatacg   2040
gctcatggtg ttggtgagat tccaatgaag acagacctcg agctggactt tcactgcct   2100
tcttcatcct cttacagtta taggagaaag ctcacaaacc cagccaataa agaagagtct   2160
attcccttcc acttccagat ggaaaaacaa gtaattcatg ctgaaatcca acccctgggt   2220
cattggatgg atgcgacatt taatattaag actgcatttc attgttatgg tgcatgccag   2280
aaatactctt atccatggca gacatctaag tgcttctttg aaaaggacta ccagtatgaa   2340
```

-continued

```
acaggctggg gctgtaatcc tggtgactgc ccaggggttg ggactggatg cactgcttgt    2400
ggtgtttatc tcgataaact aaaatctgtt gggaaggcct ataagataat ttctttaaaa    2460
tataccagaa aggtttgtat tcagttagga acagaacaaa cttgcaagca tattgatgca    2520
aatgattgtt tagtgacacc atctgtgaaa gtttgcatag tgggcacagt ttcaaaactt    2580
caaccatctg atactctttt gttcttaggt ccactagaac aagggggaat cattcttaag    2640
caatggtgca caacatcatg tgcatttggg accctggtg atatcatgtc cactcccagt     2700
ggtatgaggt gtccagagca cactggatca tttaggaaaa tttgcggttt tgctactaca    2760
ccagtttgtg aatatcaagg aaataccatt tctggatata aagaatgat ggcaacaaaa     2820 gattcattcc aatcatttaa cttaacagaa cctcacatca caacaaacaa gcttgaatgg    2880
atcgacccag atgggaatac aagagaccac gtaaaccttg tcttaaatag agatgtctca    2940
tttcaggatt taagtgataa cccctgtaaa gtagacctac acacacaagc aatagaaggg    3000
gcatggggtt ctggtgtagg gtttacactc acatgtactg tcggattaac agagtgccca    3060
agttttatga catcaattaa ggcatgtgac ctagctatgt gttatggatc aacagtaaca    3120
aaccttgcca ggggctctaa tacagtgaaa gtagttggta aaggaggcca ttcagggtcc    3180
tcatttaaat gctgtcatga tacagattgc tcctctgaag gtttacttgc atcagcccct    3240
catcttgaga gggtaacagg attcaatcaa attgattcag ataaggttta tgatgatggt    3300
gcaccacctt gcacattcaa atgctggttc actaagtcag gtgagtggct tcttgggatc    3360
ttaaacggga attggattgt tgttgtagtg cttgttgtga tactcattct ctctatcata    3420
atgttcagtg ttttgtgtcc caggagaggg cacaagaaaa ctgtctaagc attgacctca    3480
actcctacat tagatcatat acatttatgc acttcctcat atttagctgc actaagatat    3540
taataaactc tagttattga ctttataaga ttattatgga actaacctca cttaaaaaaa    3600
acaaatactt tactcatata taactccata ttctcttacc gaggcttttg ttcctgcgga    3660
gcatactact a                                                         3671
```

<210> SEQ ID NO 12
<211> LENGTH: 1138
<212> TYPE: PRT
<213> ORGANISM: Andes virus

<400> SEQUENCE: 12

```
Met Glu Gly Trp Tyr Leu Val Val Leu Gly Val Cys Tyr Thr Leu Thr
1               5                   10                  15

Leu Ala Met Pro Lys Thr Ile Tyr Glu Leu Lys Met Glu Cys Pro His
                20                  25                  30

Thr Val Gly Leu Gly Gln Gly Tyr Ile Ile Gly Ser Thr Glu Leu Gly
            35                  40                  45

Leu Ile Ser Ile Glu Ala Ala Ser Asp Ile Lys Leu Glu Ser Ser Cys
        50                  55                  60

Asn Phe Asp Leu His Thr Thr Ser Met Ala Gln Lys Ser Phe Thr Gln
65                  70                  75                  80

Val Glu Trp Arg Lys Lys Ser Asp Thr Thr Asp Thr Asn Ala Ala
                85                  90                  95

Ser Thr Thr Phe Glu Ala Gln Thr Lys Thr Val Asn Leu Arg Gly Thr
            100                 105                 110

Cys Ile Leu Ala Pro Glu Leu Tyr Asp Thr Leu Lys Lys Val Lys Lys
        115                 120                 125
```

-continued

```
Thr Val Leu Cys Tyr Asp Leu Thr Cys Asn Gln Thr His Cys Gln Pro
    130                 135                 140

Thr Val Tyr Leu Ile Ala Pro Val Leu Thr Cys Met Ser Ile Arg Ser
145                 150                 155                 160

Cys Met Ala Ser Val Phe Thr Ser Arg Ile Gln Val Ile Tyr Glu Lys
                165                 170                 175

Thr His Cys Val Thr Gly Gln Leu Ile Glu Gly Gln Cys Phe Asn Pro
                180                 185                 190

Ala His Thr Leu Thr Leu Ser Gln Pro Ala His Thr Tyr Asp Thr Val
            195                 200                 205

Thr Leu Pro Ile Ser Cys Phe Phe Thr Pro Lys Lys Ser Glu Gln Leu
    210                 215                 220

Lys Val Ile Lys Thr Phe Glu Gly Ile Leu Thr Lys Thr Gly Cys Thr
225                 230                 235                 240

Glu Asn Ala Leu Gln Gly Tyr Tyr Val Cys Phe Leu Gly Ser His Ser
                245                 250                 255

Glu Pro Leu Ile Val Pro Ser Leu Glu Asp Ile Arg Ser Ala Glu Val
                260                 265                 270

Val Ser Arg Met Leu Val His Pro Arg Gly Glu Asp His Asp Ala Ile
            275                 280                 285

Gln Asn Ser Gln Ser His Leu Arg Ile Val Gly Pro Ile Thr Ala Lys
    290                 295                 300

Val Pro Ser Thr Ser Ser Thr Asp Thr Leu Lys Gly Thr Ala Phe Ala
305                 310                 315                 320

Gly Val Pro Met Tyr Ser Ser Leu Ser Thr Leu Val Arg Asn Ala Asp
                325                 330                 335

Pro Glu Phe Val Phe Ser Pro Gly Ile Val Pro Glu Ser Asn His Ser
                340                 345                 350

Thr Cys Asp Lys Lys Thr Val Pro Ile Thr Trp Thr Gly Tyr Leu Pro
            355                 360                 365

Ile Ser Gly Glu Met Glu Lys Val Thr Gly Cys Thr Val Phe Cys Thr
    370                 375                 380

Leu Ala Gly Pro Gly Ala Ser Cys Glu Ala Tyr Ser Glu Asn Gly Ile
385                 390                 395                 400

Phe Asn Ile Ser Ser Pro Thr Cys Leu Val Asn Lys Val Gln Arg Phe
                405                 410                 415

Arg Gly Ser Glu Gln Lys Ile Asn Phe Ile Cys Gln Arg Val Asp Gln
            420                 425                 430

Asp Val Val Tyr Cys Asn Gly Gln Lys Val Ile Leu Thr Lys
            435                 440                 445

Thr Leu Val Ile Gly Gln Cys Ile Tyr Thr Phe Thr Ser Leu Phe Ser
    450                 455                 460

Leu Met Pro Asp Val Ala His Ser Leu Ala Val Glu Leu Cys Val Pro
465                 470                 475                 480

Gly Leu His Gly Trp Ala Thr Val Met Leu Leu Ser Thr Phe Cys Phe
                485                 490                 495

Gly Trp Val Leu Ile Pro Ala Val Thr Leu Ile Ile Leu Lys Cys Leu
                500                 505                 510

Arg Val Leu Thr Phe Ser Cys Ser His Tyr Thr Asn Glu Ser Lys Phe
            515                 520                 525

Lys Phe Ile Leu Glu Lys Val Lys Ile Glu Tyr Gln Lys Thr Met Gly
    530                 535                 540

Ser Met Val Cys Asp Val Cys His His Glu Cys Glu Thr Ala Lys Glu
```

```
           545                 550                 555                 560
Leu Glu Ser His Arg Gln Ser Cys Ile Asn Gly Gln Cys Pro Tyr Cys
                565                 570                 575

Met Thr Ile Thr Glu Ala Thr Glu Ser Ala Leu Gln Ala His Tyr Ser
                580                 585                 590

Ile Cys Lys Leu Thr Gly Arg Phe Gln Glu Ala Leu Lys Lys Ser Leu
                595                 600                 605

Lys Lys Pro Glu Val Lys Gly Cys Tyr Arg Thr Leu Gly Val Phe
            610                 615                 620

Arg Tyr Lys Ser Arg Cys Tyr Val Gly Leu Val Trp Cys Leu Leu
625                 630                 635                 640

Thr Cys Glu Ile Val Ile Trp Ala Ala Ser Ala Glu Thr Pro Leu Met
                645                 650                 655

Glu Ser Gly Trp Ser Asp Thr Ala His Gly Val Gly Glu Ile Pro Met
                660                 665                 670

Lys Thr Asp Leu Glu Leu Asp Phe Ser Leu Pro Ser Ser Ser Tyr
            675                 680                 685

Ser Tyr Arg Arg Lys Leu Thr Asn Pro Ala Asn Lys Glu Glu Ser Ile
            690                 695                 700

Pro Phe His Phe Gln Met Glu Lys Gln Val Ile His Ala Glu Ile Gln
705                 710                 715                 720

Pro Leu Gly His Trp Met Asp Ala Thr Phe Asn Ile Lys Thr Ala Phe
                725                 730                 735

His Cys Tyr Gly Ala Cys Gln Lys Tyr Ser Tyr Pro Trp Gln Thr Ser
                740                 745                 750

Lys Cys Phe Phe Glu Lys Asp Tyr Gln Tyr Glu Thr Gly Trp Gly Cys
                755                 760                 765

Asn Pro Gly Asp Cys Pro Gly Val Gly Thr Gly Cys Thr Ala Cys Gly
                770                 775                 780

Val Tyr Leu Asp Lys Leu Lys Ser Val Gly Lys Ala Tyr Lys Ile Ile
785                 790                 795                 800

Ser Leu Lys Tyr Thr Arg Lys Val Cys Ile Gln Leu Gly Thr Glu Gln
                805                 810                 815

Thr Cys Lys His Ile Asp Ala Asn Asp Cys Leu Val Thr Pro Ser Val
                820                 825                 830

Lys Val Cys Ile Val Gly Thr Val Ser Lys Leu Gln Pro Ser Asp Thr
            835                 840                 845

Leu Leu Phe Leu Gly Pro Leu Glu Gln Gly Gly Ile Ile Leu Lys Gln
            850                 855                 860

Trp Cys Thr Thr Ser Cys Ala Phe Gly Asp Pro Gly Asp Ile Met Ser
865                 870                 875                 880

Thr Pro Ser Gly Met Arg Cys Pro Glu His Thr Gly Ser Phe Arg Lys
                885                 890                 895

Ile Cys Gly Phe Ala Thr Thr Pro Val Cys Glu Tyr Gln Gly Asn Thr
            900                 905                 910

Ile Ser Gly Tyr Lys Arg Met Met Ala Thr Lys Asp Ser Phe Gln Ser
            915                 920                 925

Phe Asn Leu Thr Glu Pro His Ile Thr Thr Asn Lys Leu Glu Trp Ile
            930                 935                 940

Asp Pro Asp Gly Asn Thr Arg Asp His Val Asn Leu Val Leu Asn Arg
945                 950                 955                 960

Asp Val Ser Phe Gln Asp Leu Ser Asp Asn Pro Cys Lys Val Asp Leu
                965                 970                 975
```

-continued

```
His Thr Gln Ala Ile Glu Gly Ala Trp Gly Ser Gly Val Gly Phe Thr
            980                 985                 990

Leu Thr Cys Thr Val Gly Leu Thr  Glu Cys Pro Ser Phe  Met Thr Ser
        995                 1000                1005

Ile Lys  Ala Cys Asp Leu Ala  Met Cys Tyr Gly Ser  Thr Val Thr
    1010                 1015                 1020

Asn Leu  Ala Arg Gly Ser Asn  Thr Val Lys Val Val  Gly Lys Gly
    1025                 1030                 1035

Gly His  Ser Gly Ser Ser Phe  Lys Cys Cys His Asp  Thr Asp Cys
    1040                 1045                 1050

Ser Ser  Glu Gly Leu Leu Ala  Ser Ala Pro His Leu  Glu Arg Val
    1055                 1060                 1065

Thr Gly  Phe Asn Gln Ile Asp  Ser Asp Lys Val Tyr  Asp Asp Gly
    1070                 1075                 1080

Ala Pro  Pro Cys Thr Phe Lys  Cys Trp Phe Thr Lys  Ser Gly Glu
    1085                 1090                 1095

Trp Leu  Leu Gly Ile Leu Asn  Gly Asn Trp Ile Val  Val Val Val
    1100                 1105                 1110

Leu Val  Val Ile Leu Ile Leu  Ser Ile Ile Met Phe  Ser Val Leu
    1115                 1120                 1125

Cys Pro  Arg Arg Gly His Lys  Lys Thr Val
    1130                 1135

<210> SEQ ID NO 13
<211> LENGTH: 249
<212> TYPE: DNA
<213> ORGANISM: Hantaan virus

<400> SEQUENCE: 13
atgagttttg gggaaaacag tgtgataggt tatgtagaat acccccccgt gccattggcc      60
gacacagcac agatggtgcc tgagagttct tgtaacatgg ataatcacca atcgttgaat    120
acaataacaa aatatacccca agtaagttgg agaggaaagg ctgatcagtc acagtctagt    180
caaaattcat ttgagacagt gtccactgaa gttgacttga aaggaacatg tgttctaaaa    240
cactaatag                                                            249

<210> SEQ ID NO 14
<211> LENGTH: 81
<212> TYPE: PRT
<213> ORGANISM: Hantaan virus

<400> SEQUENCE: 14

Met Ser Phe Gly Glu Asn Ser Val Ile Gly Tyr Val Glu Leu Pro Pro
1               5                   10                  15

Val Pro Leu Ala Asp Thr Ala Gln Met Val Pro Glu Ser Ser Cys Asn
            20                  25                  30

Met Asp Asn His Gln Ser Leu Asn Thr Ile Thr Lys Tyr Thr Gln Val
        35                  40                  45

Ser Trp Arg Gly Lys Ala Asp Gln Ser Gln Ser Gln Asn Ser Phe
    50                  55                  60

Glu Thr Val Ser Thr Glu Val Asp Leu Lys Gly Thr Cys Val Leu Lys
65                  70                  75                  80

His

<210> SEQ ID NO 15
```

<210> SEQ ID NO 15
<211> LENGTH: 258
<212> TYPE: DNA
<213> ORGANISM: Puumala virus

<400> SEQUENCE: 15

```
atgagattag ggcagggtct tgttgtgggt tcagtagaat tgccatctct tccaatacag    60
caggtcgaga cactaaagct ggagagttct tgtaattttg atctacatac cagtacagca   120
ggacaacaat cattcacaaa atggacatgg gaaattaaag gtgatcttgc agagaacaca   180
caggcatcat caacaagttt tcaaacaaaa agcagtgaag tgaatttgag aggattatgt   240
ttgatcccta cttaatag                                                 258
```

<210> SEQ ID NO 16
<211> LENGTH: 84
<212> TYPE: PRT
<213> ORGANISM: Puumala virus

<400> SEQUENCE: 16

```
Met Arg Leu Gly Gln Gly Leu Val Val Gly Ser Val Glu Leu Pro Ser
1               5                   10                  15

Leu Pro Ile Gln Gln Val Glu Thr Leu Lys Leu Glu Ser Ser Cys Asn
            20                  25                  30

Phe Asp Leu His Thr Ser Thr Ala Gly Gln Gln Ser Phe Thr Lys Trp
        35                  40                  45

Thr Trp Glu Ile Lys Gly Asp Leu Ala Glu Asn Thr Gln Ala Ser Ser
    50                  55                  60

Thr Ser Phe Gln Thr Lys Ser Ser Glu Val Asn Leu Arg Gly Leu Cys
65                  70                  75                  80

Leu Ile Pro Thr
```

<210> SEQ ID NO 17
<211> LENGTH: 249
<212> TYPE: DNA
<213> ORGANISM: Seoul virus

<400> SEQUENCE: 17

```
atgaaatttg gggaaacaag tgtgtcaggc tacacagaac tgcccccact ctcattacag    60
gaggcagaac agctggtgcc agagagctca tgcaacatgg acaaccacca atcactctca   120
acaataaata aattaaccaa ggtcatatgg cggaaaaagg caaatcagga atcagcaaac   180
cagaattcat ttgaacttat ggagagtgaa gtcagcttta aagggttgtg tatgttaaag   240
cattaatag                                                           249
```

<210> SEQ ID NO 18
<211> LENGTH: 81
<212> TYPE: PRT
<213> ORGANISM: Seoul virus

<400> SEQUENCE: 18

```
Met Lys Phe Gly Glu Thr Ser Val Ser Gly Tyr Thr Glu Leu Pro Pro
1               5                   10                  15

Leu Ser Leu Gln Glu Ala Glu Gln Leu Val Pro Glu Ser Ser Cys Asn
            20                  25                  30

Met Asp Asn His Gln Ser Leu Ser Thr Ile Asn Lys Leu Thr Lys Val
        35                  40                  45

Ile Trp Arg Lys Lys Ala Asn Gln Glu Ser Ala Asn Gln Asn Ser Phe
    50                  55                  60
```

```
Glu Leu Met Glu Ser Glu Val Ser Phe Lys Gly Leu Cys Met Leu Lys
 65                  70                  75                  80

His

<210> SEQ ID NO 19
<211> LENGTH: 249
<212> TYPE: DNA
<213> ORGANISM: Dobrava virus

<400> SEQUENCE: 19
atgaactttg gggagagcag tgtaacaggt aaggtggaat taccacccct tctgctcaca      60
gatgcagagg ccttggtccc ggagagttct tgtaacatgg acaaccatca gtctatgtca     120
attatacaaa aagtgacaaa agtgagttgg agaaaaaagg cagacaaagc ccaagctgcc     180
aaggactcat ttgagacaac atcaagcgag gttaatctga aggggacatg cacattgagt     240
cattaatag                                                             249

<210> SEQ ID NO 20
<211> LENGTH: 81
<212> TYPE: PRT
<213> ORGANISM: Dobrava virus

<400> SEQUENCE: 20

Met Asn Phe Gly Glu Ser Ser Val Thr Gly Lys Val Glu Leu Pro Pro
  1               5                  10                  15

Leu Leu Leu Thr Asp Ala Glu Ala Leu Val Pro Glu Ser Ser Cys Asn
                 20                  25                  30

Met Asp Asn His Gln Ser Met Ser Ile Ile Gln Lys Val Thr Lys Val
             35                  40                  45

Ser Trp Arg Lys Lys Ala Asp Lys Ala Gln Ala Ala Lys Asp Ser Phe
         50                  55                  60

Glu Thr Thr Ser Ser Glu Val Asn Leu Lys Gly Thr Cys Thr Leu Ser
 65                  70                  75                  80

His

<210> SEQ ID NO 21
<211> LENGTH: 258
<212> TYPE: DNA
<213> ORGANISM: Sin Nombre hantavirus

<400> SEQUENCE: 21
atgggtttag gtcagggtta cgtgacaggt tcagtggaaa ttacacctat tctcttaacg      60
caggtagctg atctgaagat tgagagttct tgtaatttcg atttgcatgt cccggctacc     120
actacccaaa aatacaatca ggttgactgg accaaaaaaa gttcaactac agaaagcaca     180
aatgcaggtg caactacatt tgaggctaaa acaaagagag taaatttgaa aggcacatgt     240
aatattcctc cataatag                                                   258

<210> SEQ ID NO 22
<211> LENGTH: 84
<212> TYPE: PRT
<213> ORGANISM: Sin Nombre hantavirus

<400> SEQUENCE: 22

Met Gly Leu Gly Gln Gly Tyr Val Thr Gly Ser Val Glu Ile Thr Pro
  1               5                  10                  15

Ile Leu Leu Thr Gln Val Ala Asp Leu Lys Ile Glu Ser Ser Cys Asn
                 20                  25                  30
```

Phe Asp Leu His Val Pro Ala Thr Thr Thr Gln Lys Tyr Asn Gln Val
            35                  40                  45

Asp Trp Thr Lys Lys Ser Ser Thr Glu Ser Thr Asn Ala Gly Ala
    50                  55                  60

Thr Thr Phe Glu Ala Lys Thr Lys Glu Ile Asn Leu Lys Gly Thr Cys
65                  70                  75                  80

Asn Ile Pro Pro

<210> SEQ ID NO 23
<211> LENGTH: 258
<212> TYPE: DNA
<213> ORGANISM: Andes virus

<400> SEQUENCE: 23
atgggtctcg gtcaaggtta catcattggc tcaacagaac taggtttgat ctcaattgag      60
gctgcatctg atataaagct cgagagctct tgcaattttg atcttcatac aacatctatg     120
gcccagaaga gtttcaccca agttgaatgg agaagaaaa gtgacacaac tgataccaca     180
aatgctgcgt ccactacctt tgaagcacaa actaaaactg ttaaccttag agggacttgt     240
atactggcac cttaatag                                                   258

<210> SEQ ID NO 24
<211> LENGTH: 84
<212> TYPE: PRT
<213> ORGANISM: Andes virus

<400> SEQUENCE: 24

Met Gly Leu Gly Gln Gly Tyr Ile Ile Gly Ser Thr Glu Leu Gly Leu
1               5                   10                  15

Ile Ser Ile Glu Ala Ala Ser Asp Ile Lys Leu Glu Ser Ser Cys Asn
            20                  25                  30

Phe Asp Leu His Thr Thr Ser Met Ala Gln Lys Ser Phe Thr Gln Val
            35                  40                  45

Glu Trp Arg Lys Lys Ser Asp Thr Thr Asp Thr Asn Ala Ala Ser
    50                  55                  60

Thr Thr Phe Glu Ala Gln Thr Lys Val Asn Leu Arg Gly Thr Cys
65                  70                  75                  80

Ile Leu Ala Pro

<210> SEQ ID NO 25
<211> LENGTH: 1293
<212> TYPE: DNA
<213> ORGANISM: Hantaan virus

<400> SEQUENCE: 25
atggcaacta tggaggaatt acagagggaa atcaatgccc atgagggtca attagtgata      60
gccaggcaga aggtgaggga tgcagaaaaa cagtatgaaa aggatccaga tgagttgaac     120
aagagaacat taactgaccg agagggcgtt gcagtatcta tccaggcaaa aattgatgag     180
ttaaaaaggc aactggcaga taggattgca actgggaaaa accttgggaa ggaacaagat     240
ccaacagggg tggagcctgg agaccatctg aagagaggt caatgctcag ttatggtaat     300
gtgctggatt taaaccattt ggatattgat gaacctacag acagacagc agactggctg     360 agcatcatcg tctatcttac atcctttgtc gtcccgatac ttctgaaagc tctgtatatg     420
ttgacaacaa gggggaggca aactaccaag gataataaag ggaccgggat tcgatttaag    480

-continued

```
gatgatagct cgttcgagga tgttaacggt atccggaaac caaaacatct ttacgtgtcc      540
ttgccaaatg cacagtcaag catgaaggca gaagagatta cacctggtag atatagaaca      600
gcagtctgtg ggctctaccc tgcacagatt aaggcacggc agatgatcag tccagttatg      660
agtgtaattg gtttctagc attagcaaag gactggagtg atcgtatcga acaatggtta       720
attgaacctt gcaagcttct tccagataca gcagcagtta gcctccttgg tggtcctgca      780
acaaacaggg actacttacg gcagcggcaa gtggcattag caatatgga gacaaaggag       840 tcaaaggcta tacgccagca tgcagaagca gctggctgta gcatgattga agatattgag      900
tcaccatcat caatatgggt ttttgctgga gcaccagacc gttgtccacc aacatgtttg      960
tttatagcag gtattgctga gcttggggca ttttttttcca tcctgcagga catgcgaaat    1020
acaatcatgg catctaagac agttggaaca tctgaggaga agctacggaa gaaatcatca    1080
ttttatcagt cctacctcag aaggacacaa tcaatgggga tacaactagg ccagagaatt    1140
attgtgctct tcatggttgc ctggggaaag gaggctgtgg acaacttcca cttagggggat  1200 gatatggatc ctgagctaag gacactggca cagagcttga ttgatgtcaa agtgaaggaa    1260
atctccaacc aagagccttt gaaactctaa tag                                  1293
```

<210> SEQ ID NO 26
<211> LENGTH: 429
<212> TYPE: PRT
<213> ORGANISM: Hantaan virus

<400> SEQUENCE: 26

```
Met Ala Thr Met Glu Glu Leu Gln Arg Glu Ile Asn Ala His Glu Gly
1               5                   10                  15

Gln Leu Val Ile Ala Arg Gln Lys Val Arg Asp Ala Glu Lys Gln Tyr
            20                  25                  30

Glu Lys Asp Pro Asp Glu Leu Asn Lys Arg Thr Leu Thr Asp Arg Glu
        35                  40                  45

Gly Val Ala Val Ser Ile Gln Ala Lys Ile Asp Glu Leu Lys Arg Gln
    50                  55                  60

Leu Ala Asp Arg Ile Ala Thr Gly Lys Asn Leu Gly Lys Glu Gln Asp
65                  70                  75                  80

Pro Thr Gly Val Glu Pro Gly Asp His Leu Lys Glu Arg Ser Met Leu
                85                  90                  95

Ser Tyr Gly Asn Val Leu Asp Leu Asn His Leu Asp Ile Asp Glu Pro
            100                 105                 110

Thr Gly Gln Thr Ala Asp Trp Leu Ser Ile Ile Val Tyr Leu Thr Ser
        115                 120                 125

Phe Val Val Pro Ile Leu Leu Lys Ala Leu Tyr Met Leu Thr Thr Arg
    130                 135                 140

Gly Arg Gln Thr Thr Lys Asp Asn Lys Gly Thr Arg Ile Arg Phe Lys
145                 150                 155                 160

Asp Asp Ser Ser Phe Glu Asp Val Asn Gly Ile Arg Lys Pro Lys His
                165                 170                 175

Leu Tyr Val Ser Leu Pro Asn Ala Gln Ser Ser Met Lys Ala Glu Glu
            180                 185                 190

Ile Thr Pro Gly Arg Tyr Arg Thr Ala Val Cys Gly Leu Tyr Pro Ala
        195                 200                 205

Gln Ile Lys Ala Arg Gln Met Ile Ser Pro Val Met Ser Val Ile Gly
    210                 215                 220

Phe Leu Ala Leu Ala Lys Asp Trp Ser Asp Arg Ile Glu Gln Trp Leu
```

```
                225                 230                 235                 240
Ile Glu Pro Cys Lys Leu Leu Pro Asp Thr Ala Ala Val Ser Leu Leu
                    245                 250                 255
Gly Gly Pro Ala Thr Asn Arg Asp Tyr Leu Arg Gln Arg Gln Val Ala
                260                 265                 270
Leu Gly Asn Met Glu Thr Lys Glu Ser Lys Ala Ile Arg Gln His Ala
            275                 280                 285
Glu Ala Ala Gly Cys Ser Met Ile Glu Asp Ile Glu Ser Pro Ser Ser
        290                 295                 300
Ile Trp Val Phe Ala Gly Ala Pro Asp Arg Cys Pro Pro Thr Cys Leu
305                 310                 315                 320
Phe Ile Ala Gly Ile Ala Glu Leu Gly Ala Phe Phe Ser Ile Leu Gln
                325                 330                 335
Asp Met Arg Asn Thr Ile Met Ala Ser Lys Thr Val Gly Thr Ser Glu
                340                 345                 350
Glu Lys Leu Arg Lys Lys Ser Ser Phe Tyr Gln Ser Tyr Leu Arg Arg
            355                 360                 365
Thr Gln Ser Met Gly Ile Gln Leu Gly Gln Arg Ile Ile Val Leu Phe
        370                 375                 380
Met Val Ala Trp Gly Lys Glu Ala Val Asp Asn Phe His Leu Gly Asp
385                 390                 395                 400
Asp Met Asp Pro Glu Leu Arg Thr Leu Ala Gln Ser Leu Ile Asp Val
                405                 410                 415
Lys Val Lys Glu Ile Ser Asn Gln Glu Pro Leu Lys Leu
                420                 425

<210> SEQ ID NO 27
<211> LENGTH: 1305
<212> TYPE: DNA
<213> ORGANISM: Puumala virus

<400> SEQUENCE: 27
atgagtgact tgacagacat ccaagaggag ataacccgcc atgagcaaca acttgttgtt      60
gccagacaaa aactcaagga tgcagagaga gcagtggaag tgtacccgga tgacgttaac     120
aagaacacat acaagcaag acaacaaaca gtgtcagcac tggaggataa actcgcagac     180
tacaagagaa gaatggcaga tgctgtgtcc cggaagaaaa tggatactaa acctactgac     240
ccgactggga ttgaacctga tgatcatctc aaggagagat caagccttag atatggaaat     300
gtccttgatg tgaatgctat tgacattgaa gaaccaagtg ccagacagc agattggtat      360 actatcggag tctatgtaat agggttcaca attcctatca ttttgaaggc tctatatatg     420
ttgtcaacac gtggaagaca gactgtaaag gaaaacaaag gaacacggat caggttcaag     480
gatgacacat catttgagga tatcaatggc atcaggagac caaaacacct atatgtatcc     540
atgcctactg cccagtccac catgaaagct gaagaactta cacctggacg gttccgtaca     600
atagtatgtg gcttattccc tacacagata caagttcgta acatcatgag tccagtaatg     660
ggagtgattg gttttctttt cttcgttaaa gactggccag aaaaaattag ggagtttatg     720
gagaaagaat gccctttcat aaagccagaa gttaaacctg gacaccagc acaggaggta     780 gaattttga aaagaaatag agtttatttc atgacccgcc aggatgttct tgacaaaaat      840
catgtggctg acatcgataa gttgattgac tatgctgccg ctggtgaccc tacatcgcct     900
gatgacatcg aatctcctaa tgcaccatgg gtatttgctt gtgcaccaga tcggtgcccc     960
ccaacatgta tttatgttgc tgggatggct gaattaggtg cattctttc catcttacag     1020
```

```
gatatgagga acaccattat ggcatctaaa actgtgggca cagcagaaga gaaactgaaa   1080
aagaagtcct ccttctatca atcatatttg cgccgaacac aatcaatggg gattcaactt   1140
gatcagagga taatcctact gtacatgttg aatggggaa aagaaatggt ggatcatttc   1200
catcttggtg atggcatgga tcctgagcta aggggccttg ctcagtcact catagaccag   1260
aaggtaaaag agatatcaaa ccaagaaccc ttaaagatat gatag                   1305
```

<210> SEQ ID NO 28
<211> LENGTH: 433
<212> TYPE: PRT
<213> ORGANISM: Puumala virus

<400> SEQUENCE: 28

```
Met Ser Asp Leu Thr Asp Ile Gln Glu Glu Ile Thr Arg His Glu Gln
1               5                   10                  15

Gln Leu Val Val Ala Arg Gln Lys Leu Lys Asp Ala Glu Arg Ala Val
            20                  25                  30

Glu Val Tyr Pro Asp Asp Val Asn Lys Asn Thr Leu Gln Ala Arg Gln
        35                  40                  45

Gln Thr Val Ser Ala Leu Glu Asp Lys Leu Ala Asp Tyr Lys Arg Arg
    50                  55                  60

Met Ala Asp Ala Val Ser Arg Lys Lys Met Asp Thr Lys Pro Thr Asp
65                  70                  75                  80

Pro Thr Gly Ile Glu Pro Asp Asp His Leu Lys Glu Arg Ser Ser Leu
                85                  90                  95

Arg Tyr Gly Asn Val Leu Asp Val Asn Ala Ile Asp Ile Glu Glu Pro
            100                 105                 110

Ser Gly Gln Thr Ala Asp Trp Tyr Thr Ile Gly Val Tyr Val Ile Gly
        115                 120                 125

Phe Thr Ile Pro Ile Ile Leu Lys Ala Leu Tyr Met Leu Ser Thr Arg
    130                 135                 140

Gly Arg Gln Thr Val Lys Glu Asn Lys Gly Thr Arg Ile Arg Phe Lys
145                 150                 155                 160

Asp Asp Thr Ser Phe Glu Asp Ile Asn Gly Ile Arg Arg Pro Lys His
                165                 170                 175

Leu Tyr Val Ser Met Pro Thr Ala Gln Ser Thr Met Lys Ala Glu Glu
            180                 185                 190

Leu Thr Pro Gly Arg Phe Arg Thr Ile Val Cys Gly Leu Phe Pro Thr
        195                 200                 205

Gln Ile Gln Val Arg Asn Ile Met Ser Pro Val Met Gly Val Ile Gly
    210                 215                 220

Phe Ser Phe Phe Val Lys Asp Trp Pro Glu Lys Ile Arg Glu Phe Met
225                 230                 235                 240

Glu Lys Glu Cys Pro Phe Ile Lys Pro Glu Val Lys Pro Gly Thr Pro
                245                 250                 255

Ala Gln Glu Val Glu Phe Leu Lys Arg Asn Arg Val Tyr Phe Met Thr
            260                 265                 270

Arg Gln Asp Val Leu Asp Lys Asn His Val Ala Asp Ile Asp Lys Leu
        275                 280                 285

Ile Asp Tyr Ala Ala Ala Gly Asp Pro Thr Ser Pro Asp Asp Ile Glu
    290                 295                 300

Ser Pro Asn Ala Pro Trp Val Phe Ala Cys Ala Pro Asp Arg Cys Pro
305                 310                 315                 320
```

```
Pro Thr Cys Ile Tyr Val Ala Gly Met Ala Glu Leu Gly Ala Phe Phe
            325                 330                 335

Ser Ile Leu Gln Asp Met Arg Asn Thr Ile Met Ala Ser Lys Thr Val
            340                 345                 350

Gly Thr Ala Glu Glu Lys Leu Lys Lys Ser Ser Phe Tyr Gln Ser
            355                 360                 365

Tyr Leu Arg Arg Thr Gln Ser Met Gly Ile Gln Leu Asp Gln Arg Ile
        370                 375                 380

Ile Leu Leu Tyr Met Leu Glu Trp Gly Lys Glu Met Val Asp His Phe
385                 390                 395                 400

His Leu Gly Asp Gly Met Asp Pro Glu Leu Arg Gly Leu Ala Gln Ser
                405                 410                 415

Leu Ile Asp Gln Lys Val Lys Glu Ile Ser Asn Gln Glu Pro Leu Lys
            420                 425                 430

Ile

<210> SEQ ID NO 29
<211> LENGTH: 1293
<212> TYPE: DNA
<213> ORGANISM: Seoul virus

<400> SEQUENCE: 29
atggcaacta tggaggaaat ccagagagaa atcagtgctc acgagggca gcttgtgata      60 gcacgccaga aggtcaagga tgcagaaaag cagtatgaga aggatcctga tgacttaaac    120
aagagggcac tgcatgatcg ggagagtgtc gcagcttcaa tacaatcaaa aattgatgaa    180
ctgaagcgcc aacttgccga caggattgca gcagggaaga acatcgggca agaccgggat    240
cctacagggg tagagccggg tgatcatctc aaggaaagat cagcactaag ctacgggaat    300
acactggacc tgaatagtct tgacattgat gaacctacag acaaacagc tgattggctg    360 actataattg tctatctaac atcattcgtg gtcccgatca tcttgaaggc actgtacatg    420
ttaacaacaa gaggtaggca gacttcaaag gacaacaagg ggatgaggat cagattcaag    480
gatgacagct catatgagga tgtcaatggg atcagaaagc ctaaacatct gtatgtgtca    540
atgccaaacg cccaatccag tatgaaggct gaagagataa caccaggaag attccgcact    600
gcagtatgtg gctatatcc tgcacagata aaggcaagga atatggtaag ccctgtcatg    660
agtgtagttg ggtttttggc actagcaaaa gactggacat ctagaattga agaatggctt    720
ggcgcaccct gcaagttcat ggcagagtct cctattgctg ggagtttatc tgggaatcct    780
gtgaatcgtg actatatcag acaaagacaa ggtgcacttg cagggatgga gccaaaggaa    840
tttcaagccc tcaggcaaca ttcaaaggat gctggatgta cactagttga acatattgag    900
tcaccatcgt caatatgggt gtttgctggg gcccctgata ggtgtccacc aacatgcttg    960
tttgttggag ggatggctga gttaggtgcc ttcttttcta tacttcagga tatgaggaac   1020
acaatcatgg cttcaaaaac tgtgggcaca gctgatgaaa agcttcgaaa gaaatcatca   1080
ttctatcaat cataccctcag acgcacacaa tcaatgggaa tacaactgga ccagaggata   1140
attgttatgt ttatggttgc ctggggaaag gaggcagtgg acaacttcca tctcggtgat   1200
gacatggatc cagagcttcg tagcctggct cagatcttga ttgaccagaa agtgaaggaa   1260
atctcgaacc aggagcctat gaaattataa tag                                1293

<210> SEQ ID NO 30
<211> LENGTH: 429
<212> TYPE: PRT
```

<213> ORGANISM: Seoul virus

<400> SEQUENCE: 30

Met Ala Thr Met Glu Glu Ile Gln Arg Glu Ile Ser

```
Asp Met Asp Pro Glu Leu Arg Ser Leu Ala Gln Ile Leu Ile Asp Gln
            405                 410                 415

Lys Val Lys Glu Ile Ser Asn Gln Glu Pro Met Lys Leu
        420                 425

<210> SEQ ID NO 31
<211> LENGTH: 1293
<212> TYPE: DNA
<213> ORGANISM: Dobrava virus

<400> SEQUENCE: 31
atggcaacat tagaggaact ccaaaaggaa atcaacaacc atgaaggtca attggtgata      60
gccaggcaga aggtgaagga tgcagaaaag cagtatgaaa aggaccctga cgacctgaat     120
aaaagggcat tgagtgatcg ggaaagcatt gcacaatcaa ttcagggaaa atcgatgaa     180 ttaaggagac agctggctga tcgtgtggca gcagggaaaa acatcggcaa agaaagggac     240
ccaactgggc tagaccctgg agatcacctc aaagagaagt caatgctcag ttatggaaat     300
gtcattgacc tcaaccatct tgacattgat gaacctacag ggcaaactgc agactggcta     360
agcattgtga tctacctgac atcattcgtg gtcccaatac tgttgaaggc tctttacatg     420
cttaccacca gagggagaca aactactaaa gacaataagg gaatgaggat tcgatttaag     480
gatgacagct cttttgaaga tgtgaatggg attcgaaagc caaagcacct gttcttgtca     540
atgcccaatg cacaatctag tatgaaggca gatgagatta caccaggtcg gttcaggact     600
gcaatctgtg gactataccc agcccaggtt aaggcaagga atttaatcag tcctgtgatg     660
agtgtgattg ggtttgtagc ccttgcaaaa aactggacag aacgggttga agaatggctt     720
gacctcccgt gcaagctact atctgagcca tctccaacgt cttttgaccaa aggcccatcc     780 accaatcgtg actacttgaa tcaaagacaa ggagcgcttg caaaaatgga aacgaaggaa     840
gctcaggctg tgaggaaaca tgccatagat gctggttgca acctcattga ccatatagac     900
tcaccatcat caatctgggt cttttgcagga gcacctgata gatgccctcc tacctgcctg     960
tttattgcag gcatggcaga gctaggtgca ttctttgctt gcctccagga catgaggaac    1020
accatcatgg catcaaaaac catcggaaca tctgaggaaa agctaaagaa aaagtcatct    1080
ttttaccaat cttacctacg gaggacacaa tctatgggga tacaactgga ccagcgcatc    1140
attgtgcttt ttatggttga ctggggaaaa gaggcagttg atagttttca tctcggtgac    1200
gatatggatc ctgagctccg gcgcctggca caggcattga ttgaccaaaa agtgaaggaa    1260
atatctaatc aggagccgct taagctttaa tag                                 1293

<210> SEQ ID NO 32
<211> LENGTH: 429
<212> TYPE: PRT
<213> ORGANISM: Dobrava virus

<400> SEQUENCE: 32

Met Ala Thr Leu Glu Glu Leu Gln Lys Glu Ile Asn Asn His Glu Gly
1               5                   10                  15

Gln Leu Val Ile Ala Arg Gln Lys Val Lys Asp Ala Glu Lys Gln Tyr
            20                  25                  30

Glu Lys Asp Pro Asp Asp Leu Asn Lys Arg Ala Leu Ser Asp Arg Glu
        35                  40                  45

Ser Ile Ala Gln Ser Ile Gln Gly Lys Ile Asp Glu Leu Arg Arg Gln
    50                  55                  60

Leu Ala Asp Arg Val Ala Ala Gly Lys Asn Ile Gly Lys Glu Arg Asp
```

```
                65                  70                  75                  80
        Pro Thr Gly Leu Asp Pro Gly Asp His Leu Lys Glu Lys Ser Met Leu
                            85                  90                  95
        Ser Tyr Gly Asn Val Ile Asp Leu Asn His Leu Asp Ile Asp Glu Pro
                            100                 105                 110
        Thr Gly Gln Thr Ala Asp Trp Leu Ser Ile Val Ile Tyr Leu Thr Ser
                            115                 120                 125
        Phe Val Val Pro Ile Leu Leu Lys Ala Leu Tyr Met Leu Thr Thr Arg
                    130                 135                 140
        Gly Arg Gln Thr Thr Lys Asp Asn Lys Gly Met Arg Ile Arg Phe Lys
        145                 150                 155                 160
        Asp Asp Ser Ser Phe Glu Asp Val Asn Gly Ile Arg Lys Pro Lys His
                            165                 170                 175
        Leu Phe Leu Ser Met Pro Asn Ala Gln Ser Ser Met Lys Ala Asp Glu
                            180                 185                 190
        Ile Thr Pro Gly Arg Phe Arg Thr Ala Ile Cys Gly Leu Tyr Pro Ala
                            195                 200                 205
        Gln Val Lys Ala Arg Asn Leu Ile Ser Pro Val Met Ser Val Ile Gly
                    210                 215                 220
        Phe Val Ala Leu Ala Lys Asn Trp Thr Glu Arg Val Glu Glu Trp Leu
        225                 230                 235                 240
        Asp Leu Pro Cys Lys Leu Leu Ser Glu Pro Ser Pro Thr Ser Leu Thr
                            245                 250                 255
        Lys Gly Pro Ser Thr Asn Arg Asp Tyr Leu Asn Gln Arg Gln Gly Ala
                            260                 265                 270
        Leu Ala Lys Met Glu Thr Lys Glu Ala Gln Ala Val Arg Lys His Ala
                            275                 280                 285
        Ile Asp Ala Gly Cys Asn Leu Ile Asp His Ile Asp Ser Pro Ser Ser
                    290                 295                 300
        Ile Trp Val Phe Ala Gly Ala Pro Asp Arg Cys Pro Pro Thr Cys Leu
        305                 310                 315                 320
        Phe Ile Ala Gly Met Ala Glu Leu Gly Ala Phe Phe Ala Cys Leu Gln
                            325                 330                 335
        Asp Met Arg Asn Thr Ile Met Ala Ser Lys Thr Ile Gly Thr Ser Glu
                            340                 345                 350
        Glu Lys Leu Lys Lys Ser Ser Phe Tyr Gln Ser Tyr Leu Arg Arg
                            355                 360                 365
        Thr Gln Ser Met Gly Ile Gln Leu Asp Gln Arg Ile Ile Val Leu Phe
                    370                 375                 380
        Met Val Asp Trp Gly Lys Glu Ala Val Asp Ser Phe His Leu Gly Asp
        385                 390                 395                 400
        Asp Met Asp Pro Glu Leu Arg Arg Leu Ala Gln Ala Leu Ile Asp Gln
                            405                 410                 415
        Lys Val Lys Glu Ile Ser Asn Gln Glu Pro Leu Lys Leu
                            420                 425

<210> SEQ ID NO 33
<211> LENGTH: 1290
<212> TYPE: DNA
<213> ORGANISM: Sin Nombre hantavirus

<400> SEQUENCE: 33
atgagcaccc tcaaagaagt gcaagacaac attactctcc acgaacaaca actcgtgact      60
gccaggcaga agctcaaaga tgcagagaga gcggtggaat tggaccccga tgatgttaac     120
```

-continued

```
aaaagcacat tacagagcag acgggcagct gtgtctgcat tggagaccaa actcggagaa      180
ctcaagcggg aactggctga tcttattgca gctcagaaat tggcttcaaa acctgttgat      240
ccaacaggga ttgaacctga tgaccattta aggaaaaat catcactgag atatggaaat       300
gtccttgatg taaattccat tgacctagaa gaaccaagtg gcaaacagc tgattggaaa       360 tccatcggac tctacattct aagttttgca ttaccgatta tccttaaagc cttgtacatg      420
ttatctacta gaggccgtca aacaatcaaa gaaaacaagg gaacaagaat tcgatttaag      480
gatgattcat cttatgaaga gtcaatgga atacgtaaac caagacatct atatgtttct       540
atgccaactg ctcagtctac aatgaaagca gatgagatta ctcctgggag gttccgtaca      600
attgcttgtg ggttattccc ggcccaagtc aaagcaagga atattatcag tcctgttgtg     660
ggtgtgattg gctttagttt ctttgtgaaa gattggatgg aaagaattga tgactttctg      720
gctgcacgtt gtccatttct acccgaacag aaagaccca gggatgctgc attggcaact       780
aacagagcct attttataac acgtcaatta caggttgatg agtcaaaggt tagtgatatt      840
gaggatctaa ttgctgatgc aagggctgag tctgccacta tattcgcaga tatcgcccact     900 cctcattcag tttgggtctt cgcatgtgct ccagatcgtt gtccacctac agcattatat      960
gtggccggga tgccggagtt gggtgcattt tttgctattc ttcaggatat gaggaacacc     1020
ataatggcat caaaatctgt ggggacatct gaagagaaat tgaagaaaaa atcagcattc     1080
taccagtcat acttgagacg tactcagtca atgggattc aactggacca gaagataatc      1140
atcttataca tgagccattg gggaagagag gccgtgaatc acttccatct tggagatgat     1200
atggatcttg aacttaggga acttgcccag accctcgtag acatcaaggt cagggagatc     1260
tctaaccaag aaccacttaa actttaatag                                     1290
```

<210> SEQ ID NO 34
<211> LENGTH: 428
<212> TYPE: PRT
<213> ORGANISM: Sin Nombre hantavirus

<400> SEQUENCE: 34

```
Met Ser Thr Leu Lys Glu Val Gln Asp Asn Ile Thr Leu His Glu Gln
1               5                   10                  15

Gln Leu Val Thr Ala Arg Gln Lys Leu Lys Asp Ala Glu Arg Ala Val
                20                  25                  30

Glu Leu Asp Pro Asp Asp Val Asn Lys Ser Thr Leu Gln Ser Arg Arg
            35                  40                  45

Ala Ala Val Ser Ala Leu Glu Thr Lys Leu Gly Glu Leu Lys Arg Glu
        50                  55                  60

Leu Ala Asp Leu Ile Ala Ala Gln Lys Leu Ala Ser Lys Pro Val Asp
65                  70                  75                  80

Pro Thr Gly Ile Glu Pro Asp Asp His Leu Lys Glu Lys Ser Ser Leu
                85                  90                  95

Arg Tyr Gly Asn Val Leu Asp Val Asn Ser Ile Asp Leu Glu Glu Pro
            100                 105                 110

Ser Gly Gln Thr Ala Asp Trp Lys Ser Ile Gly Leu Tyr Ile Leu Ser
        115                 120                 125

Phe Ala Leu Pro Ile Ile Leu Lys Ala Leu Tyr Met Leu Ser Thr Arg
    130                 135                 140

Gly Arg Gln Thr Ile Lys Glu Asn Lys Gly Thr Arg Ile Arg Phe Lys
145                 150                 155                 160
```

Asp Asp Ser Ser Tyr Glu Glu Val Asn Gly Ile Arg Lys Pro Arg His
            165                 170                 175

Leu Tyr Val Ser Met Pro Thr Ala Gln Ser Thr Met Lys Ala Asp Glu
            180                 185                 190

Ile Thr Pro Gly Arg Phe Arg Thr Ile Ala Cys Gly Leu Phe Pro Ala
            195                 200                 205

Gln Val Lys Ala Arg Asn Ile Ile Ser Pro Val Gly Val Ile Gly
        210                 215                 220

Phe Ser Phe Phe Val Lys Asp Trp Met Glu Arg Ile Asp Asp Phe Leu
225                 230                 235                 240

Ala Ala Arg Cys Pro Phe Leu Pro Glu Gln Lys Asp Pro Arg Asp Ala
                245                 250                 255

Ala Leu Ala Thr Asn Arg Ala Tyr Phe Ile Thr Arg Gln Leu Gln Val
            260                 265                 270

Asp Glu Ser Lys Val Ser Asp Ile Glu Asp Leu Ile Ala Asp Ala Arg
            275                 280                 285

Ala Glu Ser Ala Thr Ile Phe Ala Asp Ile Ala Thr Pro His Ser Val
            290                 295                 300

Trp Val Phe Ala Cys Ala Pro Asp Arg Cys Pro Thr Ala Leu Tyr
305                 310                 315                 320

Val Ala Gly Met Pro Glu Leu Gly Ala Phe Phe Ala Ile Leu Gln Asp
                325                 330                 335

Met Arg Asn Thr Ile Met Ala Ser Lys Ser Val Gly Thr Ser Glu Glu
            340                 345                 350

Lys Leu Lys Lys Ser Ala Phe Tyr Gln Ser Tyr Leu Arg Arg Thr
        355                 360                 365

Gln Ser Met Gly Ile Gln Leu Asp Gln Lys Ile Ile Leu Tyr Met
    370                 375                 380

Ser His Trp Gly Arg Glu Ala Val Asn His Phe His Leu Gly Asp Asp
385                 390                 395                 400

Met Asp Leu Glu Leu Arg Glu Leu Ala Gln Thr Leu Val Asp Ile Lys
            405                 410                 415

Val Arg Glu Ile Ser Asn Gln Glu Pro Leu Lys Leu
        420                 425

<210> SEQ ID NO 35
<211> LENGTH: 1290
<212> TYPE: DNA
<213> ORGANISM: Andes virus

<400> SEQUENCE: 35
atgagcaccc tccaagaatt gcaggaaaac atcacagcac acgaacaaca gctcgtgact      60
gctcggcaaa agcttaaaga tgccgagaag gcggtggagg tggacccgga tgacgttaac     120
aagagcacac tacaaaatag acgggcagct gtgtctacat tggagaccaa actcggggaa     180
ctcaagagac aacttgcaga tctggtggca gctcaaaaat tggctacaaa accagttgat     240
ccaacagggc ttgagcctga tgaccatctg aaagagaaat catctttgag atatgggaat     300
gtcctggatg ttaactcaat cgatttggaa gaaccgagtg gacagactgc tgattggaag     360
gctataggag catatatctt agggtttgca attccgatca tactaaaagc cctatatatg     420
ctgtcaaccc gtggaagaca gactgtgaaa gacaacaaag gaaccaggat aaggtttaag     480
gatgattctt cctttgaaga ggtcaatggg atacgtaaac cgaaacacct ttatgtctca     540
atgccaactg cacaatctac tatgaaggct gaggaaatta cgccaggacg gtttaggaca     600

```
attgcttgtg gcctctttcc agcacaggtc aaagctcgaa atataataag tcctgtgatg    660
ggagtaatcg gatttggctt ctttgtgaag gactggatgg atcggataga ggaattcctg    720
gctgcagagt gtccattcct gcctaagcca aaggttgcct cagaagcctt catgtctacc    780
aacaagatgt attttctgaa tagacaaaga caagtcaatg aatctaaggt tcaagacatc    840
attgatttaa tagatcatgc tgaaactgaa tctgctacct tgtttacaga aattgcaaca    900
ccccattcag tctgggtgtt tgcatgtgcg cctgaccggt gccctccgac tgcattgtat    960
gttgcagggg taccagaact tggtgcattc ttttccattc ttcaggacat gcgcaatacc   1020
atcatggcat ccaaatctgt ggggactgca gaagagaagc tgaagaagaa atctgccttt   1080
tatcaatctt acctaagaag gacacaatct atggggattc aactggacca gaaaatcata   1140
attctctaca tgctttcatg gggtaaagaa gctgtgaatc atttccatct tggtgatgat   1200
atggaccctg aactaaggca gctagctcaa tccctgattg acaccaaggt gaaggagatc   1260
tccaaccaag agccacttaa gttgtagtag                                    1290

<210> SEQ ID NO 36
<211> LENGTH: 428
<212> TYPE: PRT
<213> ORGANISM: Andes virus

<400> SEQUENCE: 36

Met Ser Thr Leu Gln Glu Leu Gln Glu Asn Ile Th

Phe Met Ser Thr Asn Lys Met Tyr Phe Leu Asn Arg Gln Arg Gln Val
            260                 265                 270

Asn Glu Ser Lys Val Gln Asp Ile Ile Asp Leu Ile Asp His Ala Glu
        275                 280                 285

Thr Glu Ser Ala Thr Leu Phe Thr Glu Ile Ala Thr Pro His Ser Val
        290                 295                 300

Trp Val Phe Ala Cys Ala Pro Asp Arg Cys Pro Pro Thr Ala Leu Tyr
305                 310                 315                 320

Val Ala Gly Val Pro Glu Leu Gly Ala Phe Phe Ser Ile Leu Gln Asp
            325                 330                 335

Met Arg Asn Thr Ile Met Ala Ser Lys Ser Val Gly Thr Ala Glu Glu
            340                 345                 350

Lys Leu Lys Lys Ser Ala Phe Tyr Gln Ser Tyr Leu Arg Arg Thr
            355                 360                 365

Gln Ser Met Gly Ile Gln Leu Asp Gln Lys Ile Ile Leu Tyr Met
            370                 375                 380

Leu Ser Trp Gly Lys Glu Ala Val Asn His Phe His Leu Gly Asp Asp
385                 390                 395                 400

Met Asp Pro Glu Leu Arg Gln Leu Ala Gln Ser Leu Ile Asp Thr Lys
                405                 410                 415

Val Lys Glu Ile Ser Asn Gln Glu Pro Leu Lys Leu
            420                 425

<210> SEQ ID NO 37
<211> LENGTH: 489
<212> TYPE: DNA
<213> ORGANISM: Artificial
<220> FEATURE:
<223> OTHER INFORMATION: human superoxide dismutase (SOD) sequence

<400> SEQUENCE: 37
atggctacaa aggctgtttg tgttttgaag ggtgacggcc cagttcaagg tattattaac     60
ttcgagcaga aggaaagtaa tggaccagtg aaggtgtggg aagcattaa aggactgact    120 gaaggcctgc atggattcca tgttcatgag tttggagata atacagcagg ctgtaccagt    180
gcaggtcctc actttaatcc tctatccgcg ctagccggtg ggccaaagga tgaagagagg    240
catgttggag acttgggcaa tgtgactgct gacaaagatg gtgtggccga tgtgtctatt    300
gaagattctg tgatctcact ctcaggagac cattgcatca ttggccgcac actggtggtc    360
catgaaaaag cagatgactt gggcaaaggt ggaaatgaag aaagtacaaa gacaggaaac    420
gctggaagtc gtttggcttg tggtgtaatt gggatcgccc agaatttgga attcacgcgt    480
caaaacaaa                                                            489

<210> SEQ ID NO 38
<211> LENGTH: 163
<212> TYPE: PRT
<213> ORGANISM: Artificial
<220> FEATURE:
<223> OTHER INFORMATION: human superoxide dismutase (SOD) sequence

<400> SEQUENCE: 38

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val

-continued

```
                35                  40                  45

His Glu Phe Gly Asp Asn Thr Ala Gly Cys Thr Ser Ala Gly Pro His
    50                  55                  60

Phe Asn Pro Leu Ser Ala Leu Ala Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Glu Phe Thr Arg
145                 150                 155                 160

Gln Asn Lys
```

<210> SEQ ID NO 39
<211> LENGTH: 43
<212> TYPE: PRT
<213> ORGANISM: Artificial
<220> FEATURE:
<223> OTHER INFORMATION: N protein fragment

<400> SEQUENCE: 39

```
Gln Leu Val Thr Ala Arg Gln Lys Leu Lys Asp Ala Glu Arg Ala Val
1               5                   10                  15

Glu Leu Asp Pro Asp Asp Val Asn Lys Ser Thr Leu Gln Ser Arg Arg
            20                  25                  30

Ala Ala Val Ser Ala Leu Glu Thr Lys Leu Gly
        35                  40
```

<210> SEQ ID NO 40
<211> LENGTH: 31
<212> TYPE: PRT
<213> ORGANISM: Artificial
<220> FEATURE:
<223> OTHER INFORMATION: G1 protein fragment

<400> SEQUENCE: 40

```
Leu Lys Ile Glu Ser Ser Cys Asn Phe Asp Leu His Val Pro Ala Thr
1               5                   10                  15

Thr Thr Gln Lys Tyr Asn Gln Val Asp Trp Thr Lys Lys Ser Ser
            20                  25                  30
```

<210> SEQ ID NO 41
<211> LENGTH: 5
<212> TYPE: PRT
<213> ORGANISM: Artificial
<220> FEATURE:
<223> OTHER INFORMATION: C-terminus of SOD sequence

<400> SEQUENCE: 41

```
Thr Arg Gln Asn Lys
1               5
```

<210> SEQ ID NO 42
<211> LENGTH: 244
<212> TYPE: PRT
<213> ORGANISM: Artificial
<220> FEATURE:

<223> OTHER INFORMATION: SOD/HTNV G1

<400> SEQUENCE: 42

Met Ala Th

```
Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
            130                 135                 140

Leu Ala Cys Gly Val Ile Gly Ile Ala Gln Asn Leu Glu Phe Thr Arg
145                 150                 155                 160

Gln Asn Lys Met Arg Leu Gly Gln Gly Leu Val Val Gly Ser Val Glu
                165                 170                 175

Leu Pro Ser Leu Pro Ile Gln Gln Val Glu Thr Leu Lys Leu Glu Ser
            180                 185                 190

Ser Cys Asn Phe Asp Leu His Thr Ser Thr Ala Gly Gln Gln Ser Phe
            195                 200                 205

Thr Lys Trp Thr Trp Glu Ile Lys Gly Asp Leu Ala Glu Asn Thr Gln
            210                 215                 220

Ala Ser Ser Thr Ser Phe Gln Thr Lys Ser Ser Glu Val Asn Leu Arg
225                 230                 235                 240

Gly Leu Cys Leu Ile Pro Thr
                245

<210> SEQ ID NO 44
<211> LENGTH: 244
<212> TYPE: PRT
<213> ORGANISM: Artificial
<220> FEATURE:
<223> OTHER INFORMATION: SOD/SEOV G1

<400> SEQUENCE: 44

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
    50                  55                  60

Phe Asn Pro Leu Ser Ala Leu Ala Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
            130                 135                 140

Leu Ala Cys Gly Val Ile Gly Ile Ala Gln Asn Leu Glu Phe Thr Arg
145                 150                 155                 160

Gln Asn Lys Met Lys Phe Gly Glu Thr Ser Val Ser Gly Tyr Thr Glu
                165                 170                 175

Leu Pro Pro Leu Ser Leu Gln Glu Ala Glu Gln Leu Val Pro Glu Ser
            180                 185                 190

Ser Cys Asn Met Asp Asn His Gln Ser Leu Ser Thr Ile Asn Lys Leu
            195                 200                 205
```

```
Thr Lys Val Ile Trp Arg Lys Lys Ala Asn Gln Glu Ser Ala Asn Gln
        210                 215                 220
Asn Ser Phe Glu Leu Met Glu Ser Glu Val Ser Phe Lys Gly Leu Cys
225                 230                 235                 240
Met Leu Lys His
```

<210> SEQ ID NO 45
<211> LENGTH: 244
<212> TYPE: PRT
<213> ORGANISM: Artificial
<220> FEATURE:
<223> OTHER INFORMATION: SOD/DOBV G1

<400> SEQUENCE: 45

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Ala Leu Ala Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Glu Phe Thr Arg
145                 150                 155                 160

Gln Asn Lys Met Asn Phe Gly Glu Ser Ser Val Thr Gly Lys Val Glu
                165                 170                 175

Leu Pro Pro Leu Leu Leu Thr Asp Ala Glu Ala Leu Val Pro Glu Ser
            180                 185                 190

Ser Cys Asn Met Asp Asn His Gln Ser Met Ser Ile Ile Gln Lys Val
        195                 200                 205

Thr Lys Val Ser Trp Arg Lys Lys Ala Asp Lys Ala Gln Ala Ala Lys
    210                 215                 220

Asp Ser Phe Glu Thr Thr Ser Ser Glu Val Asn Leu Lys Gly Thr Cys
225                 230                 235                 240

Thr Leu Ser His

<210> SEQ ID NO 46
<211> LENGTH: 247
<212> TYPE: PRT
<213> ORGANISM: Artificial
<220> FEATURE:
<223> OTHER INFORMATION: SOD/SNV G1

<400> SEQUENCE: 46

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val

```
                    20                  25                  30
Trp Gly Ser Ile Lys Gly Leu Thr Glu Gly Leu His Gly Phe His Val
                35                  40                  45
His Glu Phe Gly Asp Asn Thr Ala Gly Cys Thr Ser Ala Gly Pro His
 50                  55                  60
Phe Asn Pro Leu Ser Ala Leu Ala Gly Gly Pro Lys Asp Glu Glu Arg
 65                  70                  75                  80
His Val Gly Asp Leu Gly Asn Val Thr Ala Asp Lys Asp Gly Val Ala
                    85                  90                  95
Asp Val Ser Ile Glu Asp Ser Val Ile Ser Leu Ser Gly Asp His Cys
                100                 105                 110
Ile Ile Gly Arg Thr Leu Val Val His Glu Lys Ala Asp Asp Leu Gly
                115                 120                 125
Lys Gly Gly Asn Glu Glu Ser Thr Lys Thr Gly Asn Ala Gly Ser Arg
            130                 135                 140
Leu Ala Cys Gly Val Ile Gly Ile Ala Gln Asn Leu Glu Phe Thr Arg
145                 150                 155                 160
Gln Asn Lys Met Gly Leu Gly Gln Gly Tyr Val Thr Gly Ser Val Glu
                165                 170                 175
Ile Thr Pro Ile Leu Leu Thr Gln Val Ala Asp Leu Lys Ile Glu Ser
                180                 185                 190
Ser Cys Asn Phe Asp Leu His Val Pro Ala Thr Thr Gln Lys Tyr
                195                 200                 205
Asn Gln Val Asp Trp Thr Lys Lys Ser Ser Thr Glu Ser Thr Asn
            210                 215                 220
Ala Gly Ala Thr Thr Phe Glu Ala Lys Thr Lys Glu Ile Asn Leu Lys
225                 230                 235                 240
Gly Thr Cys Asn Ile Pro Pro
                245

<210> SEQ ID NO 47
<211> LENGTH: 247
<212> TYPE: PRT
<213> ORGANISM: Artificial
<220> FEATURE:
<223> OTHER INFORMATION: SOD/ANDV G1

<400> SEQUENCE: 47

Met Ala Thr Lys Ala Val Cys Val Leu Lys Gly Asp Gly Pro Val Gln
 1               5                  10                  15
Gly Ile Ile Asn Phe Glu Gln Lys Glu Ser Asn Gly Pro Val Lys Val
                20                  25                  30
Trp Gly Ser Ile Lys Gly Leu Thr Glu Gly Leu His Gly Phe His Val
                35                  40                  45
His Glu Phe Gly Asp Asn Thr Ala Gly Cys Thr Ser Ala Gly Pro His
 50                  55                  60
Phe Asn Pro Leu Ser Ala Leu Ala Gly Gly Pro Lys Asp Glu Glu Arg
 65                  70                  75                  80
His Val Gly Asp Leu Gly Asn Val Thr Ala Asp Lys Asp Gly Val Ala
                    85                  90                  95
Asp Val Ser Ile Glu Asp Ser Val Ile Ser Leu Ser Gly Asp His Cys
                100                 105                 110
Ile Ile Gly Arg Thr Leu Val Val His Glu Lys Ala Asp Asp Leu Gly
                115                 120                 125
Lys Gly Gly Asn Glu Glu Ser Thr Lys Thr Gly Asn Ala Gly Ser Arg
```

```
                        130             135             140
Leu Ala Cys Gly Val Ile Gly Ile Ala Gln Asn Leu Glu Phe Thr Arg
145                 150                 155                 160

Gln Asn Lys Met Gly Leu Gly Gln Gly Tyr Ile Ile Gly Ser Thr Glu
                165                 170                 175

Leu Gly Leu Ile Ser Ile Glu Ala Ala Ser Asp Ile Lys Leu Glu Ser
                180                 185                 190

Ser Cys Asn Phe Asp Leu His Thr Thr Ser

```
                245                 250                 255
Ser Met Leu Ser Tyr Gly Asn Val Leu Asp Leu Asn His Leu Asp Ile
            260                 265                 270

Asp Glu Pro Thr Gly Gln Thr Ala Asp Trp Leu Ser Ile Ile Val Tyr
        275                 280                 285

Leu Thr Ser Phe Val Val Pro Ile Leu Leu Lys Ala Leu Tyr Met Leu
        290                 295                 300

Thr Thr Arg Gly Arg Gln Thr Thr Lys Asp Asn Lys Gly Thr Arg Ile
305                 310                 315                 320

Arg Phe Lys Asp Ser Ser Phe Glu Asp Val Asn Gly Ile Arg Lys
                325                 330                 335

Pro Lys His Leu Tyr Val Ser Leu Pro Asn Ala Gln Ser Ser Met Lys
            340                 345                 350

Ala Glu Glu Ile Thr Pro Gly Arg Tyr Arg Thr Ala Val Cys Gly Leu
            355                 360                 365

Tyr Pro Ala Gln Ile Lys Ala Arg Gln Met Ile Ser Pro Val Met Ser
        370                 375                 380

Val Ile Gly Phe Leu Ala Leu Ala Lys Asp Trp Ser Asp Arg Ile Glu
385                 390                 395                 400

Gln Trp Leu Ile Glu Pro Cys Lys Leu Leu Pro Asp Thr Ala Ala Val
                405                 410                 415

Ser Leu Leu Gly Gly Pro Ala Thr Asn Arg Asp Tyr Leu Arg Gln Arg
            420                 425                 430

Gln Val Ala Leu Gly Asn Met Glu Thr Lys Glu Ser Lys Ala Ile Arg
        435                 440                 445

Gln His Ala Glu Ala Ala Gly Cys Ser Met Ile Glu Asp Ile Glu Ser
    450                 455                 460

Pro Ser Ser Ile Trp Val Phe Ala Gly Ala Pro Asp Arg Cys Pro Pro
465                 470                 475                 480

Thr Cys Leu Phe Ile Ala Gly Ile Ala Glu Leu Gly Ala Phe Phe Ser
                485                 490                 495

Ile Leu Gln Asp Met Arg Asn Thr Ile Met Ala Ser Lys Thr Val Gly
            500                 505                 510

Thr Ser Glu Glu Lys Leu Arg Lys Lys Ser Ser Phe Tyr Gln Ser Tyr
        515                 520                 525

Leu Arg Arg Thr Gln Ser Met Gly Ile Gln Leu Gly Gln Arg Ile Ile
        530                 535                 540

Val Leu Phe Met Val Ala Trp Gly Lys Glu Ala Val Asp Asn Phe His
545                 550                 555                 560

Leu Gly Asp Asp Met Asp Pro Glu Leu Arg Thr Leu Ala Gln Ser Leu
                565                 570                 575

Ile Asp Val Lys Val Lys Glu Ile Ser Asn Gln Glu Pro Leu Lys Leu
            580                 585                 590

<210> SEQ ID NO 49
<211> LENGTH: 596
<212> TYPE: PRT
<213> ORGANISM: Artificial
<220> FEATURE:
<223> OTHER INFORMATION: SOD/PUUV N

<400> SEQUENCE: 49

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
```

-continued

```
                    20                  25                  30
Trp Gly Ser Ile Lys Gly Leu Thr Glu Gly Leu His Gly Phe His Val
                35                  40                  45
His Glu Phe Gly Asp Asn Thr Ala Gly Cys Thr Ser Ala Gly Pro His
    50                  55                  60
Phe Asn Pro Leu Ser Ala Leu Ala Gly Gly Pro Lys Asp Glu Glu Arg
65                  70                  75                  80
His Val Gly Asp Leu Gly Asn Val Thr Ala Asp Lys Asp Gly Val Ala
                85                  90                  95
Asp Val Ser Ile Glu Asp Ser Val Ile Ser Leu Ser Gly Asp His Cys
                100                 105                 110
Ile Ile Gly Arg Thr Leu Val Val His Glu Lys Ala Asp Asp Leu Gly
                115                 120                 125
Lys Gly Gly Asn Glu Glu Ser Thr Lys Thr Gly Asn Ala Gly Ser Arg
            130                 135                 140
Leu Ala Cys Gly Val Ile Gly Ile Ala Gln Asn Leu Glu Phe Thr Arg
145                 150                 155                 160
Gln Asn Lys Met Ser Asp Leu Thr Asp Ile Gln Glu Glu Ile Thr Arg
                165                 170                 175
His Glu Gln Gln Leu Val Val Ala Arg Gln Lys Leu Lys Asp Ala Glu
                180                 185                 190
Arg Ala Val Glu Val Tyr Pro Asp Asp Val Asn Lys Asn Thr Leu Gln
            195                 200                 205
Ala Arg Gln Gln Thr Val Ser Ala Leu Glu Asp Lys Leu Ala Asp Tyr
        210                 215                 220
Lys Arg Arg Met Ala Asp Ala Val Ser Arg Lys Lys Met Asp Thr Lys
225                 230                 235                 240
Pro Thr Asp Pro Thr Gly Ile Glu Pro Asp His Leu Lys Glu Arg
                245                 250                 255
Ser Ser Leu Arg Tyr Gly Asn Val Leu Asp Val Asn Ala Ile Asp Ile
            260                 265                 270
Glu Glu Pro Ser Gly Gln Thr Ala Asp Trp Tyr Thr Ile Gly Val Tyr
        275                 280                 285
Val Ile Gly Phe Thr Ile Pro Ile Leu Lys Ala Leu Tyr Met Leu
    290                 295                 300
Ser Thr Arg Gly Arg Gln Thr Val Lys Glu Asn Lys Gly Thr Arg Ile
305                 310                 315                 320
Arg Phe Lys Asp Asp Thr Ser Phe Glu Asp Ile Asn Gly Ile Arg Arg
                325                 330                 335
Pro Lys His Leu Tyr Val Ser Met Pro Thr Ala Gln Ser Thr Met Lys
            340                 345                 350
Ala Glu Glu Leu Thr Pro Gly Arg Phe Arg Thr Ile Val Cys Gly Leu
        355                 360                 365
Phe Pro Thr Gln Ile Gln Val Arg Asn Ile Met Ser Pro Val Met Gly
    370                 375                 380
Val Ile Gly Phe Ser Phe Phe Val Lys Asp Trp Pro Glu Lys Ile Arg
385                 390                 395                 400
Glu Phe Met Glu Lys Glu Cys Pro Phe Ile Lys Pro Glu Val Lys Pro
                405                 410                 415
Gly Thr Pro Ala Gln Glu Val Glu Phe Leu Lys Arg Asn Arg Val Tyr
            420                 425                 430
Phe Met Thr Arg Gln Asp Val Leu Asp Lys Asn His Val Ala Asp Ile
        435                 440                 445
```

```
Asp Lys Leu Ile Asp Tyr Ala Ala Ala Gly Asp Pro Thr Ser Pro Asp
    450                 455                 460
Asp Ile Glu Ser Pro Asn Ala Pro Trp Val Phe Ala Cys Ala Pro Asp
465                 470                 475                 480
Arg Cys Pro Pro Thr Cys Ile Tyr Val Ala Gly Met Ala Glu Leu Gly
                485                 490                 495
Ala Phe Phe Ser Ile Leu Gln Asp Met Arg Asn Thr Ile Met Ala Ser
                500                 505                 510
Lys Thr Val Gly Thr Ala Glu Glu Lys Leu Lys Lys Ser Ser Phe
    515                 520                 525
Tyr Gln Ser Tyr Leu Arg Arg Thr Gln Ser Met Gly Ile Gln Leu Asp
    530                 535                 540
Gln Arg Ile Ile Leu Leu Tyr Met Leu Glu Trp Gly Lys Glu Met Val
545                 550                 555                 560
Asp His Phe His Leu Gly Asp Gly Met Asp Pro Glu Leu Arg Gly Leu
                565                 570                 575
Ala Gln Ser Leu Ile Asp Gln Lys Val Lys Glu Ile Ser Asn Gln Glu
                580                 585                 590
Pro Leu Lys Ile
        595

<210> SEQ ID NO 50
<211> LENGTH: 592
<212> TYPE: PRT
<213> ORGANISM: Artificial
<220> FEATURE:
<223> OTHER INFORMATION: SOD/SEOV N

<400> SEQUENCE: 50

Met Ala Thr Lys Ala Val Cys Val Leu Lys Gly Asp Gly Pro Val Gln
1               5                   10                  15
Gly Ile Ile Asn Phe Glu Gln Lys Glu Ser Asn Gly Pro Val Lys Val
                20                  25                  30
Trp Gly Ser Ile Lys Gly Leu Thr Glu Gly Leu His Gly Phe His Val
            35                  40                  45
His Glu Phe Gly Asp Asn Thr Ala Gly Cys Thr Ser Ala Gly Pro His
        50                  55                  60
Phe Asn Pro Leu Ser Ala Leu Ala Gly Gly Pro Lys Asp Glu Glu Arg
65                  70                  75                  80
His Val Gly Asp Leu Gly Asn Val Thr Ala Asp Lys Asp Gly Val Ala
                85                  90                  95
Asp Val Ser Ile Glu Asp Ser Val Ile Ser Leu Ser Gly Asp His Cys
                100                 105                 110
Ile Ile Gly Arg Thr Leu Val Val His Glu Lys Ala Asp Asp Leu Gly
            115                 120                 125
Lys Gly Gly Asn Glu Glu Ser Thr Lys Thr Gly Asn Ala Gly Ser Arg
        130                 135                 140
Leu Ala Cys Gly Val Ile Gly Ile Ala Gln Asn Leu Glu Phe Thr Arg
145                 150                 155                 160
Gln Asn Lys Met Ala Thr Met Glu Glu Ile Gln Arg Glu Ile Ser Ala
                165                 170                 175
His Glu Gly Gln Leu Val Ile Ala Arg Gln Lys Val Lys Asp Ala Glu
                180                 185                 190
Lys Gln Tyr Glu Lys Asp Pro Asp Asp Leu Asn Lys Arg Ala Leu His
            195                 200                 205
```

```
Asp Arg Glu Ser Val Ala Ala Ser Ile Gln Ser Lys Ile Asp Glu Leu
        210                 215                 220

Lys Arg Gln Leu Ala Asp Arg Ile Ala Ala Gly Lys Asn Ile Gly Gln
225                 230                 235                 240

Asp Arg Asp Pro Thr Gly Val Glu Pro Gly Asp His Leu Lys Glu Arg
            245                 250                 255

Ser Ala Leu Ser Tyr Gly Asn Thr Leu Asp Leu Asn Ser Leu Asp Ile
        260                 265                 270

Asp Glu Pro Thr Gly Gln Thr Ala Asp Trp Leu Thr Ile Ile Val Tyr
            275                 280                 285

Leu Thr Ser Phe Val Val Pro Ile Ile Leu Lys Ala Leu Tyr Met Leu
        290                 295                 300

Thr Thr Arg Gly Arg Gln Thr Ser Lys Asp Asn Lys Gly Met Arg Ile
305                 310                 315                 320

Arg Phe Lys Asp Ser Ser Tyr Glu Asp Val Asn Gly Ile Arg Lys
            325                 330                 335

Pro Lys His Leu Tyr Val Ser Met Pro Asn Ala Gln Ser Ser Met Lys
        340                 345                 350

Ala Glu Glu Ile Thr Pro Gly Arg Phe Arg Thr Ala Val Cys Gly Leu
        355                 360                 365

Tyr Pro Ala Gln Ile Lys Ala Arg Asn Met Val Ser Pro Val Met Ser
370                 375                 380

Val Val Gly Phe Leu Ala Leu Ala Lys Asp Trp Thr Ser Arg Ile Glu
385                 390                 395                 400

Glu Trp Leu Gly Ala Pro Cys Lys Phe Met Ala Glu Ser Pro Ile Ala
            405                 410                 415

Gly Ser Leu Ser Gly Asn Pro Val Asn Arg Asp Tyr Ile Arg Gln Arg
        420                 425                 430

Gln Gly Ala Leu Ala Gly Met Glu Pro Lys Glu Phe Gln Ala Leu Arg
        435                 440                 445

Gln His Ser Lys Asp Ala Gly Cys Thr Leu Val Glu His Ile Glu Ser
        450                 455                 460

Pro Ser Ser Ile Trp Val Phe Ala Gly Ala Pro Asp Arg Cys Pro Pro
465                 470                 475                 480

Thr Cys Leu Phe Val Gly Gly Met Ala Glu Leu Gly Ala Phe Phe Ser
            485                 490                 495

Ile Leu Gln Asp Met Arg Asn Thr Ile Met Ala Ser Lys Thr Val Gly
        500                 505                 510

Thr Ala Asp Glu Lys Leu Arg Lys Lys Ser Ser Phe Tyr Gln Ser Tyr
        515                 520                 525

Leu Arg Arg Thr Gln Ser Met Gly Ile Gln Leu Asp Gln Arg Ile Ile
        530                 535                 540

Val Met Phe Met Val Ala Trp Gly Lys Glu Ala Val Asp Asn Phe His
545                 550                 555                 560

Leu Gly Asp Asp Met Asp Pro Glu Leu Arg Ser Leu Ala Gln Ile Leu
            565                 570                 575

Ile Asp Gln Lys Val Lys Glu Ile Ser Asn Gln Glu Pro Met Lys Leu
        580                 585                 590

<210> SEQ ID NO 51
<211> LENGTH: 592
<212> TYPE: PRT
<213> ORGANISM: Artificial
<220> FEATURE:
```

<223> OTHER INFORMATION: SOD/DOBV N

<400> SEQUENCE: 51

```
Met Ala Thr Lys Ala Val Cys Val Leu L

```
Glu Trp Leu Asp Leu Pro Cys Lys Leu Leu Ser Glu Pro Ser Pro Thr
                405                 410                 415

Ser Leu Thr Lys Gly Pro Ser Thr Asn Arg Asp Tyr Leu Asn Gln Arg
            420                 425                 430

Gln Gly Ala Leu Ala Lys Met Glu Thr Lys Glu Ala Gln Ala Val Arg
        435                 440                 445

Lys His Ala Ile Asp Ala Gly Cys Asn Leu Ile Asp His Ile Asp Ser
450                 455                 460

Pro Ser Ser Ile Trp Val Phe Ala Gly Ala Pro Asp Arg Cys Pro Pro
465                 470                 475                 480

Thr Cys Leu Phe Ile Ala Gly Met Ala Glu Leu Gly Ala Phe Phe Ala
                485                 490                 495

Cys Leu Gln Asp Met Arg Asn Thr Ile Met Ala Ser Lys Thr Ile Gly
            500                 505                 510

Thr Ser Glu Glu Lys Leu Lys Lys Ser Ser Phe Tyr Gln Ser Tyr
        515                 520                 525

Leu Arg Arg Thr Gln Ser Met Gly Ile Gln Leu Asp Gln Arg Ile Ile
530                 535                 540

Val Leu Phe Met Val Asp Trp Gly Lys Glu Ala Val Asp Ser Phe His
545                 550                 555                 560

Leu Gly Asp Asp Met Asp Pro Glu Leu Arg Arg Leu Ala Gln Ala Leu
                565                 570                 575

Ile Asp Gln Lys Val Lys Glu Ile Ser Asn Gln Glu Pro Leu Lys Leu
            580                 585                 590

<210> SEQ ID NO 52
<211> LENGTH: 591
<212> TYPE: PRT
<213> ORGANISM: Artificial
<220> FEATURE:
<223> OTHER INFORMATION: SOD/SNV N

<400> SEQUENCE: 52

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Ala Leu Ala Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Glu Phe Thr Arg
145                 150                 155                 160

Gln Asn Lys Met Ser Thr Leu Lys Glu Val Gln Asp Asn Ile Thr Leu
                165                 170                 175
```

-continued

```
His Glu Gln Gln Leu Val Thr Ala Arg Gln Lys Leu Lys Asp Ala Glu
            180                 185                 190

Arg Ala Val Glu Leu Asp Pro Asp Val Asn Lys Ser Thr Leu Gln
        195                 200                 205

Ser Arg Arg Ala Ala Val Ser Ala Leu Glu Thr Lys Leu Gly Glu Leu
    210                 215                 220

Lys Arg Glu Leu Ala Asp Leu Ile Ala Ala Gln Lys Leu Ala Ser Lys
225                 230                 235                 240

Pro Val Asp Pro Thr Gly Ile Glu Pro Asp His Leu Lys Glu Lys
            245                 250                 255

Ser Ser Leu Arg Tyr Gly Asn Val Leu Asp Val Asn Ser Ile Asp Leu
            260                 265                 270

Glu Glu Pro Ser Gly Gln Thr Ala Asp Trp Lys Ser Ile Gly Leu Tyr
            275                 280                 285

Ile Leu Ser Phe Ala Leu Pro Ile Ile Leu Lys Ala Leu Tyr Met Leu
    290                 295                 300

Ser Thr Arg Gly Arg Gln Thr Ile Lys Glu Asn Lys Gly Thr Arg Ile
305                 310                 315                 320

Arg Phe Lys Asp Asp Ser Ser Tyr Glu Glu Val Asn Gly Ile Arg Lys
                325                 330                 335

Pro Arg His Leu Tyr Val Ser Met Pro Thr Ala Gln Ser Thr Met Lys
            340                 345                 350

Ala Asp Glu Ile Thr Pro Gly Arg Phe Arg Thr Ile Ala Cys Gly Leu
            355                 360                 365

Phe Pro Ala Gln Val Lys Ala Arg Asn Ile Ile Ser Pro Val Val Gly
    370                 375                 380

Val Ile Gly Phe Ser Phe Phe Val Lys Asp Trp Met Glu Arg Ile Asp
385                 390                 395                 400

Asp Phe Leu Ala Ala Arg Cys Pro Phe Leu Pro Glu Gln Lys Asp Pro
                405                 410                 415

Arg Asp Ala Ala Leu Ala Thr Asn Arg Ala Tyr Phe Ile Thr Arg Gln
            420                 425                 430

Leu Gln Val Asp Glu Ser Lys Val Ser Asp Ile Glu Asp Leu Ile Ala
        435                 440                 445

Asp Ala Arg Ala Glu Ser Ala Thr Ile Phe Ala Asp Ile Ala Thr Pro
    450                 455                 460

His Ser Val Trp Val Phe Ala Cys Ala Pro Asp Arg Cys Pro Pro Thr
465                 470                 475                 480

Ala Leu Tyr Val Ala Gly Met Pro Glu Leu Gly Ala Phe Phe Ala Ile
                485                 490                 495

Leu Gln Asp Met Arg Asn Thr Ile Met Ala Ser Lys Ser Val Gly Thr
            500                 505                 510

Ser Glu Glu Lys Leu Lys Lys Lys Ser Ala Phe Tyr Gln Ser Tyr Leu
        515                 520                 525

Arg Arg Thr Gln Ser Met Gly Ile Gln Leu Asp Gln Lys Ile Ile Ile
    530                 535                 540

Leu Tyr Met Ser His Trp Gly Arg Glu Ala Val Asn His Phe His Leu
545                 550                 555                 560

Gly Asp Asp Met Asp Leu Glu Leu Arg Glu Leu Ala Gln Thr Leu Val
                565                 570                 575

Asp Ile Lys Val Arg Glu Ile Ser Asn Gln Glu Pro Leu Lys Leu
            580                 585                 590
```

```
<210> SEQ ID NO 53
<211> LENGTH: 591
<212> TYPE: PRT
<213> ORGANISM: Artificial
<220> FEATURE:
<223> OTHER INFORMATION: SOD/ANDV N

<400> SEQUENCE: 53

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Ala Leu Ala Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Glu Phe Thr Arg
145                 150                 155                 160

Gln Asn Lys Met Ser Thr Leu Gln Glu Leu Gln Glu Asn Ile Thr Ala
                165                 170                 175

His Glu Gln Gln Leu Val Thr Ala Arg Gln Lys Leu Lys Asp Ala Glu
            180                 185                 190

Lys Ala Val Glu Val Asp Pro Asp Asp Val Asn Lys Ser Thr Leu Gln
        195                 200                 205

Asn Arg Arg Ala Ala Val Ser Thr Leu Glu Thr Lys Leu Gly Glu Leu
    210                 215                 220

Lys Arg Gln Leu Ala Asp Leu Val Ala Ala Gln Lys Leu Ala Thr Lys
225                 230                 235                 240

Pro Val Asp Pro Thr Gly Leu Glu Pro Asp Asp His Leu Lys Glu Lys
                245                 250                 255

Ser Ser Leu Arg Tyr Gly Asn Val Leu Asp Val Asn Ser Ile Asp Leu
            260                 265                 270

Glu Glu Pro Ser Gly Gln Thr Ala Asp Trp Lys Ala Ile Gly Ala Tyr
        275                 280                 285

Ile Leu Gly Phe Ala Ile Pro Ile Ile Leu Lys Ala Leu Tyr Met Leu
    290                 295                 300

Ser Thr Arg Gly Arg Gln Thr Val Lys Asp Asn Lys Gly Thr Arg Ile
305                 310                 315                 320

Arg Phe Lys Asp Asp Ser Ser Phe Glu Glu Val Asn Gly Ile Arg Lys
                325                 330                 335

Pro Lys His Leu Tyr Val Ser Met Pro Thr Ala Gln Ser Thr Met Lys
            340                 345                 350

Ala Glu Glu Ile Thr Pro Gly Arg Phe Arg Thr Ile Ala Cys Gly Leu
        355                 360                 365

Phe Pro Ala Gln Val Lys Ala Arg Asn Ile Ile Ser Pro Val Met Gly
```

-continued

```
                        370                 375                 380
Val Ile Gly Phe Gly Phe Phe Val Lys Asp Trp Met Asp Arg Ile Glu
385                 390                 395                 400

Glu Phe Leu Ala Ala Glu Cys Pro Phe Leu Pro Lys Pro Lys Val Ala
                405                 410                 415

Ser Glu Ala Phe Met Ser Thr Asn Lys Met Tyr Phe Leu Asn Arg Gln
                420                 425                 430

Arg Gln Val Asn Glu Ser Lys Val Gln Asp Ile Ile Asp Leu Ile Asp
            435                 440                 445

His Ala Glu Thr Glu Ser Ala Thr Leu Phe Thr Glu Ile Ala Thr Pro
    450                 455                 460

His Ser Val Trp Val Phe Ala Cys Ala Pro Asp Arg Cys Pro Pro Thr
465                 470                 475                 480

Ala Leu Tyr Val Ala Gly Val Pro Glu Leu Gly Ala Phe Phe Ser Ile
                485                 490                 495

Leu Gln Asp Met Arg Asn Thr Ile Met Ala Ser Lys Ser Val Gly Thr
                500                 505                 510

Ala Glu Glu Lys Leu Lys Lys Lys Ser Ala Phe Tyr Gln Ser Tyr Leu
            515                 520                 525

Arg Arg Thr Gln Ser Met Gly Ile Gln Leu Asp Gln Lys Ile Ile Ile
        530                 535                 540

Leu Tyr Met Leu Ser Trp Gly Lys Glu Ala Val Asn His Phe His Leu
545                 550                 555                 560

Gly Asp Asp Met Asp Pro Glu Leu Arg Gln Leu Ala Gln Ser Leu Ile
                565                 570                 575

Asp Thr Lys Val Lys Glu Ile Ser Asn Gln Glu Pro Leu Lys Leu
                580                 585                 590
```